US012616398B2

(12) United States Patent
Sandoval et al.

(10) Patent No.: US 12,616,398 B2
(45) Date of Patent: May 5, 2026

(54) SYSTEMS AND METHODS FOR MONITORING AN ANALYTE OR PARAMETER FOR A PATIENT

(71) Applicant: The General Hospital Corporation, Boston, MA (US)

(72) Inventors: Juan Pedro Cascales Sandoval, Somerville, MA (US); Conor L. Evans, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 596 days.

(21) Appl. No.: 18/043,659

(22) PCT Filed: Sep. 1, 2021

(86) PCT No.: PCT/US2021/048747
§ 371 (c)(1),
(2) Date: Mar. 1, 2023

(87) PCT Pub. No.: WO2022/051423
PCT Pub. Date: Mar. 10, 2022

(65) Prior Publication Data
US 2023/0263392 A1 Aug. 24, 2023

Related U.S. Application Data

(60) Provisional application No. 63/073,426, filed on Sep. 1, 2020.

(51) Int. Cl.
*A61B 5/1455* (2006.01)
*A61B 5/00* (2006.01)
(Continued)

(52) U.S. Cl.
CPC ............ *A61B 5/14552* (2013.01); *A61B 5/01* (2013.01); *A61B 5/14556* (2013.01); *A61B 5/1459* (2013.01); *A61B 5/6849* (2013.01)

(58) Field of Classification Search
CPC ........ G01N 27/026; G01N 33/18; G06F 1/20; G06F 2200/201; G06N 3/04; H05K 7/203;
(Continued)

(56) References Cited

U.S. PATENT DOCUMENTS 4,947,850 A    8/1990    Vanderkooi et al.
5,593,854 A    1/1997    Berndt
(Continued)

FOREIGN PATENT DOCUMENTS

EP    0760093 B1    4/1998
EP    0850409 B1    10/2003
(Continued)

OTHER PUBLICATIONS

Cascales et al., "Wearable device for remote monitoring of transcutaneous tissue oxygenation," 2020.
(Continued)

*Primary Examiner* — Jennifer Wecker
*Assistant Examiner* — Jonathan Bortoli
(74) *Attorney, Agent, or Firm* — QUARLES & BRADY LLP

(57) ABSTRACT
A sensor system includes a probe, and a photon source configured to direct photons at the probe. The probe can emit light in response to receiving photons. The sensor system can include a photodetector configured to detect the light emitted from the probe, and a configured to cause the photon source to emit photons according to a first time-varying intensity profile having a first frequency. The controller can be configured to receive optical data from the photodetector based on the interaction between the light emitted from the probe and the photodetector. The optical data can include a second time-varying intensity profile having a second frequency. The second frequency can be substantially the same
(Continued)

as the first frequency. The controller can be configured to determine a difference in phase between the first time-varying intensity profile and the second time-varying intensity profile, and generate a report based on the difference in phase.

20 Claims, 42 Drawing Sheets

(51) Int. Cl.
   *A61B 5/01*       (2006.01)
   *A61B 5/1459*     (2006.01)

(58) Field of Classification Search
   CPC ........ H05K 7/20818; A61B 2560/0233; A61B 2562/0233; A61B 2562/0271; A61B 5/0008; A61B 5/0071; A61B 5/01; A61B 5/14539; A61B 5/14552; A61B 5/14556; A61B 5/14557; A61B 5/1459; A61B 5/1495; A61B 5/681; A61B 5/6849; A61B 5/7203; A61B 5/7221; A61B 5/7267; A61B 5/746; G01J 1/58; G01J 3/0218; G01J 3/0291
   See application file for complete search history.

(56)                References Cited

U.S. PATENT DOCUMENTS

| | | |
|---|---|---|
| 6,138,082 A | 10/2000 | Wang et al. |
| 7,736,590 B2 | 6/2010 | Matsuda et al. |
| 8,080,810 B2 | 12/2011 | Aasmul |
| 9,789,206 B2 | 10/2017 | Evans et al. |
| 10,016,164 B2 | 7/2018 | Evans et al. |
| 10,524,707 B2 | 1/2020 | Li et al. |
| 2003/0031410 A1 | 2/2003 | Schnitzer |
| 2007/0172392 A1 | 7/2007 | Sen et al. |
| 2009/0283699 A1 | 11/2009 | Baltz et al. |
| 2011/0108739 A1 | 5/2011 | Hanko |
| 2013/0317325 A1 | 11/2013 | Wood |
| 2015/0223681 A1 | 8/2015 | Kuranov et al. |
| 2018/0214062 A1* | 8/2018 | Keating ............. A61K 49/0004 |
| 2019/0150811 A1 | 5/2019 | Evans et al. |
| 2019/0308030 A1 | 10/2019 | Bourke, Jr. et al. |

FOREIGN PATENT DOCUMENTS

| | | |
|---|---|---|
| JP | S61118057 U | 7/1986 |
| JP | 2003004635 A | 1/2003 |
| WO | 2005033746 A2 | 4/2005 |
| WO | 2013130510 A1 | 9/2013 |

OTHER PUBLICATIONS

International Search Report and Written Opinion for corresponding Application No. PCT/US2021/048747 mailed Dec. 14, 2021.
Japanese Office Action mailed Mar. 26, 2024, 14 pages, Japanese Patent Office.
Supplementary European Search Report in EP21865070.3.
Notice on the First Action in Chinese Application No. 202180074745.0.

* cited by examiner

---- COLLECTION FILTER
——— EXCITATION FILTER #1
-·-·- EXCITATION FILTER #2

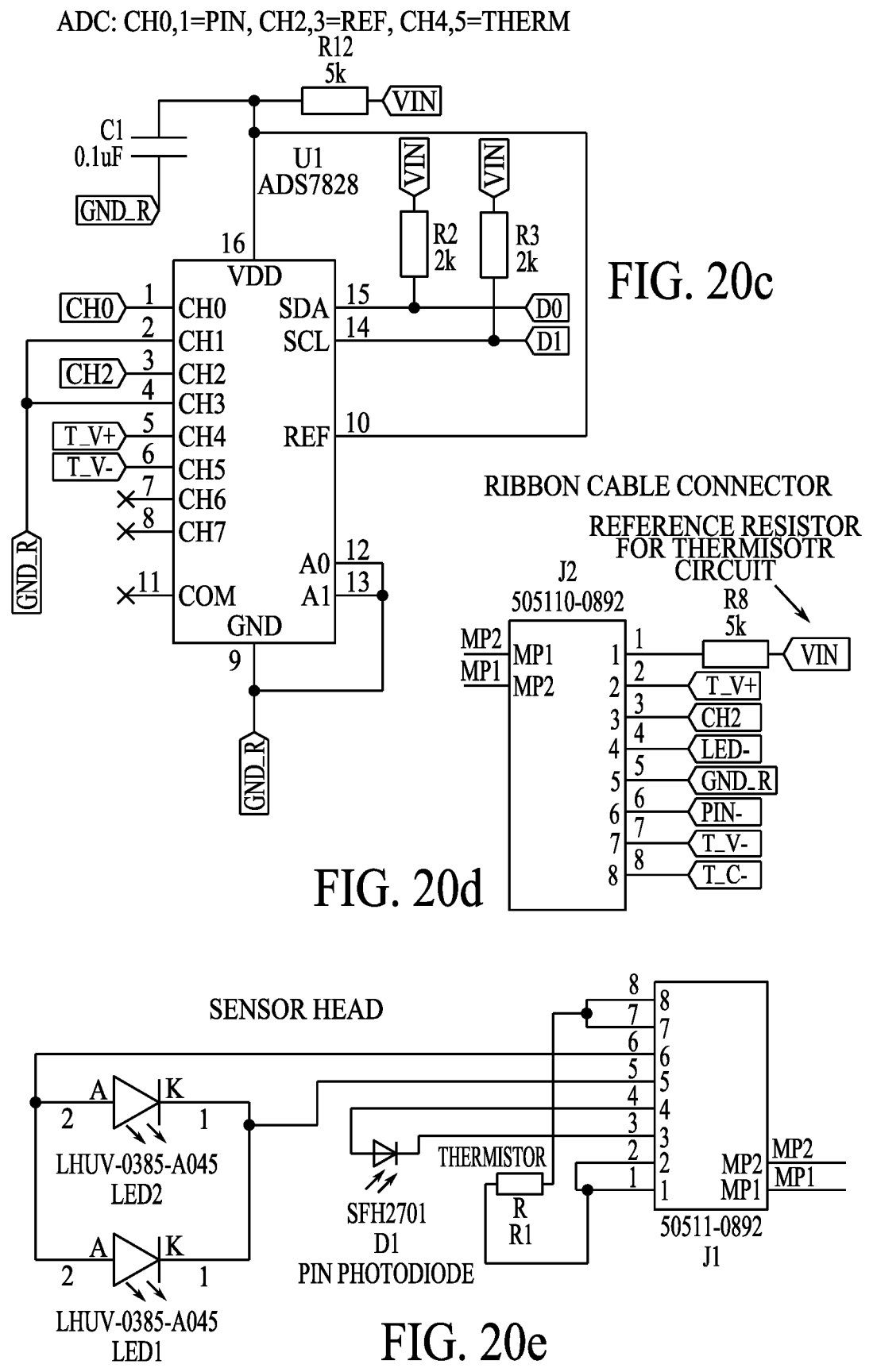

ADC: CH0,1=PIN, CH2,3=REF, CH4,5=THERM

R12
5k
[VIN]

C1
0.1uF

[GND_R]

U1
ADS7828

R2
2k

R3
2k

[VIN]    [VIN]

16
VDD

[CH0] 1  CH0    SDA  15  [D0]
      2  CH1    SCL  14  [D1]
[CH2] 3  CH2
      4  CH3
[T_V+] 5 CH4    REF  10
[T_V-] 6 CH5
      7  CH6
      8  CH7
         COM   A0  12
      11        A1  13
         GND
          9

FIG. 20c

[GND_R]

[GND_R]

RIBBON CABLE CONNECTOR

REFERENCE RESISTOR
FOR THERMISOTR
CIRCUIT

J2
505110-0892

R8
5k

MP2  MP1
MP1  MP2

1  1  [VIN]
2  2  [T_V+]
3  3  [CH2]
4  4  [LED-]
5  5  [GND_R]
6  6  [PIN-]
7  7  [T_V-]
8  8  [T_C-]

FIG. 20d

SENSOR HEAD 8
7
6
5
4
3
2
1

A  K
2        1
LHUV-0385-A045
LED2

A  K
2        1
LHUV-0385-A045
LED1

SFH2701
D1
PIN PHOTODIODE

THERMISTOR

PT (II)-PIVALOYL

PT (II)-ALKYNE

FIG. 28

SYSTEMS AND METHODS FOR MONITORING AN ANALYTE OR PARAMETER FOR A PATIENT

CROSS-REFERENCE TO RELATED APPLICATIONS

This application represents the national stage entry of PCT International Application No. PCT/US2021/048747 filed Sep. 1, 2021, which claims priority to U.S. Patent Application No. 63/073,426 filed Sep. 1, 2020, and entitled, "System and Methods for Multi-Dye Frequency Fluorimetry and Phosphorimetry," which are hereby incorporated by reference in their entirety.

STATEMENT REGARDING FEDERALLY SPONSORED RESEARCH

This invention was made with government support under FA9550-17-1-0277 awarded by the U.S. Department of Defense's Air Force Office of Scientific Research, and in particular, the Military Medical Photonics Program of the U.S. Department of Defense. This invention was also made with government support under HU0001-17-2-009 awarded by the Military Medicine Transforming Technology Collaborative's Henry M. Jackson Foundation. The government has certain rights in the invention.

BACKGROUND

Wearable devices have found widespread applications in recent years as both medical devices as well as consumer electronics for sports and health tracking. For example, pulse oximetry is currently used to measure oxygen saturation of hemoglobin in the blood, which can be indicative of systemic oxygen levels. However, these devices lack the ability to directly measure oxygen in tissues (e.g., transcutaneous oxygen monitoring), and thus these devices are not particularly helpful in predicting wound healing, determining an amputation level (e.g., an optimal point to amputate a limb), monitoring hyperbaric oxygen therapy, determining a severity of ischemia, etc. Thus, it would be desirable to have improved portable/wearable systems and methods for oxygen sensing.

SUMMARY OF THE DISCLOSURE

Some embodiments of the disclosure provide sensor systems or methods for monitoring a patient. The systems or methods can utilize probes for monitoring parameters, such as an analyte. The probe can be configured to have more than one operational range or to monitor more than one analyte or to determine multiple parameters associated with the analyte, or the like. A controller can create, selected, or determine a time-varying profile that can excite the probe relative to the more than one operational range, more than one analyte, or multiple parameters, or the like. Additionally or alternatively, the controller can adjust the time-varying profile to switch between the more than one operational range, more than one analyte, or multiple parameters, or the like.

In accordance with one aspect of the disclosure, a sensor system is provided for monitoring a patient. The system includes a probe sensitive to at least one analyte and having at least a first operational range and a second operational range for monitoring a patient, a photon source configured to direct photons at the probe, the probe emitting light in response to receiving photons from the photon source, and a photodetector configured to detect the light emitted from the probe. The system also includes a controller in communication with the photon source and the photodetector. The controller is configured to cause the photon source to direct photons at the probe according to a first time-varying profile to excite the probe relative to the first operational range and the second operational range to emit the light in response to receiving the photons and receive optical data from the photodetector based on the interaction between the light emitted from the probe while operating in the first operational range and the second operational range and the photodetector, wherein the optical data includes a second time-varying profile. The controller is further configured to determine a difference between the first time-varying profile and the second time-varying profile and determine a parameter associated with the analyte based on the difference between the first time-varying profile and the second time-varying profile.

In accordance with another aspect of the disclosure, a sensor system is provided that includes a probe, a photon source, a photodetector, and a controller in communication with the photon source and the photodetector. The controller is configured to generate a first time-varying profile including at least two first sub-signals configured to excite the probe relative to both of the at least two first sub-signals and cause the photon source to direct photons at the probe according to the first time-varying profile and excite the probe to emit light in response to receiving the photons. The controller is also configured to receive optical data from the photodetector based on the interaction between the light emitted from the probe and the photodetector, determine a second time-varying profile from the optical data and extract at least two second sub-signals, and determine a condition of a parameter by comparing the at least two first sub-signals to the at least two second sub-signals.

In accordance with yet another aspect of the disclosure, a sensor system is provided that includes a probe sensitive to changes in a parameter associated with a medical patient over a variety of operational ranges, a photon source, and a photodetector. The system also includes a controller in communication with the photon source and the photodetector. The controller being configured to cause the photon source to direct photons at the probe according to a first time-varying profile composed of multiple first sub-signals, the probe emitting light in response to receiving the photons directed to at the probe based on the first time-varying profile composed of multiple first sub-signals that is simultaneously responsive to both of the multiple first sub-signals. The controller is further configured to receive optical data from the photodetector based on the interaction between the light emitted from the probe and the photodetector, where the optical data includes a second time-varying profile. The controller is configured to extract response information from the optical data forming multiple second sub-signals to determine at least one of a difference in phase between the multiple first sub-signals and the multiple second sub-signals, a time delay reflected in the multiple first sub-signals and the multiple second sub-signals, or a time constant of the multiple second sub-signals. The controller is further configured to, based on the determining, generate a report on a condition of the parameter over the variety of operational ranges.

In accordance with another aspect of the disclosure, a method for is provided for monitoring a condition of a patient. The method includes positioning a probe proximate to the patient to monitor an analyte, positioning a photon source to deliver photons to the probe to excite the probe, and positioning a photodetector to receive light emitted by the probe in response to being exited by the photon source. The method further includes operating a controller in communication with the photon source and the photodetector to generate a first time-varying intensity profile including at least two first sub-signals configured to excite the probe relative to both of the at least two first sub-signals and cause the photon source to direct photons at the probe according to the first time-varying profile and excite the probe to emit light in response to receiving the photons. The controller is further operated to receive optical data from the photodetector based on the interaction between the light emitted from the probe and the photodetector, determine a second time-varying profile from the optical data and extract at least two second sub-signals, and generate a report regarding the analyte or a condition of a patient by comparing the at least two first sub-signals to the at least two second sub-signals.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of non-limiting examples of the disclosure and are not intended to limit the scope of the disclosure or exclude alternative implementations.

FIG. 14 shows panels a, b, c, and d. Panel a shows the variation of the temperature (measured by the thermistor in the sensor head) and $pO_2$ (measured by a commercial oxygen sensor) in a sealed chamber during calibration, in which the oxygen partial pressure is varied by mixing nitrogen and air at different ratios. Panel b shows an ADC output of the photodiode and reference signal channels at different points in time throughout the calibration. The photodiode signal reveals how the phosphorescence of the oxygen sensing film changes in amplitude and phase with respect to the reference signal during changes in oxygen (and temperature to a lesser degree). The reference signal remains stable during the measurement. Panel c shows the phase (minus the initial value at t=0) of the reference and photodiode signal vs time during the calibration period. The relative phase between the photodiode and reference signal, $\theta=\theta_p-\theta_r$, exhibits high sensitivity to changes in $pO_2$ throughout the whole physiological range. Panel d shows the amplitude of the emission I vs time, presenting a similar response to the phase. Phase and amplitude are obtained with a multiple linear regression algorithm from the data in panel b.

FIG. 17 shows panels a, b, c, d, e, and f Panel a shows a Stern-Volmer plot of lifetime data and its fit to the temperature dependent Stern-Volmer equation. The model is able to describe the variation of the measured lifetime with changes in partial pressure of oxygen and temperature. Panel b shows complimentary lifetime data vs temperature. The dependence of lifetime with temperature is accounted for by modelling Keff as a second order polynomial depending on temperature. Panel c shows a comparison of $pO_2$ measured by the developed device and a commercial reference sensor along with a 95% confidence interval (CI) of measurements. The $pO_2$ estimated from lifetime data reproduces all features observed in the reference $pO_2$ data with slight differences attributed to mismatches in sensor speed and temperature compensation. Panels d, e, and f show equivalent plots of panels a, b, and c, repetitively, for the intensity data revealing similar features.

FIG. 18 shows panels a, b and c. Panel a shows an illustration of the experimental set-up. Blood flow was occluded in a front limb of a Yorkshire swine by applying a tourniquet over the elbow joint to induce changes in tissue oxygenation. The wearable was placed over a shaved area of skin on the upper limb. Panel b shows the temperature and $pO_2$ (estimated from lifetime and intensity) during the experiment. As seen in both the estimates of $pO_2$ and temperature, the device is sensitive to physiological changes due to the compromised blood flow to the limb during the full occlusion. Panel c shows time derivatives of both partial oxygen pressure estimates that reveal a faster rate of change of the local oxygenation for the minutes following application and removal of the tourniquet.

FIG. 20 shows panels a, b, c, d, and e. Panel a shows a schematic of the reference signal conditioning circuit. Panel b shows the signals at different nodes of panel a measured by an oscilloscope, with a final reference signal with a mean value at 3.3 V which drives the LEDs. Panel c shows a schematic of the ADC circuit. Panel d shows a schematic of the ribbon cable connections. Panel e shows the sensor head schematic.

FIG. 28 shows molecular structures of Pt(II)-alkyne-porphyrin (left) and Pt(II)-pivaloyl-porphyrin (right) used for the formulations.

FIG. 29 also shows panels a, b, and c. Panel a shows a needle/catheter containing the porphyrin-PPMA coated fiber, panel b shows the needle/catheter after recoating with silicone, and panel c shows a thermocouple that was placed inside the needle next to the fiber. The obtained spectrum is shown on the right with emission (red) and excitation peaks (blue). The 375 nm excitation light was partially blocked with a 400 nm long-pass filter, with the peak seen in the spectrum being the tail of the excitation light from the LED that was not blocked by the filter.

DETAILED DESCRIPTION OF THE PRESENT DISCLOSURE

Figure 1:
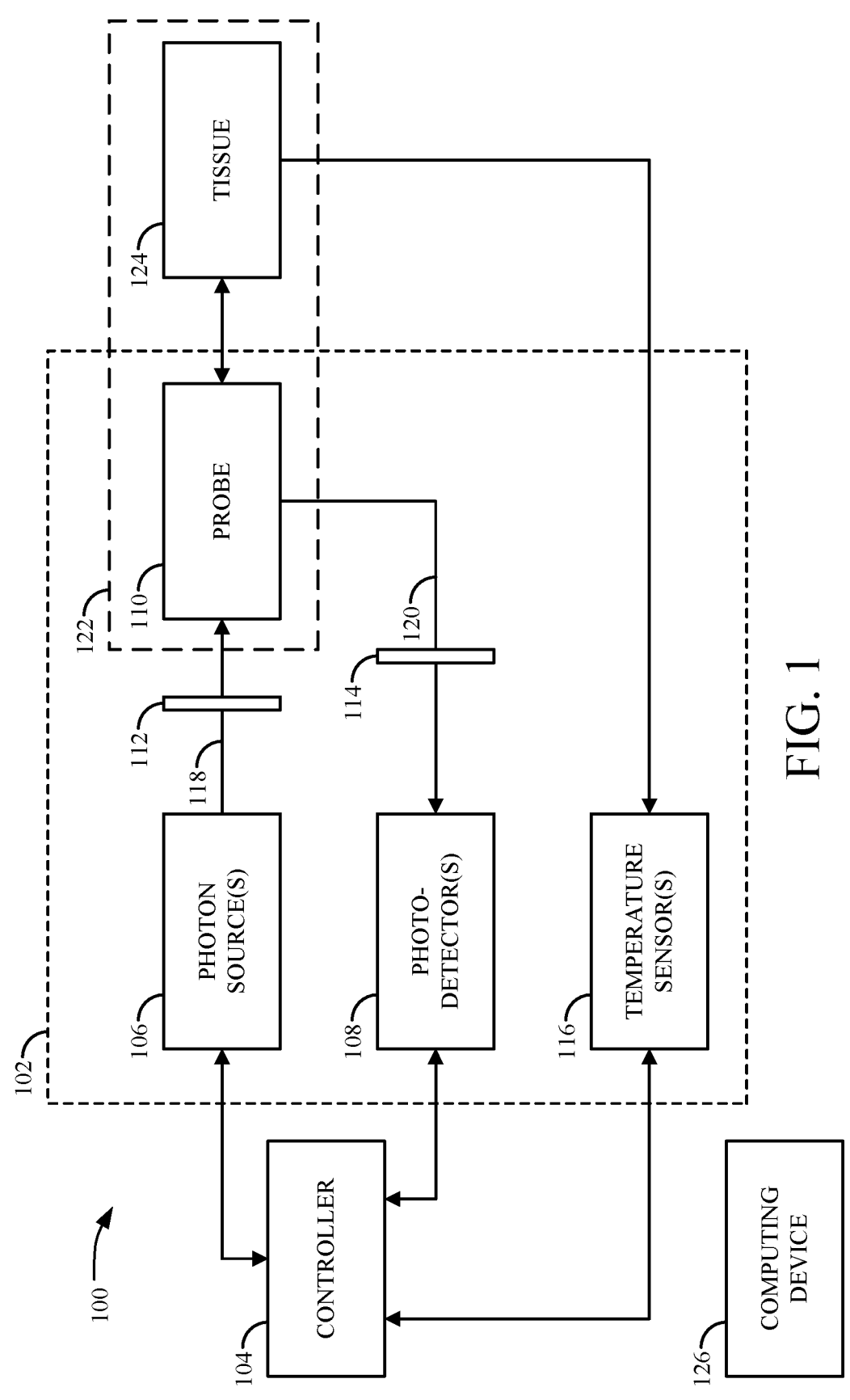
FIG. 1 shows a schematic illustration of a block diagram of a sensor system.

Some typical transcutaneous oxygen monitors rely on the photoluminescent quenching property of an oxygen-sensitive material. For example, as excitation light is directed at the oxygen-sensitive material functioning as a probe, the oxygen-sensitive material emits, in response, light (e.g., at a lower energy). The amount of light emitted by the oxygen-sensitive probe is dependent on the partial pressure of oxygen that surrounds (and is thus diffused into) the oxygen-sensitive probe. Thus, the intensity value of light received by the oxygen-sensitive probe can be used to determine the oxygen partial pressure. However, these strictly intensity-based approaches can have downsides. First, the intensity-based approach relies heavily on a proper orientation (or placement) of the oxygen-sensitive probe. For example, different orientations and positions (as compared to a cali-brated orientation) can lead to errors from the true oxygen partial pressure (e.g., the oxygen-sensitive probe not receiv-ing the correct amount of excitation light, or the photode-tector not receiving the correct amount of emitted light). Second, the amplitude-based approach is reliant on unchanging environmental conditions. For example, ambi-ent light (or other sources of light including other photolu-minescent materials) can undesirably influence the intensity value (and thus the determined oxygen partial pressure). As another example, humidity, temperature, sweat, etc., can each undesirably influence the amplitude value (and thus the determined oxygen partial pressure). As yet another example, over time the oxygen-sensitive material can degrade (e.g., can undergo photobleaching) in which the photoluminescent materials lose the ability to emit light in response to excitation light, thus leading to lower than actual partial pressure values (e.g., due to a lower intensity value).

As will be described, the present disclosure provides a variety of systems and methods that overcome these short-comings. For example, a sensor system is provided. The sensor system can include one or more probes, and a photon source configured to direct photons at one or more probes. The one or more probes can emit light in response to receiving photons from the photon source. The photon source can be excited by a time-varying profile that can be composed of one or more frequencies, wavelengths, wave-forms, periods, amplitudes, or the like. Thus, the probe can be driven using a time-varying profile that is formed from combination of parameters (e.g., waveforms, wavelengths, periods, amplitudes, and frequencies). The combination of parameters can be applied simultaneously or can be adjusted over time, such as to select between different operational ranges of the probe, to target different analytes, or the like.

For example, each set of parameters (e.g., waveforms, wavelengths, periods, amplitudes, and/or frequencies) can be selected to specifically target information readout from specific sensing probes. This can be configured so that each of these probes (e.g., phosphors/phosphorescent regions) has different characteristics or configurations (e.g., sensitivity or response curves) such that measuring multiple of these yields an overall operational range, for example, sensitivity or accuracy, that is greater than can be achieved with just one probe or one probe used at a time or at a given location.

In other embodiments, the luminescent response of mul-tiple probes (e.g. phosphors/fluorophors) excited by the same photon source may each respond to different analytes (e.g. oxygen, carbon dioxide, nitric oxide, etc.). In this way, a probe formed of multiple probes is controlled to yield readings of multiple analytes, which can occur simultane-ously or by switching between analytes.

The sensor system can include a photodetector configured to detect the light emitted from the probe, and a controller in communication with the photon source and the photode-tector. The controller can be configured to cause the photon source to direct photons at the probe according to a first time-varying intensity profile having a first frequency. The probe can emit the light in response to receiving the photons. The controller can be configured to receive optical data from the photodetector based on the interaction between the light emitted from the probe and the photodetector. The optical data can include a second time-varying intensity profile having a second frequency. The second frequency can be substantially the same, or exactly the same, as the first frequency. Also, the second frequency can be different than the first frequency. The frequencies can be time varying or have variations in phase. Additional frequencies can also be used. In this case, the analysis of the first and second time-varying profiles can be performed relative to individual frequencies. The controller can be configured to analyze the optical data to determine a predetermined parameter or information of interest. For example, the controller can be configured to determine a difference in phase between the first time-varying intensity profile and the second time-varying intensity profile, and determine a parameter, for example, an oxygen partial pressure based on the difference in phase.

Some embodiments of the disclosure provide advantages over oxygen monitors having these issues (and others) by providing improved systems and methods for oxygen sens-ing. For example, some embodiments provide an oxygen sensor system that can include an oxygen sensor, which can include a probe. The oxygen sensor can emit light from the probe and receive light in the form of optical data. This optical data can be used to determine response information, which can include a time delay, a phase difference, or a time constant. This response information is related to the triplet excited state lifetime of the probe, which can be used to determine the oxygen partial pressure. Because the response information is largely independent of the amplitude values from the received light of the probe, this approach eliminates many of the issues described above with regard to the strictly amplitude-based approach. In addition, again because the response information is largely independent of the amplitude values, the oxygen sensor does not need to be frequently calibrated based on changing conditions that would other-wise undesirably impact the accuracy of the oxygen partial pressure measurements. Rather, an initial calibration can last much longer and can be done by professionals (e.g., in a factory), rather than being conducted by an end user.

FIG. 1 shows a schematic illustration of a block diagram of a sensor system 100. The sensor system 100 can include a sensor 102, and a controller 104 in communication with the sensor 102. The sensor 102 can include a photon source(s) 106, a photodetector(s) 108, a probe 110, optical filters 112, 114, and temperature sensor(s) 116. The photon source(s) 106 can include one or more photon sources (e.g., one, two, three, four), and in some cases, the photon source(s) 106 can include a single photon source. Each photon source 106 can be optically coupled to the probe 110 and can be configured to emit respective light 118 towards the probe 110, which causes the probe 110 to emit light 120 in response to absorbing the light 118. For example, the light 118 can interact with a photoluminescent material of the probe 110 to emit photoluminescent light. As a more specific example, the light 118 can interact with a phosphorescent material of the probe 110 to emit phosphorescent light.

In some embodiments, the light 118 can be emitted so that the amplitude of the light 118 (e.g., the intensity of the light 118) changes over time. For example, the light 118 can be emitted according to a time-varying intensity profile. Addi-tionally or alternatively, a time-varying profile can have a single frequency (e.g., have a single fundamental fre-quency), or can have multiple different frequencies (e.g., multiple harmonics of and including a fundamental fre-quency). In some cases, the time-varying profile can be composed of sine waves, square waves, impulse functions (e.g., a delta function), or a portion of each of these, etc. In some configurations, the time-varying profile can be a periodic wave (e.g., a sine wave), in other cases, the time-varying profile can be a non-periodic wave (e.g., a portion of a sine wave, a single square pulse, etc.). Additionally, as will be described, the time-varying profile and, thus, the excitation field created by the light 118 can be driven at a combination of these characteristics (e.g., intensity, frequency, waveform, period, etc.). For example, the excitation field created by the light 118 can be driven at a combination of waveforms and frequencies, with each set of waveforms and/or frequencies specifically targeting information readout from specific sensing probes or operational ranges of a probe or probes forming a probe. This can be configured so that each of these probes (e.g., phosphors/phosphorescent regions) has different sensitivity or response curves such that measuring multiple of these yields a device that has a greater range of sensitivity or accuracy than just one probe or one probe used at a time or at a given location. In other embodiments, different types of probes (phosphors/fluorophors) can each be sensitive to a different analyte (e.g. oxygen, carbon dioxide, nitric oxide, etc.) but excited by the same photon source, such that a single measurement of the probes yields a device which provides simultaneous readings of multiple analytes.

In some configurations, the controller 104 (or the oxygen sensor 102) can include a function generator that is configured to output an electrical waveform to drive each photon source 106 according to the time-varying intensity profile. For example, an electrical waveform that defines a wave (e.g., a sine wave) can be applied to the photon source 106 to cause the photon source 106 to emit the light 118 according to the time-varying intensity profile (e.g., the sine wave). In some cases, including when the photon source(s) 106 includes multiple photon sources, the function generator (or multiple function generators) can each output a respective electrical waveform to a respective photon source 106, each of which can be different from each other (e.g., thereby causing each photon source 106 to emit light 118 having different time-varying intensity profiles). As another example, the oxygen sensor 102 can include an optical modulator (or multiple optical modulators), which can be optically coupled to each photon source 106 (or each optical modulator can be optically coupled to a respective photon source 106). In this way, the controller 104 can control the optical modulator so that the amplitude of the light 118 changes over time according to a wave as set by the optical modulator. Thus, in some cases, light emitted by a photon source 106 that has a substantially (i.e., deviating by less than 10% from) constant amplitude over time (e.g., by being driven by a substantially constant voltage value) can be modulated by the optical modulator to have an amplitude that changes over time according to a time-varying intensity profile. In some cases, each optical modulator can be an electro-optic modulator (e.g., controllable by the controller 104). In some cases, the amplitude of the light emitted from the photon source can be directly controlled by the photon source itself or an externally applied voltage or current. In some embodiments, the photon source(s) 106 can be implemented in different ways. For example, the photon source 106 can be a laser, a lamp (e.g., a halogen lamp), a light emitting diode ("LED") including an ultraviolet, visible, near-infrared light source, etc.

In some embodiments, the controller 104 (or the photon source(s) 106) can include a power source that can provide a driving signal to the photon source(s) 106. This driving source can be an AC power source. In this way, the light 118 emitted from a photon source 106 can follow the AC power source. In other words, the shape of the time-varying intensity profile of the light 118 can substantially correspond to the shape of the AC driving signal.

In some embodiments, the oxygen sensor 102 can include the optical filter 112 that can be optically coupled to the photon source(s) 106 (e.g., positioned in front of the photon source(s) 106). The optical filter 112 can block light in a wavelength range that includes the photoluminescent light emitted by the probe 110 (e.g., the light 120). For example, if the probe 110 emits light in a wavelength range of substantially 620 nm to substantially 750 nm, then the optical filter 112 can block light within this wavelength from passing through the filter 112 towards the probe 110 (e.g., to increase the signal to noise ratio by limiting the photodetector 108 from sensing light emitted by the photon source 106). In some cases, the optical filter 112 can be a band stop filter (e.g., a notch filter) having a stop band that is defined from substantially 500 nm to substantially 700 nm. In some cases, the photoluminescent material of the probe 110 can have a peak emission wavelength (e.g., being 645 nm) which can be positioned within the stop band of the optical filter 112 (e.g., when the optical filter 112 is a band stop filter). While the optical filter 112 is illustrated in FIG. 1 as being a single optical filter, in some cases, the optical filter 112 can define multiple optical filters, with each optical filter having a different optical density response (over various wavelengths). Thus, the multiple optical filters can collectively define the optical density response of the optical filter 112.

Similarly to the photon source(s) 106, the photodetector(s) 108 can include one or more photodetectors (e.g., one, two, three, four), and in some cases, the photodetector 108 can include a single photodetector. Each photodetector 108 can be optically coupled to the probe 110 and can be configured to receive the light 120 emitted by the probe 110 (e.g., in response to the excitation light that interacts with the photoluminescent material of the probe 110). For example, the probe 110 (e.g., and in particular the photoluminescent material of the probe 110) can interact with the light 118, and based on the interaction, can emit light 120, which can be at a lower energy level (e.g., higher wavelength) than the light 118. The light 120 can then be directed to the photodetector(s) 108, which can interact with the photodetector(s) 108 thereby generating optical data (e.g., the light 120 causing photocurrents to develop in the photodetector 108). This optical data can be received by the controller 104 and processed accordingly. In some embodiments, each photodetector 108 can be implemented in different ways. For example, the photodetector 108 can be an optical spectrometer, a spectrophotometer, a photodiode, an avalanche photodiode, a phototransistor, etc. In some configurations, the photodetector 108 being an avalanche photodiode can be advantageous in that the avalanche photodiode can be much more sensitive to receiving light than, for example, other photodiodes. For example, an avalanche photodiode can be orders of magnitude more sensitive to photon detection than some photodiodes.

In some embodiments, the sensor 102 can include the optical filter 114 optically coupled to the photodetector(s) 108, which can be implemented in a similar manner as the optical filter 112. For example, the optical filter 114 can be a single optical filter or can be multiple optical filters that form the optical filter 114. Regardless, the optical filter 114 can block light within a wavelength range that includes the light emitted by the photon source 106 (e.g., the light 118) from being received by the photodetector(s) 108. In some cases, the optical filter 114 can be a low pass filter with a cutoff frequency of substantially 450 nm. In some cases, the optical filter 114 can be a band pass filter with a pass band defined from substantially 400 nm to 1,000 nm or more specifically, from substantially 600 nm to substantially 850 nm. In some cases, the photoluminescent material of the probe 110 can have a peak emission wavelength that can be located within the pass band of the optical filter 114 (e.g., when the optical filter 114 is a band pass filter).

In some embodiments, the probe 110 can respond to changes in a parameter, variable, etc. For example, the parameter can be a concentration of an analyte, an oxygen partial pressure, pH, temperature, humidity, a concentration of a biomarker, a concentration of a gas, a concentration of molecular oxygen, a concentration of carbon dioxide, a concentration of nitric oxide, a concentration of a dissolved analyte in plasma (or tissue), etc. In some embodiments, the probe 110 can have a different lifetime value for different values of the parameter, variable, etc. For example, the probe 110 can emit the light 120 according to a Stern-Volmer curve that includes the parameter (e.g., on the x-axis) and the lifetime values (e.g., on the y-axis). In addition, the intensity of the light 120 can change with respect to changing the parameter. Thus, the intensity of the light 120 (e.g., an intensity value) can correspond to a parameter value. In other configurations, the time or phase difference of the time-varying intensity response (e.g. a temporal or phase value) can correspond to a parameter value.

In some specific configurations, the probe 110 can be implemented as an oxygen probe (e.g., an oxygen-sensitive probe), which is one non-limiting example of the probe 110. In this case, then the sensor 102 can be an oxygen sensor. And while the probe 110 can be implemented in different ways to, for example, respond to different variables, the following example describes the probe 110 as the oxygen probe that can sense different oxygen concentrations (e.g., an oxygen partial pressure). Thus, the probe 110 being implemented as an oxygen-sensitive probe pertains to other probes 110 each of which responding to a different variable. Continuing with this non-limiting example, the probe 110 can be configured to sense different molecular oxygen pressures (e.g., different oxygen partial pressure levels). For example, the probe 110 can include a photoluminescent material that can provide the photoluminescent property of the probe 110 (e.g., the photoluminescent material can respond differently to different oxygen partial pressure levels). As a more specific example, the photoluminescent material can be a phosphorescent material (e.g., a porphyrin, a metalloporphyrin) that can provide the phosphorescent property of the probe 110 (e.g., the phosphorescent material can respond differently to different oxygen partial pressure levels). In some cases, the probe 110 can include multiple different photoluminescent materials, or in particular, can include multiple different phosphorescent materials. In some cases, each photoluminescent material (or phosphorescent material) can have different oxygen diffusion rates or different quenching responses to the level of molecular oxygen (e.g., $O_2$). For example, each photoluminescent material (or phosphorescent material) can have a different sensing range for oxygen (e.g., having a different Stern-Volmer curve for different $O_2$ ranges). In some cases, a single material can contain different phosphorescent molecular components that each have different quenching response to the level of molecular oxygen (e.g., having a different Stern-Volmer curve for different $O_2$ ranges). As a more specific example, a polymer material can contain different phosphors whose quenching constants to oxygen in the material are all different. As another specific example, a material can contain multiple formulations of the same phosphor, with each formulation of the phosphor having different quenching responses (e.g. different Stern-Volmer curves).

In some embodiments, the probe 110, which can be oxygen sensitive, can emit different amounts of the light 120 in response to different percentages of molecular oxygen relative to other gases (e.g., different oxygen partial pressure levels) that are within the probe 110. For example, higher amounts of oxygen quench the photoluminescent material thereby leading to lower amounts of light 120 received. In some cases, the oxygen partial pressure level within the probe 110 can be based on a number of factors including the amount of oxygen in the ambient environment (e.g., that then diffuses into the probe 110), the amount of oxygen that diffuses through the tissue (e.g., assuming the probe 110 is in in communication with (e.g., in contact with, in gas communication with, in fluid communication, or otherwise acquiring information relative to the tissue), the amount of photoluminescent material, the temperature of the probe 110, etc. Thus, while the amount of light 120 can indicate the oxygen partial pressure (e.g., and the amount of oxygen diffusing through the tissue), using only amplitude-based measurements can be less accurate—especially over longer periods of time (as described above).

For example, the photoluminescent material can degrade over time (e.g., can undergo photobleaching) in which some of the photoluminescent materials (e.g., molecules) are no longer photoluminescent (e.g., no longer emit light in response to receiving light). This can lead to lower accuracy for oxygen sensing (e.g., the oxygen partial pressure being sensed to be higher than actual levels because of less light being emitted than expected), or this can lead to the need for frequent calibration to account for these phenomena when using intensity-based detection approaches. In some embodiments, however, the oxygen sensor system 100 can advantageously sense a parameter, such as oxygen levels (e.g., oxygen partial pressure levels), by relying on determining the photoluminescent lifetime of the probe 110, or information indicative of the photoluminescent lifetime (e.g., the phase of the time-varying intensity profile of the light 120, the time delay between the emission of the light 118 and the receiving of the light 120 from the photodetector 108, the time constant of the time-varying intensity profile of the light 120, etc.). In some configurations, this approach, rather than strictly intensity-based approaches can be advantageous in that this information can be relatively independent from the degradation of the photoluminescent material over time (e.g., some atoms of the photoluminescent material undergoing photo bleaching).

In some cases, because the physical dimensions of the probe 110 can impact the measurement of the desired analyte or parameter (e.g., oxygen tension), it can be important to limit the size of the probe 110 so that the probe can adequately respond quickly to changes in in an analyte or parameter, for example, oxygen partial pressure. continuing with this example, the oxygen-sensing material senses oxygen in tissue, for example, by having its oxygen levels equilibrate with that of the tissue it is in contact or proximity with. The larger the physical dimension of the oxygen-sensing material, the longer this equilibration process will take. In addition, the oxygen sensing material can contain (or retain) molecular oxygen, the release kinetics of which can be fast or slow. The larger the physical dimension of the oxygen sensor, the more oxygen in the material that must diffuse or leave to equilibrate. In other words, the larger the probe 110, the greater the equilibration time of the probe 110, and thus the slower the probe 110 measures oxygen.

Thus, by decreasing the size of the probe 110, the probe 110 can respond more quickly to changes in oxygen partial pressure levels, which can increase the oxygen sensing speed. For example, the probe 110 can have a volume less than 2 mm$^3$. As another example, the probe 110 can have a width less than 6 mm, a height less than 0.05 mm, a length less than 6 mm, etc.

As shown in FIG. 1, the probe 110 can be positioned partially (or entirely) within a zone 122 of the sensor 102, or in different configurations, can be positioned outside of the zone 122 (e.g., but in contact with, in gas communication with, in fluid communication with, or otherwise able to acquire information relative to the zone). The tissue 124 of a subject to be monitored can be positioned so that the zone 122 surrounds the tissue 124. For example, the sensor 102 can include a substrate that can define the zone 122. This substrate can be coupled to the subject (e.g., using an adhesive) so that the tissue 124 is positioned within the boundary of the substrate. The ideal situation is that the substrate covers the skin leaving no trapped air between the skin and the sensor 102 in the zone. In some cases, the material that defines the zone 122 can be semi-permeable to oxygen so that oxygen can diffuse into the zone 122 from the ambient environment (and vice versa). In this way, the tissue 124 is not completely blocked from oxygen diffusion from the air (e.g., which could damage the tissue 124), while at the same time the zone 122 is partially sealed from the ambient environment (e.g., so that the sensor 102 does not simply measure the oxygen partial pressure of the ambient environment). Thus, as described below, the sensor 102 can be calibrated to the oxygen permeability of the material that defines the zone 122, and the partial pressure of oxygen in the atmosphere. In other cases, the material that defines the zone can be impermeable to oxygen.

In some embodiments, the sensor system 100 can function as a transcutaneous oxygen monitor, and thus can sense oxygen partial pressures from the tissue 124, which can be skin. In other cases, however, the sensor system 100 can sense the oxygen level of other tissues. For example, the zone 122 can be omitted and the probe 110 can be inserted into the tissue 124 which can be muscle, blood, subcutaneous tissue (e.g., subcutaneous fat), etc. In some cases, the probe 110 can be inserted into an orifice of the subject, a blood vessel of a subject, etc. In other cases, the oxygen sensor system can be inserted or implanted within a region of tissue.

In some embodiments, the sensor system 100 can include one or more temperature sensors 116 (e.g., one, two, three, four, etc., temperature sensors). In some cases, a first temperature sensor 116 can be in thermal communication with the tissue 124. For example, the temperature sensor 116 can be positioned within the zone 122, can contact the tissue 124, can be coupled to (and in contact with) a material that defines the zone 122, can be coupled to (and in contact with) an optical fiber, etc. Regardless, the first temperature sensor 116 can sense the temperature of (or indicative of) the tissue 124, which can be used to compensate for changes in temperature that can impact the oxygen partial pressure levels sensed by the sensor 102. For example, as the temperature increases, the diffusion of oxygen also increases, and thus the sensed oxygen partial pressure can be higher (or lower) than expected (e.g., based on the temperature at which the sensor 102 was calibrated).

In some embodiments, the sensor system 100 can include a second temperature sensor that can be in thermal communication with a photon source 106. In some cases, the photon source 106 (e.g., when implemented as an LED) can experience changes in emitted amplitude, based on changes in the temperature of the LED. For example, at higher operating temperatures, the photon source 106 can have decreased light output (e.g., as opposed to the photon source 106 operating at lower temperatures).

In some embodiments, the sensor system 100 can include another temperature sensor that can be in thermal communication with the oxygen sensing material in the probe 110. This sensor can measure the temperature at which the molecular oxygen sensors reside, and therefore can serve to calculate the diffusion rate of oxygen and thus the temperature-dependent quenching rate of phosphorescence. Thus, temperature sensing from the temperature sensors can be used to compensate for the optical data received at the photodetector 108. For example, each amplitude of each intensity value, or each lifetime of each lifetime value, of the optical data can be adjusted based on the temperature value received by the temperature sensor. In alternative configurations, the sensor 102 can include a first photodetector 108 that is configured to receive light emitted by the probe 110, and a second photodetector 108 that is configured to receive light emitted from the photon source 106 so as to compensate for changes in temperature (or other conditions). In this configuration, because the light emitted by the photon source 106 is directly measured (e.g., and not estimated based on, for example, the electrical waveform applied to the photon source 106) the optical data generated by the photodetector 108 that is configured to receive light from the probe 110 does not need to be compensated with regards to the photon source (e.g., because the light input to excite the probe 110 is directly known).

In some embodiments, the controller 104 can be in communication with (e.g., bidirectional communication) some or all of the components of the oxygen sensor system 100, as appropriate, as well as a computing device 126 (e.g., a server, a wireless communication device including a smartphone, a tablet, a computer, etc.) and other computing devices. For example, the controller 104 can be in communication with the photon source(s) 106, the photodetector(s) 108, the temperature sensor(s) 116, etc. In this way, the controller 104 can transmit data to (e.g., instructions) and receive data from each of the components in communication with the controller 104. For example, the controller 104 can cause each photon source 106 to emit light, can receive optical data from each photodetector 108, and can receive temperature data from each temperature sensor 116.

In some embodiments, the controller 104 can transmit data to a computing device 126, which can be a wireless communication device (e.g., a smartphone). For example, the controller 104 can communicate with the computing device 126 according to a Bluetooth® wireless communication protocol to, for example, transmit data to (or receive data from) the computing device 126.

The controller 104 (e.g., an electronic controller) can be implemented in different ways. For example, the controller 104 can include typical components used such as a processor, memory, a display, inputs (e.g., a keyboard, a mouse, a graphical user interface, a touch-screen display, etc.), communication devices, etc. In some cases, the controller 104 can simply be implemented as a processor (e.g., a processor device). In other cases, the control 104 can be a microcontroller, a system-on-a-chip (SoC), or a system based on field-programmable gate arrays (FPGA). In some specific cases, the controller 104 can be a laptop computer, a desktop computer, a tablet, a smartphone, a stand-alone computer system, a server, a microcontroller, etc. Regardless of the configuration, the controller 104 can implement some or all of the processes described below, as appropriate.

In some embodiments, the controller 104 can include a display, while in other cases the display can be separate from the controller 104 (e.g., with the controller 104 in communication with the display). Regardless, however, the controller 104 can present information on the display, which can include the oxygen partial pressure levels, temperature data, optical data (e.g., the changing intensity values over time, the frequency information from the optical data, the optical spectrum of the optical data, etc.), phase information, results, etc. In some embodiments, the controller 104 can process, analyze, etc., the data received including the optical data, the temperature data, etc. For example, the controller 104 can determine frequency information from the optical data (e.g., through function fitting in the time domain, by applying a Fourier Transform to the optical data, a Fast Fourier Transform to the optical data, etc.). As another example, the controller 104 can digitally filter the optical data to, for example, isolate desired frequencies of interest.

In some embodiments, the controller 104 (or each photodetector 108) can include amplifiers (e.g., a transimpedance amplifier) with appropriate gains, regulators, etc., to facilitate appropriate receiving, modifying, etc., of the various sources of data. In addition, the controller 104 (or each photodetector 108) can include fixed or programmable electronic filters to isolate particular desired frequencies. In other embodiments, the controller 104 can include analog-to-digital converters for digitizer the signals received from elements of the oxygen sensing system. In this way, the controller 104 can utilize an algorithmic approach or technique to process the data and determine oxygen levels.

Figures 2A, 2B:
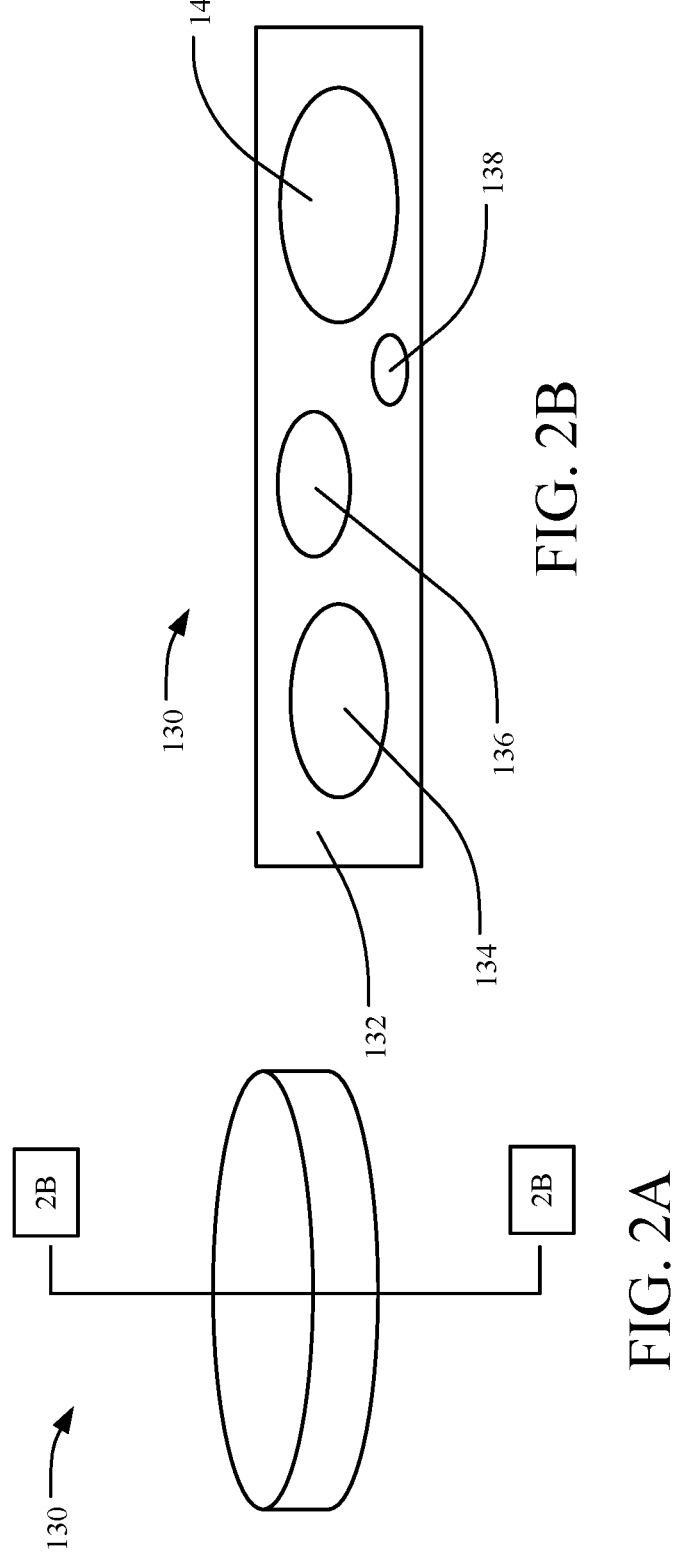
FIG. 2A shows a schematic illustration of a probe.
FIG. 2B shows a cross-sectional view of the probe of FIG. 2A taken along line 2B-2B of FIG. 2A.

FIG. 2A shows a schematic illustration of a probe 130, while FIG. 2B shows a cross-sectional view of the probe 130 taken along line 2B-2B of FIG. 2A. The probe 130 can be a specific implementation of the probe 110 and thus the probe 130 pertains to the probe 110 (and vice versa). As shown in FIG. 2A, the probe 130 is shaped as a cylinder with a radius and a thickness, however, the probe 130 can be shaped in different ways including, for example, being a cube, a prism, etc.

In some embodiments, the probe 130 can include a body 132, and photoluminescent regions 134, 136, 138, 140 coupled to or disposed within the body 132 (e.g., integrated within the body 132). Each photoluminescent region 134, 136, 138, 140 can include one or more photoluminescent materials, each of which can be a phosphorescent material. In some cases, each photoluminescent material (e.g., a porphyrin) can undergo quenching in response to the presence of an analyte (e.g., oxygen) and light (e.g., the light 118) that excites the photoluminescent material. Thus, each photoluminescent material can respond differently to different concentrations of an analyte such as oxygen. In some cases, each photoluminescent region 134, 136, 138, 140 can be tuned to different analyte sensing ranges. For example, each photoluminescent region 134, 136, 138, 140 can include a different photoluminescent material each of which has a different Stern-Volmer curve. In some configurations, each photoluminescent region 134, 136, 138, 140 can have a different peak emission wavelength (e.g., so optical data corresponding to the light emitted from each photoluminescent region 134, 136, 138, 140 can be separated from each other).

In other cases, each photoluminescent region 134, 136, 138, 140 can have substantially the same type and amount of photoluminescent material (e.g., the same porphyrin) and each region can have a different diffusion constant "K" with respect to the Stern-Volmer equation. Thus, even though each photoluminescent region 134, 136, 138, 140 can have the same type and amount of photoluminescent material, each photoluminescent region 134, 136, 138, 140 can have a different lifetime with respect to different concentrations of an analyte or parameter, such as oxygen. In this way, a combined response curve from a combination of the Stern-Volmer curves of the photoluminescent regions 134, 136, 138, 140 can have greater sensitivity and span a larger oxygen partial pressure range as compared to a single region. Thus, the changes in phase difference (e.g., between two time-varying intensity profiles) can be equally sensitive through a larger oxygen partial pressure than a single region alone (e.g., as compared to a single photoluminescent region). In some cases, to yield the different diffusion constants for each photoluminescent region 134, 136, 138, 140, each photoluminescent region 134, 136, 138, 140 can be encapsulated by a layer of a semi-permeable material (e.g., a polymer) of different thicknesses, which can act as a diffusion resistor (e.g., thicker layers yielding larger diffusion constants). For example, each photoluminescent region 134, 136, 138, 140 can have substantially the same volume (and concentration) of the photoluminescent material (e.g., which can be integrated within a material such as a polymer). This volume of photoluminescent material can be encapsulated by a layer of a semi-permeable material, in which the thickness of the layer can dictate the diffusion constant (e.g., a larger thickness increasing the diffusion constant and vice versa). This then can result in each photoluminescent region 134, 136, 138, 140 having a different Stern-Volmer curve.

In some embodiments, each photoluminescent region 134, 136, 138, 140, and in particular the photoluminescent material within each region, can be excited by a different wavelength of light. In this way, for example, each photon source can selectively excite one of the photoluminescent regions 134, 136, 138, 140, thereby selecting which photoluminescent region 134, 136, 138, 140 to receive optical data from. In other configurations, each photoluminescent region 134, 136, 138, 140, and in particular, the photoluminescent material within each region, can be excited by a same wavelength (or can be excited by the light 118, which can include multiple wavelengths), and each can emit respective light having a different wavelength. In this way, a controller can receive optical data from a photodetector that is configured to receive light emitted from a respective region 134, 136, 138, 140, with receiving minimal (to no) light emitted from a different region. In other words, each photodetector can include a respective optical filter that is configured to allow light emitted from one region 134, 136, 138, 140, while blocking light from passing through to the detector from the other regions 134, 136, 138, 140 (e.g. the other three regions). In other configurations, the photoluminescent material in different regions excited by the same wavelength can emit respective light all having the same wavelength where the photoluminescent materials each have different response lifetimes, such as illustrated in FIG. 3. In this way, a controller can receive optical data from a photodetector configured to receive light from all regions but can distinguish the signal and parameters encoded from each region via those regions' unique lifetimes.

In some configurations, each photoluminescent region 134, 136, 138, 140, and in particular each photoluminescent material, can be configured to respond to changes in a different analyte. For example, the photoluminescent region 134 can respond to changes in partial oxygen levels, the photoluminescent region 136 can respond to changes in pH, the photoluminescent region 138 can respond to changes in an analyte (e.g., a different analyte), etc.

In another embodiment, the body 132 contains a number of phosphors whose molecular characteristics are each different so as to produce sufficiently different lifetimes or quenching constants in response to an analyte, such as oxygen. As a non-limiting example, oxygen will be described as the analyte. Unlike described above, in this embodiment, the phosphorescent molecules can be equally spread throughout the body 132; it is their individual molecular characteristics that provide the range of lifetimes or quenching constants to yield oxygenation data that corresponds to a larger oxygen partial pressure than a single phosphor alone. The molecular characteristics that define the phosphor quenching constants can include the structure and composition of the phosphor (e.g. different molecular structure), different inserted metal (e.g. platinum vs palladium), different peripheral or decorating groups (e.g. bare porphyrin vs porphyrin dendrimer). These different characteristics are listed as examples and do not constitute all possible molecular characteristics that could be used to create different lifetimes, quenching rates, quenching constant responses to oxygen. A photoluminescent material configured in this way can be excited by the same wavelength and each phosphor can emit respective light all having the same wavelength; the materials each have different response lifetimes, analyte diffusion rates, or quenching constants. In this way, a controller can receive optical data from a photodetector configured to receive light from all phosphors, but can distinguish the signal and parameters encoded from each phosphor via those phosphors' unique lifetimes.

Figures 3A, 3B:
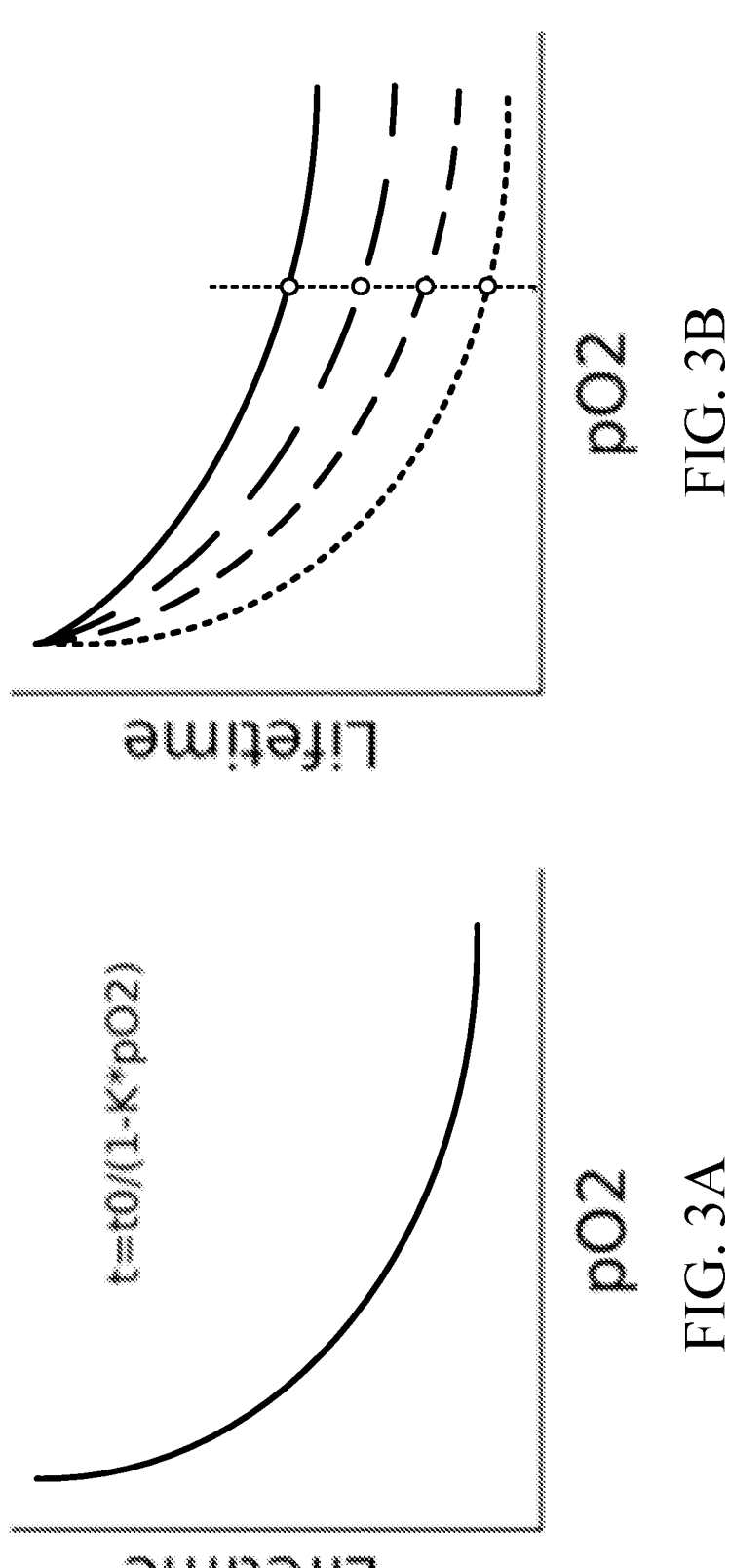
FIG. 3A shows a graph of an example of a Stern-Volmer curve that corresponds to a single photoluminescent region having a single type of photoluminescent material.
FIG. 3B shows a graph of multiple Stern-Volmer curves, each of which corresponds to a photoluminescent region having a different diffusion constant.

FIG. 3A shows a graph of an example of a Stern-Volmer curve that corresponds to a single photoluminescent region having a single type of photoluminescent material. As shown in FIG. 3A, there is a single curve. FIG. 3B shows a graph of multiple Stern-Volmer curves, each of which corresponds to a photoluminescent region having a different diffusion or quenching constant, or different photolumiphor having a different diffusion or quenching constant. As shown in FIG. 3B, each of the Stern-Volmer curves are shifted along the vertical axis (e.g., the life-time axis). While not shown in FIG. 3B, each of the Stern-Volmer curves of FIG. 3B intercept the oxygen partial pressure axis at different locations (e.g., each of the Stern-Volmer curves have different x-intercepts). The sensitivity to changes in oxygen concentration highest when the lifetime changes with oxygen concentration are the greatest. Therefore, in FIG. 3A, the sensitivity of the example system would be greatest at low oxygen when the curvature change is high and low when the exponential curve is flat. By having multiple Stern-Volmer responses in a single sensor as in FIG. 3B, the sensitivity of the oxygen sensing system is improved over a larger range, this range arising from the analysis of each individual response curve together.

In some embodiments, because the lifetime is related to the time constant of the phosphorescence decay (e.g. after an excitation delta or square pulse), the phase difference (e.g. after excitation sinusoidal pulse), then if the time constant or the phase difference is determined, the oxygen partial pressure can be determined (e.g., via the Stern-Volmer curve).

In other embodiments, the measured lifetime response of an oxygen sensing system can be measured as a function of oxygen concentration. As the measured lifetime of a single or multiple phosphors or phosphorescent regions are dependent on oxygen concentration, these oxygen lifetime responses can be recorded as a look-up-table. This look-up-table can then be used such that a set of measured lifetimes by the oxygen sensing system gives a measure of oxygen concentration. In yet other embodiments, the measured lifetime response of an oxygen sensing system can be measured as a function of oxygen concentration to generate an empirical equation. This empirical equation can then be used such that a set of measured lifetimes by the oxygen sensing system gives a measure of oxygen concentration. In still yet other embodiments, the measured lifetime response of an oxygen sensing system can be measured as a function of oxygen concentration to train a machine learning model. This machine learning model can then be used such that a set of measured lifetimes by the oxygen sensing system gives a measure of oxygen concentration.

Figures 4, 5:
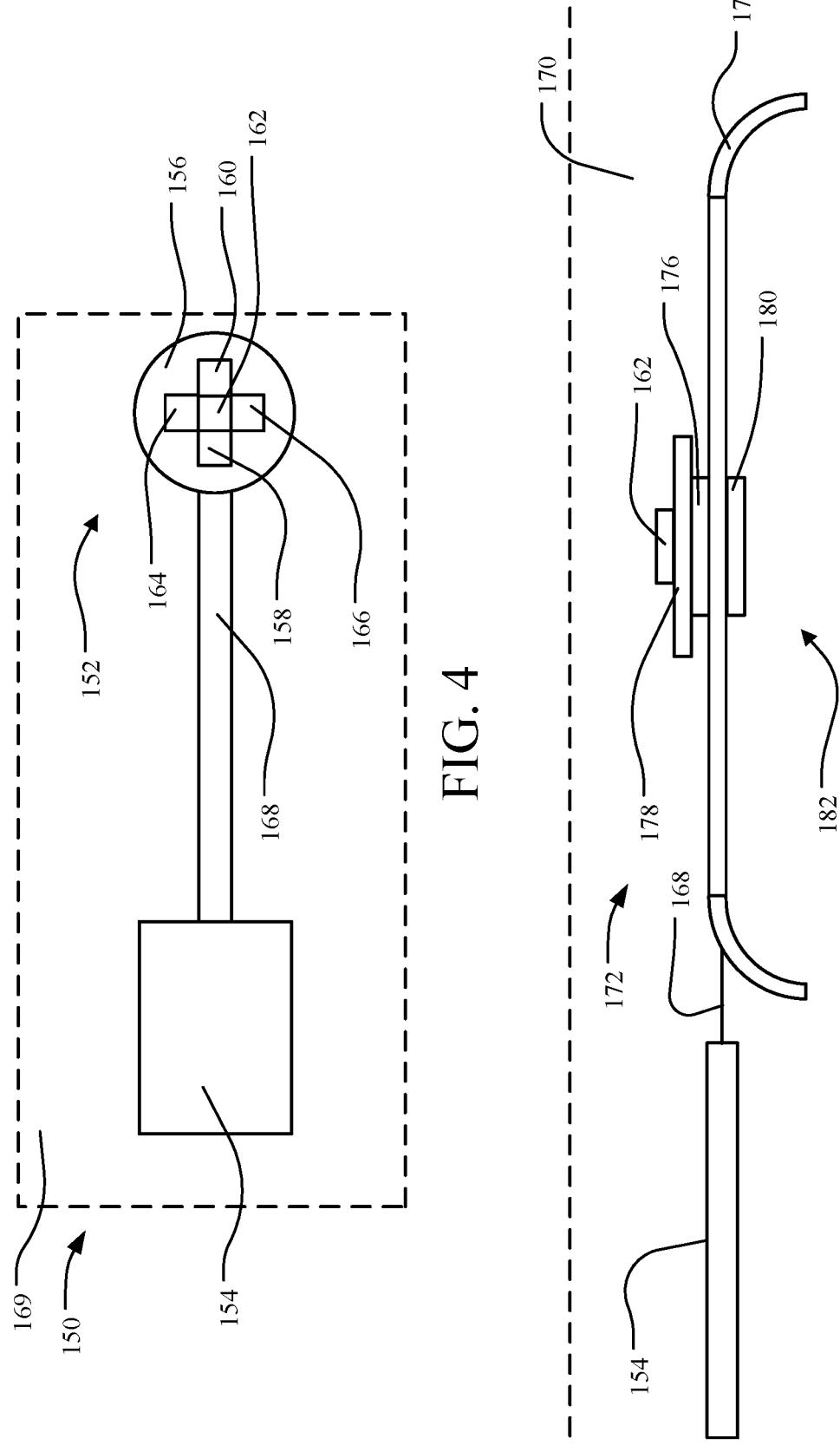
FIG. 4 shows a schematic illustration of another sensor system.
FIG. 5 shows a cross-sectional view of a substrate of the sensor system of FIG. 4, with portions of the sensor head of the sensor system removed for visual clarity.

FIG. 4 shows a schematic illustration of an oxygen sensor system 150. The oxygen sensor system 150 can be a specific implementation of the oxygen sensor system 100 and thus the oxygen sensor system 100 pertains to the oxygen sensor system 150 (and vice versa). As shown in FIG. 4, the oxygen sensor system 150 can include an oxygen sensor 152, and a controller 154. The oxygen sensor 152 can include a sensor head 156, which can include photon sources 158, 160, photodetectors 162, 164, and a temperature sensor 166. In some cases, the photodetector 162 can be positioned between the photon sources 158, 160, which can be advantageous in that the photodetector 162 can be shielded from ambient light (e.g., which would decrease the signal to noise ratio). In some configurations, the photodetector 164 can be positioned above (or below) the photon sources 158, 160. In some cases, the photodetector 162 can be configured to sense light emitted from an probe, while the photodetector 164 can be configured to sense light emitted from each photon source 158, 160.

In some embodiments, the oxygen sensor system 150 can include an electrical cable 168 that electrically connects components of the sensor head 156 to the controller 154. For example, one end of the electrical cable 168 can be electrically connected to the photon sources 158, 160, the photodetectors 162, 164, and the temperature sensor 166, while the other end of the electrical cable 168 can be electrically connected to the controller 154. In some cases, the electrical cable 168 can include one or more electrical wires, with each electrical wire being configured to be electrically connected to a respective one of the photon sources 158, 160, the photodetectors 162, 164, or the temperature sensor 166 at one end and to the controller 154 at an opposing end (e.g., via a pin of the controller 154). In other cases, the electrical cable 168 can communicate via serial interface between the sensor and controller. In some cases, the electrical cable 168 allows the sensor head 156 (and thus the oxygen sensing capabilities) to be positioned at different locations relative to the controller 154, which can have larger dimensions than the sensor head (e.g., harder to anchor to the subject). For example, the sensor head 156 can be oriented to different positions and orientations relative to the controller 154 via the electrical cable 168 (e.g., because the electrical cable 168 is flexible), including, for example, the back of the subject, the shoulders of the subject, etc. In some specific cases, the electrical cable can be a ribbon cable. In other embodiments, the entire oxygen sensor 150 can be contained in a single housing, with the sensor head 156 and controller 154 being part of the same physical device. In such an embodiment, the sensor head 156 and controller 154 may share physical components (e.g. may both be constructed from the same circuit board 169) such that the electrical cable 168 is simply a trace on the circuit board 169.

Alternatively, referring to FIG. 5, in some embodiments, the oxygen sensor system 100 can include a housing 170 and a substrate 172. The housing 170 can be coupled to the controller 154, which can support the controller 154. In some cases, although not shown in FIG. 4 or 5, the oxygen sensor system 100 can include a band, strap, etc., coupled to the housing 170 to secure the housing 170 relative to an appendage (e.g., arm, a leg, a wrist, etc.) or other portion of the body of the subject. In some cases, the band, strap, etc., can be adjustable to accommodate for different sized portions of the subject. For example, the housing 170 can include a clap, a clip, etc., to be removably coupled to the band, strap, etc., to accommodate different sizes. In some cases, then, the housing 170 can be secured in a similar manner as a watch (or other wearable electronic device). In some cases, the housing can be fabricated from flexible materials, e.g., silicone, and be adhered to the subject as an adhesive patch. In other cases, the housing 170 may also surround the substrate 172 to form part of the same unit, as illustrated in FIG. 5.

In some embodiments, the substrate 172 can be coupled to the sensor head 156 and can be engaged with a subject to provide a seal between the substrate 172 and the tissue of the subject. The substrate can include multiple layers. For example, the substrate 172 can include layers 174, 176, 178, 180, which are represented in the cross-sectional view of the substrate 172 in FIG. 5. The layer 174 semi-permeable to oxygen diffusion therethrough, and can be a sheet of material, which can allow the layer 174 to be flexible to conform to different surfaces of the subject. While the layer 174 is illustrated in FIG. 4 as being a square, the layer 174 can have other shapes including, for example, a circle, and oval, etc. In some configurations, the layer 174 can include an adhesive layer positioned on an outer surface of the layer 174 (e.g., the surface that faces the tissue when the substrate 172 is engaged with the subject). In some cases, this adhesive layer can span partially or entirely along the outer surface of the layer 174. For example, the adhesive layer can span a region proximal to the peripheral edge of the layer 174. In some cases, the layer 174 can have a scattering, reflective or light absorbing layer coupled to the inner surface of the layer 174 (or the outer surface of the layer 174), which can face the ambient environment. In this way, the reflecting layer can reflect away or absorb ambient light that could otherwise undesirably interact with the probe.

The layer 176 which can be situated between the layers 174 and 178 can be an probe, which has been described previously. In some cases, the positioning of the layer 176 (e.g., the sandwiching of the layer 176) can isolate the layer 176 and thus the probe from directly contacting the patient. In this way, undesirable materials that could leach from the probe are advantageously blocked from contact with the patient. The layer 178 can be positioned above the layer 176 and on the sides of the layer 176 so that layer 178 blocks atmosphere on the top and the sides of layer 176 and most of the O$_2$ sensed comes through the layer 174 from the skin. The layer 178 can be formed out of a material that is less permeable to oxygen than the layer 174. In this way, the oxygen from the ambient environment passing through the layer 178 and into the probe (e.g., the layer 176) is kept low to allow for more accurate oxygen partial pressure measurements of the zone 182 (e.g., so that external oxygen is not diffusing into the probe that does not originate from the zone 182). The layer 178 can allow light to pass through including light from each of the photon sources 158, 160, and light emitted by the probe. Thus, the layer 178 can be transparent.

In some embodiments, the layer 180 can be positioned below the layer 174 (e.g., coupled to the layer 174), and can be configured to scatter light directed at the layer 180, while blocking light from passing through the layer 180. Thus, for example, the layer 180 can be defined as a light scattering or light reflecting layer. In some cases, the layer 180 can be aligned with the photodetector 162, which can be advantageous in any ambient light (e.g., originating from the zone 182) is blocked from passing directly through the layer 180 and to the photodetector 162. Rather, the ambient light is scattered or reflected after being directed at the layer 180. The luminescence of the oxygen sensing layer 176 is emitted in all directions such that light directed towards the tissue (zone 182) may pass into the tissue and not be detected. The scattering or reflective nature of layer 180 acts to redirect a portion of this otherwise lost emitted light back towards the photodetector 162 to be detected. In one non-limiting example, the layer 180 may include Mylar to be reflective. In another non-limiting example, the layer 180 may include white, for example, silicones, to provide functional scattering. Thus, a higher proportion of light emitted by the probe can be directed to the photodetector 162 as compared to without layer 180, and ambient light is blocked, thereby improving the total signal collected as well as the signal to noise ratio. In some cases, the width of the layer 180 can be larger than the width of the photodetector 162 to ensure that ambient light near the periphery of the layer 180 is not directed at the photodetector 162. In some cases, the photon sources 158, 160, and the photodetectors 162, 164 can each be aligned with the layer 180. In some configurations, the layer 180 can block light from the zone 182 from reaching each photodetector 162, 164, and can block light from each photon source 158, 160 from reaching the zone 182. In some configurations, the layer 180 can be configured to specifically reflect or scatter the luminescence of the oxygen sensing layer.

In some embodiments, while each layer 174, 176, 178, 180 of the substrate 172 is shown being coupled together as illustrated in FIG. 5. In other configurations, the layers 174, 176, 178, 180 can be structured differently. For example, the layer 176 can be integrated within the layer 174, or can be integrated within the layer 178. In addition, the layer 176 can be partially (or fully) encapsulated by the layers 174, 176.

As shown in FIG. 5, the substrate 172 (and in particular the layer 174) can define the zone 182, which can be in communication with, including direct contact or fluid communication, with a tissue of the subject (e.g., in which the substrate 172 is engaged with). The zone 182 is at least partially sealed from the ambient environment (e.g., the area surrounding the substrate 172), and oxygen can diffuse through the layer 174 and into the zone 182 (and vice versa) according to the diffusion characteristics of the layer 174. In addition, oxygen from the tissue can diffuse into (or out of) the zone 182. Thus, oxygen that diffuses into the probe (and sensed by the probe) can partially originate from the tissues, which can then be used to determine the oxygen partial pressure of the tissue. In some embodiments, the temperature sensor 166 can be in thermal communication with the substrate 172, and in particular, the layer 174. In this way, the temperature data from the temperature sensor 166 can be indicative of the temperature of the zone 182 (and thus the oxygen therein), which can then be used to compensate for changes in temperature.

Figure 6:
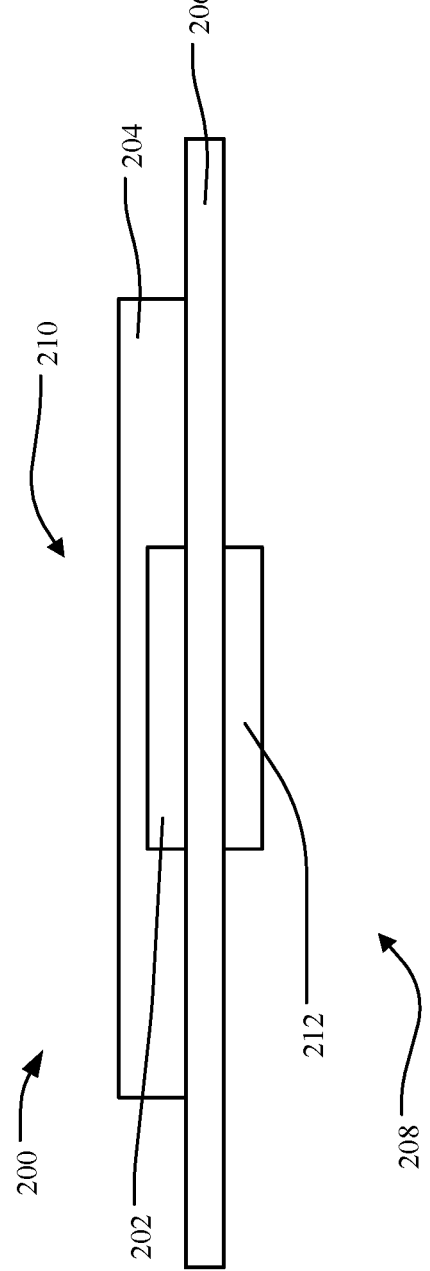
FIG. 6 shows a cross-sectional view of another substrate.

FIG. 6 shows a cross-sectional view of a substrate 200, which can be similar to the substrate 172. Thus, the substrate 200 can be implemented with the oxygen sensor system 150. The substrate 200 can include layers 202, 204, 206. As shown in FIG. 6, the layer 202, which can be a probe that can be integrated within the layer 204. In other cases, the layer 202 can be nested within the layer 204. For example, the layer 204 can include a cavity and the layer 202 can be inserted within the cavity. In some cases, an outer surface of the layer 202 can be flush with the outer surface of the layer 204, which is illustrated in FIG. 6. In some cases, the layer 204 can be semi-permeable to oxygen diffusion therethrough or substantially impermeable to oxygen diffusion therethrough. Regardless of the configuration, the layer 202 can be enclosed by the layer 204 so that oxygen diffusion from the ambient environment through the layer 204 and into the layer 202 is reduced. In some cases, similarly to the layer 178, light from a photon source and from the probe can pass through the layer 204. Thus, the layer 204 can be transparent.

In some embodiments, the layer 206 can be positioned below the layer 202 (and can be coupled to the layer 206). The layer 206 can be semi-permeable to oxygen diffusion therethrough, and can be more permeable to oxygen diffusion therethrough. In this way, the layer 202 receives a larger amount of oxygen from the side 208, as opposed to the side 210. In some configurations, the layer 206 can scatter or reflect ambient light that is directed at the layer 206, which can prevent the ambient light from reaching a photodetector (e.g., that could decrease the signal to noise ratio). In some configurations, the substrate 200 can include a layer 212 positioned below the layer 206 (and coupled to the layer 206), which can reflect or scatter light that is directed at the layer 212.

Figures 7A, 7B:
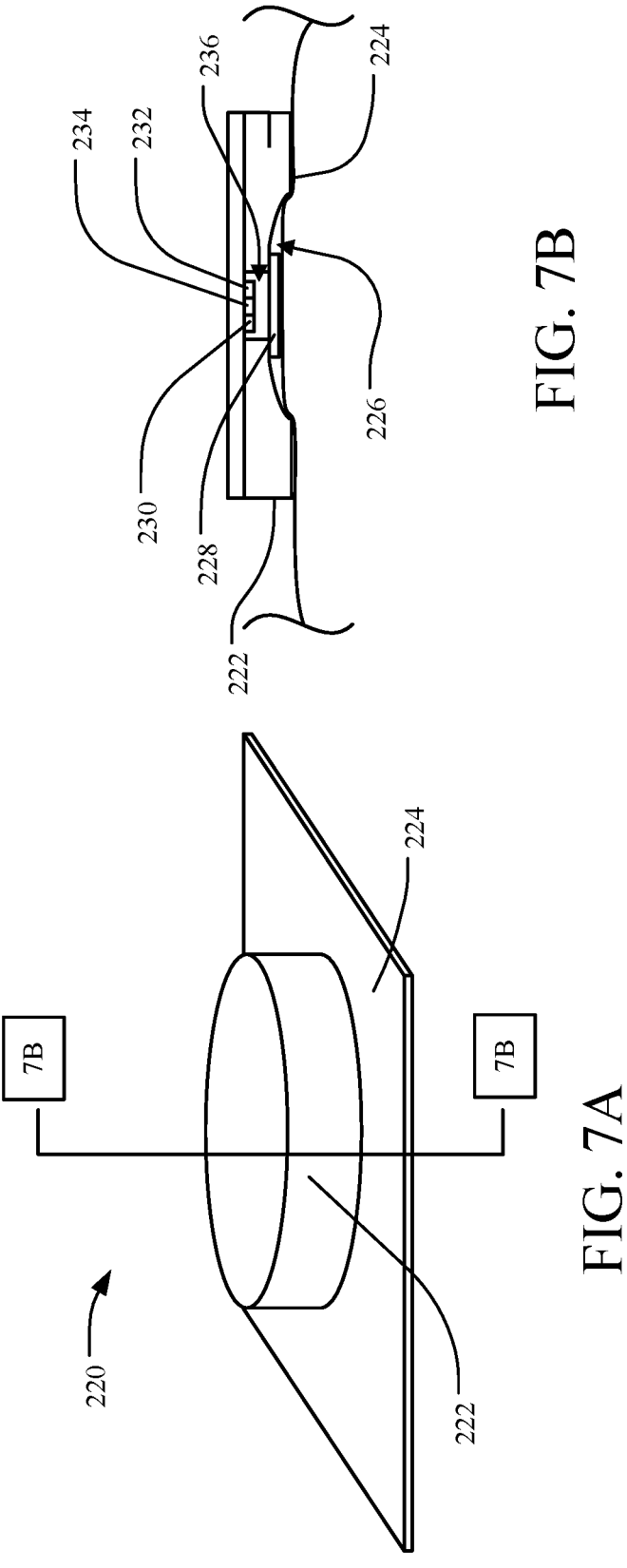
FIG. 7A shows a schematic illustration of another sensor head.
FIG. 7B shows a cross-sectional view of the sensor head of FIG. 7A taken along line 7B-7B of FIG. 7A.

FIG. 7A shows a schematic illustration of a sensor head 220, which can be similar to the sensor head 156 of the oxygen sensor system 150. Thus, the sensor head 156 can be replaced with the sensor head 220, or can be integrated within a different oxygen sensor system described herein. As shown in FIG. 220, the sensor head 220 can include a housing 222 that is configured to engage with a tissue 224 of the subject.

FIG. 7B shows a cross-sectional view of the sensor head 220 taken along line 7B-7B of FIG. 7A. As shown in FIG. 7B, the housing 222 can define a zone 226, which can be in contact with, gas communication with, fluid communication with, or otherwise proximate to the tissue 224. In addition, the housing 222 can engage the tissue 224 so that the housing 222 (temporarily) seals with the tissue 224 thereby (partially) isolating the zone 226 from the ambient environment. In some cases, the housing 222 can be semi-permeable to oxygen diffusion therethrough. For example, although not shown, the housing 222 can include one or more channels directed though the housing 222 (e.g., microchannels). In some embodiments, the sensor head 220 can include a probe 228 that can be in contact, gas communication, or fluid communication with the zone 226, which is designed to receive the tissue 224, preferably, to avoid forming a void. To this end, the zone 226 may present probe 228 without any recess. For example, the probe 228 can be positioned within the zone 226 and can be coupled to the housing 222.

In some cases, the sensor head 220 can include photon sources 230, 232, and a photodetector 234 optically coupled to the probe 228. For example, as shown in FIG. 7B, each photon source 230, 232, and the photodetector 234 can be positioned within a recess 236 of the housing 222 that is in contact with, gas communication with, or fluid communication with the probe 228. In this way, the photodetector 234 can be shielded from the ambient light by the housing 222. In addition, the housing 222 can block light from passing from the ambient environment and into the zone 226.

Figure 8:
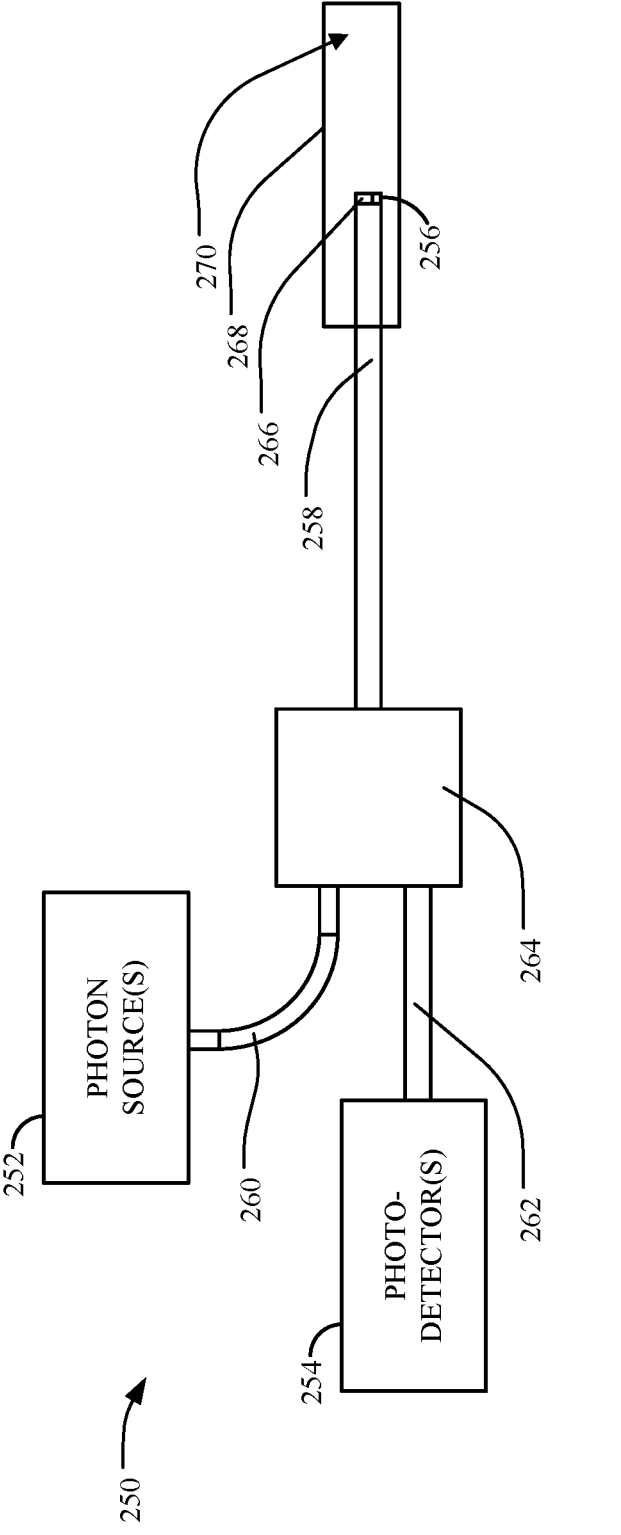
FIG. 8 shows a schematic illustration of a block diagram of another sensor system.

FIG. 8 shows a schematic illustration of a block diagram of an oxygen sensor system 250, which can be a specific implementation of the oxygen sensor system 100. Thus, the oxygen sensor system 100 pertains to the oxygen sensor system 250 (and vice versa). As shown in FIG. 8, the oxygen sensor system 250 can include photon source(s) 252, photodetector(s) 254, temperature sensor(s) 256, optical fibers 258, 260, 262, a tree coupler 264, and a probe 266. The probe 266 can be optically coupled to the optical fiber 258. For example, the probe 266 can be coupled to an end of the optical fiber 258. In some cases, the probe 266 can be a coating that is disposed on the optical fiber 258.

In some embodiments, an opposing end of the optical fiber 258 can be coupled to an output of the tree coupler 264. Correspondingly, one end of the optical fiber 260 can be coupled to a first input of the tree coupler 264, and an opposing end of the optical fiber 260 can be optically coupled to the photon source(s) 252. In addition, one end of the optical fiber 262 can be coupled to a second input of the tree coupler 264 and an opposing end of the optical fiber 262 can be optically coupled to the photodetector(s) 254. In this way, light from the photon source 252 can be emitted into the optical fiber 260, which can travel through the fiber 260, through the tree coupler 264, through the optical fiber 258, and can be directed at the probe 266 (e.g., to excite the probe 266). Correspondingly, light emitted from the probe 266 (e.g., in response to the light from the photon source(s) 252) can travel back through the optical fiber 258, through the tree coupler 264, through the optical fiber 262 and to the photodetector(s) 254.

In some embodiments, a temperature sensor 256 can be in thermal communication with the probe 266, and thus temperature data from the temperature sensor 256 can be indicative of the temperature of the environment in which the probe 266 is positioned. For example, the temperature sensor can be thermal communication with the probe 266 at the distal fiber tip. In another example, the temperature sensor 256 can be in thermal communication with the optical fiber 258. In other cases, the temperature sensor 256 can be in thermal communication with a tissue proximal to the probe 266. For example, the temperature sensor 256 can be positioned within the subject proximal the tissue.

In some embodiments, the optical fiber 258 is configured to be inserted into a channel 270 of a medical instrument 268. For example, the diameter (or width) of the channel 270 of the medical instrument 268 can be less than 500 μm, and the optical fiber 258 can be less than the diameter of the channel 270 (e.g., the diameter of the optical fiber 258 being less than or equal to 200 μm). In some cases, the optical fiber 258 can be advanced through the channel 270 until a portion (or the entire) probe 266 is positioned out of the channel 270 (e.g., a distal end of the channel 270). In some configurations, the medical instrument can be a syringe having a needle, a catheter, etc. In other cases, the medical instrument can be an endoscope and the channel 270 can be the working channel of the endoscope.

While the oxygen sensor system 250 has been illustrated as having one probe 266, in other configurations, the oxygen sensor system 250 can include multiple probes, each disposed at different longitudinal positions along the optical fiber 258. In some cases, the optical fiber 258 can include a crack, score, etc., at each longitudinal location of an probe 266 to ensure light is emitted to and received from the respective prove 266.

In some configurations, the probe 266 can be formed of multiple layers. For example, a first layer can be coupled to the optical fiber 258, a second layer can be coupled to the first layer, and so on, to form the probe 266. Each layer can include a photoluminescent material. This construction can yield a thin film for the probe 266, which can significantly decrease the size of the probe 266, thereby significantly increasing oxygen sensing speed (e.g., the probe responding quickly to changes in oxygen partial pressures).

In some configurations, the probe 266 can be coupled to the medical device 268. For example, an probe 266, and the optical fiber 258 can be inserted into the channel 270 of the medical device 268 and coupled to the medical device 268 within the channel 270 (e.g., via using an epoxy, adhesive, etc.). In this way, such as when the medical device 268 is a needle, the needle can be inserted directly into the subject (e.g., at a muscle region of the subject) without requiring the probe 266 to then be deployed into the medical device 268 thereby saving time. In another example, the optical fiber can be inserted or re-inserted repeatedly into the medical device 268 after the medical device has been inserted into the patient. In this way, the probe can be used at specific times or when needed.

While the oxygen sensor system 250 has been illustrated as having two optical fibers 260, 262, in other configurations, the oxygen sensor system 205 can include additional optical fibers, each coupled to a respective input of the tree coupler 264. Then, an opposing end each optical fiber can be optically coupled to a photon source 252 or a photodetector 254.

Figure 9:
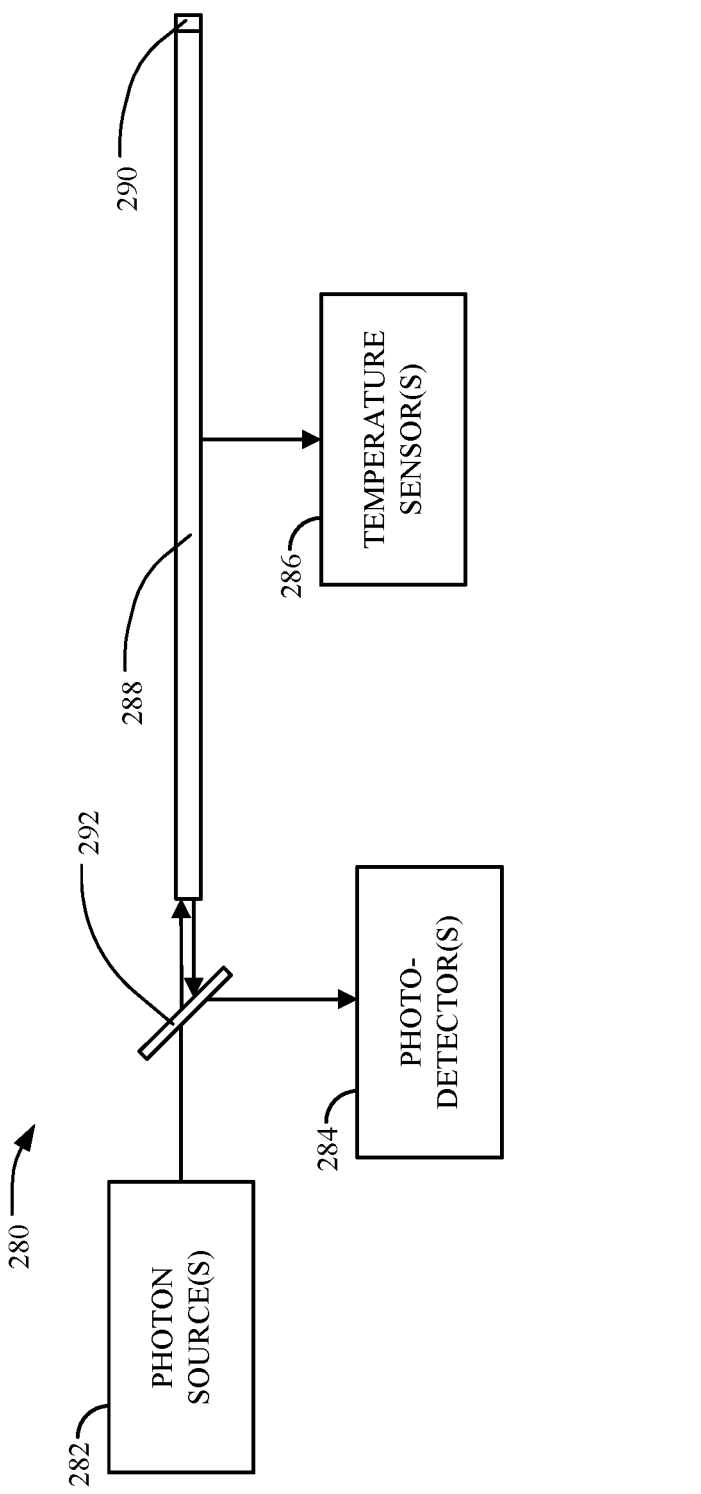
FIG. 9 shows a schematic illustration of a block diagram of sensor system.

FIG. 9 shows a schematic illustration of a block diagram of an oxygen sensor system 280, which can be a specific implementation of the oxygen sensor system 100. Thus, the oxygen sensor system 100 pertains to the oxygen sensor system 280 (and vice versa). As shown in FIG. 9, the oxygen sensor system 280 can include photon source(s) 282, photodetector(s) 284, temperature sensor(s) 286, an optical fiber 288, a probe 290, and a beam splitter 292. As shown in FIG. 9, light emitted from the photon source(s) 282 passes through the beam splitter 292, into the optical fiber 288, though the optical fiber 288, and is directed to the probe 290 (e.g., to excite the probe 290). Correspondingly, light emitted from the probe 290 is emitted back into the optical fiber 288, travels through the optical fiber 288, is directed by the beam splitter 292 to the photodetector(s) 284.

Figure 10:
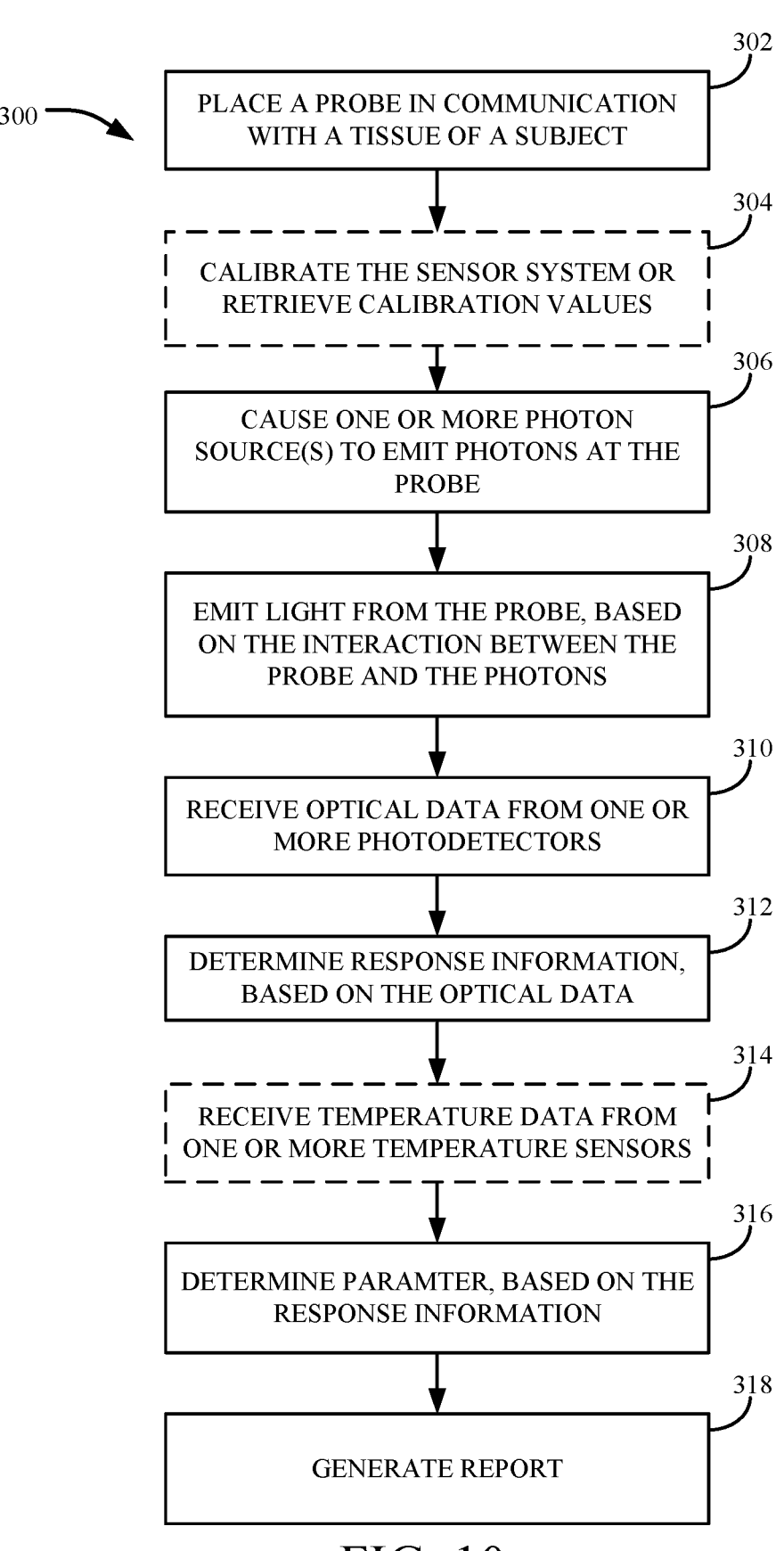
FIG. 10 shows a flowchart of a process for monitoring a subject in accordance with the present disclosure.

FIG. 10 shows a flowchart of a process 300 for monitoring a patient in accordance with the present disclosure. At 302, the process 300 can include placing a probe in communication with tissue of a subject. As used herein, in communication may include being in contact with, in gas communication with, in fluid communication with, or otherwise positioned to acquire information relative to a tissue of a subject. For example, this can include coupling a substrate that includes the probe to skin of the subject. As another example, including when the probe is coupled to an optical fiber and the optical fiber (including the probe) is inserted into a medical device (e.g., a catheter, a needle, etc.), the medical device can be inserted into the subject (e.g., into the muscle, into an orifice, into a lumen, etc., of the subject). As described above, the probe can include multiple probes with respective operational ranges and configured to be excited based on respective signals.

At 304, the process 300 can optionally include a computing device calibrating a sensor system, or receiving calibration value(s) (e.g., from the memory of the computing device). In some cases, this can include a computing device receiving a calibration curve, based on, for example, temperature data (e.g., a temperature response curve versus analyte concentration). In some cases, the calibration curve can be a Stern-Volmer curve. A calibration procedure will be described in more detail below.

At 306, the process 300 can include an analog or computing device causing one or more photon sources to emit photons. This may be achieved by creating a time-varying profile that, in total, is designed to excite the probe. As mentioned above, the probe may include multiple probes or probe components or zones with respective operational characteristics or operational ranges and that are configured to be exited based on respective signals. To this end, the time-varying profile may be formed by combining two or more sub-signals, where each sub-signal is designed to excite respective ones of the multiple probe components or zones.

For example, the respective time-varying profile may have a time-varying intensity (e.g., the total intensity of light emitted by a photon source may change over time) and be composed from respective sub-signals that are of different frequencies, where each frequency is designed to target one of the multiple probe components or zones. In one non-limiting example, the computing device may cause a first photon source to emit photons according to a first sub-signal, and cause a second photon source to emit photons according to a second sub-signal, to thereby excite two of the multiple probe components or zones. Thus, in some cases, each time-varying intensity profile can be periodic and can include multiple frequencies. For example, the time-varying intensity profile can be a sum of sinusoids (e.g., multiple different sine waves each corresponding to a different sub-signal configured to excite a respective probe component or zone) and, thus, the time-varying intensity profile can have multiple different frequencies.

Creating a time-varying profile from sub-signals having different respective frequencies is but one non-limiting example. In some cases, the time-varying profile can be non-periodic. For example, the time-varying profile can be an impulse (or in other words a delta function), a pulse (e.g., a square pulse, a rectangular pulse, etc.), or the like.

Additionally, the time-varying profile and/or the sub-signals may be varied over time. For example, the time-varying profile can be changed over time, for example in response to changes in the measured oxygen concentration. This change could include alterations to the waveform to, for example, modify the fundamental frequency, or add or subtract sine waves, which could be used to dynamically alter the sensitivity, accuracy, precision, operational range, or functionality, for example of the multiple probe components or zones and, thereby, to adjust the overall sensitivity, accuracy, precision, operational range, or functionality of the of the overall sensing system. This feedback control method can be used to optimize overall functionality of the sensor for a given range, for example, a range of oxygen concentrations.

Once the photon source(s) are emitting light based on the time-varying profile (and, thus, the sub-signal used to form the time-varying profile), at 308, the probe is excited. In the non-limiting example of a probe designed to monitor an analyte and the non-limiting example of oxygen as an analyte, the interaction between the oxygen-sensitive-probe and the photons from the one or more photon sources will cause the probe to emit light. In this case, the light emitted from the probe will have a time-varying profile, which can correspond to the time-varying profile of the photons emitted from the one or more photon sources (e.g., at the block 306) at least because the photons from the probe excite the probe thereby causing the probe to emit the light. In this way, the source operates according to a first time-varying profile and the probe emits light according to a second time-varying profile. In some cases, the light emitted by the probe can have a larger wavelength than a wavelength of the photons emitted from the one or more photon source. For example, a wavelength of light emitted from the probe can be in the red-light visible range, while a wavelength of a photon emitted from the one or more photon sources can be in the blue light visible range (or the ultraviolet range).

At 310, the process 300 can include a computing device receiving optical data from one or more photodetectors based on the interaction between the light emitted from the probe and the one or more photodetectors. In some cases, the optical data can include first optical data from a first photodetector, based on the interaction between the light emitted from the probe and the first photodetector. In addition, the optical data can include second optical data from a second photodetector, based on the interaction between the light emitted from the probe and the second photodetector. In some cases, the optical data can include a time-varying intensity profile (e.g., represented by intensity values of the optical data), which can correspond to the time-varying intensity profile of the photons emitted from the one or more photon sources. For example, the shape of a portion of (or the entire) second time-varying profile of the optical data can correspond (e.g., can be substantially the same as) to the shape of a portion of (or the entire) first time-varying profile of the photons emitted from the one or more photon sources.

At 312, the process 300 can include a computing device determining response information using the optical data (e.g., one more sets of optical data). For example, the computing device or controller may compare or analyze the first time-varying profile and the second time-varying profile. Similarly or additionally, the computing device or controller may analyze or compare the sub-signals used to create the first time-varying profile and extract components of the sub-signals from the second time-varying profile. In some cases, such comparison or analysis may consider one or more time delays, one or more phases, one or more time constants (e.g., a time constant being a lifetime). For example, including when the time-varying profile of the photons emitted from the one or more photon sources is an impulse, a computing device can determine a first time at which the photons begin being emitted from the one or more photon source (e.g., using a time stamp). Then, a computing device can determine a second time at which one or more intensity values from the optical data exceed (e.g., is greater than) a threshold value (e.g., corresponding to background light, which can be noise). Correspondingly, then, a computing device can determine the time delay by subtracting the first time from the second time. In some cases, a computing device can determine multiple time delays, using the process above, using different starting time for the first time and using different thresholds to determine the second time. This can be done using the time-varying profiles and/or the sub-signals.

As another example, a computing device can determine a phase difference between two time-varying profiles or sub-signals. For example, a computing device can determine a first time-varying amplitude wave having a frequency from the first time-varying amplitude profile corresponding to the photons emitted from the one or more photon sources, and can determine a second time-varying amplitude wave having a second frequency from the second time-varying amplitude profile of the optical data. In some cases, the time-varying amplitude profile corresponding to the photons emitted from the one or more photon sources can be data from the electrical waveform used to drive the one or more photons, or optical data received by the one or more photodetectors based on photons from the one or more photon sources (e.g., UV light) directly interacting with the one or more photodetectors (e.g., the photodetectors receiving UV light). In some cases, the first frequency can be substantially similar to (or identical) to the second frequency. Then, a computing device can determine the difference in phase between the first time-varying amplitude wave and the second time-varying amplitude wave.

In some cases, including when the first time-varying profile includes first multiple frequencies and the second time-varying amplitude profile includes second multiple frequencies, a computing device can determine a first reference time-varying amplitude wave having a first reference frequency and a second reference time-varying amplitude wave having a second reference frequency. For example, a computing device can combine (e.g., by using a multiple regression approach) the first multiple frequencies (e.g., a fundamental frequency, one or more harmonics of the fundamental frequency, etc.) into the first reference time-varying amplitude wave In other words, a computing device can combine the multiple frequencies (e.g. a fundamental frequency and higher harmonics) with their amplitudes and phase, into one signature (e.g., using a statistical approach, such as a multiple linear regression). Similarly, a computing device can combine (e.g., by using a multiple regression approach) the second multiple frequencies (e.g., a fundamental frequency, one or more harmonics of the fundamental frequency, etc.) into the second reference time-varying amplitude wave. In some cases, the first reference frequency can be substantially similar (or identical to) the second reference frequency. Then, a computing device can determine the difference between the frequencies contained in the first reference time-varying amplitude wave and the second reference time-varying amplitude wave, for example, a phase difference. In some configurations, by using a first reference time-varying amplitude wave with multiple frequency components, the detection of luminescence can be more robust (e.g., more accurate) than if only a single frequency were used (e.g., in the case of measuring multiple luminescent dyes with different lifetimes or when the lifetime of a single dye may experience an increase or decrease requiring a different measurement frequency) or over a greater operational or dynamic range.

In some embodiments, a computing device (or an electronic filter) can filter each time-varying amplitude profile to isolate one or more of frequencies above. In some cases, this can include digitally filtering the time-varying amplitude profile in the time domain or the frequency domain (e.g., using a Fourier transform (FT), a fast Fourier transform (FFT), etc.). In some cases, if filtering in the frequency domain, the resultant frequency information can be converted back into the time domain to then determine the difference in phase.

As yet another example, a computing device can determine one or more time constants from the time-varying intensity profile of the optical data received by the one or more photodetectors when, for example, the time-varying intensity profile of the photons emitted from the one or more photon sources is an impulse. For example, a computing device can fit an exponential decay function with the optical data to determine a time constant. In some cases, the exponential decay function can be a single exponential decay having a single time constant, or can be a multiple exponential decay with multiple time constants. In the latter case, a computing device can determine each time constant from the multiple exponential decay, and can utilize one or multiple of the time constants, or can combine each time constant to determine a resulting time constant. For example, a computing device can extract the different lifetime of oxygen-sensing dyes embedded in different regions having different diffusion constant.

In some embodiments, a computing device can spectrally determine a time constant from the time-varying intensity profile. For example, with sufficiently fast data sampling, a computing device can spectrally analyze the time-varying intensity profile (e.g., in the frequency domain using, for example, an FT, or FFT of the time-varying intensity profile) to determine an amplitude and phase at a given frequency of a first and second reference time-varying intensity profiles (e.g., at the fundamental frequency or higher order harmonic). Then, the relative phase between the first and second reference time-varying intensity profiles at a given frequency can be obtained by the difference in phase, which can be used to determine the lifetime, e.g. in the case of sinusoidal modulation through the relation $\tan(\theta)=2\pi\tau f$ (where $\theta$ is the relative phase, f is the given frequency and $\tau$ is the lifetime).

At 314, the process 300 can, optionally, include a computing device receiving temperature data from one or more temperature sensors. In some cases, the temperature data can include at least one of a first temperature data from a first temperature sensor in thermal communication with the tissue, second temperature data from a second temperature sensor in thermal communication with the oxygen sensor, and third temperature data from a second temperature sensor in thermal communication with the one or more photon source.

At 316, a parameter can be determined from the above analysis. As but one example, the monitoring may include sensing an analyte and, thus, the parameter may be relative to the analyte. As one non-limiting example, the analyte could be oxygen and the monitoring may be of oxygen level (e.g., of a tissue of a subject) such as via an oxygen partial pressure, which can be implemented using the oxygen sensors systems described herein. Thus, the process 300 can include a computing device determining an oxygen partial pressure based on the response information. For example, this can include determining the oxygen partial pressure based on at least one of the phase difference, the time delay, or the time constant. In particular, the phase difference can be compared to a calibration curve (e.g., a Stern-Volmer curve) that relates phase differences and oxygen partial pressures to determine the oxygen partial pressure. Similarly, the time delay can be compared to a calibration curve (e.g., a Stern-Volmer curve) or at least one of a pre-determined look up table that relates time delays and oxygen partial pressures to determine the oxygen partial pressure. In addition, the time constant (or in other words the lifetime) can be compared to a calibration curve (e.g., a Stern-Volmer curve) that relates time constants or phase differences to oxygen partial pressures.

In some cases, the temperature data (e.g., received at the block 314) can be used, in addition to the response information, determine the oxygen partial pressure. For example, the calibration curve (e.g., a Stern-Volmer curve) can include temperature dependency, and thus a computing device can use the temperature data from the temperature sensor in thermal communication with the tissue, along with the response information, to determine the oxygen partial pressure.

At 318, the process 300 can generate and/or communicate a report. In this case, the computing device can be the controller and/or a separate computing device. In one non-limiting example embodiment, the device measures the waveforms and has an algorithm embedded into the controller, does on-board processing, and simply tells a phone or computer connected to it what $pO_2$ it measures. In another non-limiting example embodiment, the device sends the waveforms to the phone or computer, and the signal is analyzed on the phone or computer to obtain a $pO_2$ value. In some cases, if a computing device determines that the oxygen partial pressure exceeds the threshold value, then a computing device can alert or otherwise notify a user (e.g., a practitioner) by for example, activating an alarm, presenting a graphic on a display, etc. For example, a computing device can determine a presence of ischemia of the tissue based on the oxygen partial pressure being below the threshold value, and a computing device can then notify a user accordingly. As another example, a computing device can determine a presence of oxygen poisoning based on the oxygen partial pressure being above the threshold value, and a computing device can then notify a user accordingly. Thus, in another non-limiting example, the process 300 can be used to determine the presence of ischemia (e.g., a lack of blood) of a tissue (e.g., that is engaged with the oxygen sensor), or determine the presence of supraphysioglical oxygen concentration (e.g., when a tissue is undergoing hyperbaric treatment).

In some cases, regardless of the report of the block 318, the process 300 can include a computing device displaying the results of the one or more blocks of the process 300 (e.g., in the form of a report). For example, a computing device can display the response information, one or more of the time-varying intensity profiles, the oxygen partial pressure, etc. In some cases, the process 300 can proceed back to the block 306 to continuously monitor oxygen partial pressure values of the subject. This can be done, for example, in real time.

As described above, the process 300 can be implemented using one or more computing devices (e.g., a controller), as appropriate. In the non-limiting example of monitoring partial oxygen pressure, the determination of partial oxygen pressure can be carried out through estimation of lifetime and intensity of the luminescence, e.g. algorithmically (multiple linear regression, non-linear regression, lock-in detection, FFT, etc.). In other non-limiting examples, the lifetime and intensity can be obtained through machine learning. In yet other non-limiting examples, the partial oxygen pressure can be calculated from lifetime and intensity through, e.g. calibration look-up tables, empirical equation-based models, or machine learning.

As described above, the process 300 can include determining a calibration curve (e.g., a Stern-Volmer curve), or one or more calibration values. In some cases, the probe, rather than being placed in contact with, gas communication with, fluid communication with, or otherwise able to acquire information relative to a tissue of a subject, can be placed in multiple oxygen partial pressure (and temperature) known conditions. Then, the blocks 306-314 can be completed for each oxygen partial pressure value (and each temperature value). Then, a computing device can construct a calibration curve, based on the known oxygen partial pressure values (and known temperature values) and the corresponding response information (e.g., the time delays, the phase differences, the time constants, etc.) as well as the corresponding temperature data (as appropriate). In some embodiments, a computing device can determine one or more calibration values based on comparing the constructed calibration curve to another calibration curve (e.g., an ideal calibration curve, such as an ideal Stern-Volmer curve). For example, the differences between each respective point of these curves can be determined and used to refine the determined oxygen partial pressure (e.g., at the block 316). For example, the computing device can increase (or decrease) the determined oxygen partial pressure to a refined partial pressure using a corresponding calibration value.

EXAMPLES

The following examples have been presented in order to further illustrate aspects of the disclosure and are not meant to limit the scope of the disclosure in any way. The examples below are intended to be examples of the present disclosure, and these (and other aspects of the disclosure) are not to be bounded by theory.

Example 1

Wearable devices have found widespread applications in recent years as both medical devices as well as consumer electronics for sports and health tracking. A metric of health that is often overlooked in currently available technology is the direct measurement of molecular oxygen in living tissue, a key component in cellular energy production. Here, this disclosure reports on the development of a wireless wearable prototype for transcutaneous oxygenation monitoring based on quantifying the oxygen-dependent phosphorescence of a metalloporphyrin embedded within a highly breathable oxygen sensing film. The device is completely self-contained, weighs under 30 grams, performs on-board signal analysis, and can communicate with computers or smartphones. The wearable device measures tissue oxygenation at the skin surface by detecting the lifetime and intensity of phosphorescence, which undergoes quenching in the presence of oxygen. As well as being insensitive to motion artifacts, it offers robust and reliable measurements even in variable atmospheric conditions related to temperature and humidity. Preliminary in vivo testing in a porcine ischemia model shows that the wearable is highly sensitive to changes in tissue oxygenation in the physiological range upon inducing a decrease in limb perfusion.

Wearable devices that provide continuous monitoring of physiological variables have found widespread application in recent years as both medical devices and in consumer electronics for sports and health tracking. Commercially available devices can measure a wealth of variables such as heart or respiration rate, blood oxygen saturation, motion, force, temperature, muscle activation, etc. However, commercial wearables still lack essential capabilities to measure several important physiological parameters.

Oxygen concentration is a crucially important parameter that often goes unmeasured, despite the fact that it constitutes a key component in the cellular energy production machinery. Knowledge of tissue oxygen tension or oxygen partial pressure ($pO_2$) at the skin surface can be decisive for diagnostic applications in burns, limb injury and surgical interventions. To this end, blood oxygen saturation measurement ($stO_2$) methods are often used. However, these saturation measurements are indirect measures of tissue oxygen content and do not provide accurate readings when blood flow is impaired. In contrast, transcutaneous oxygen tension measurements (TCOM) are direct measurements of the oxygen available in the tissue ready to be metabolized by cells and do not solely depend on oxygen delivery by blood or the condition of the underlying tissue capillary bed. TCOM devices measure local oxygenation of the tissue and can be advantageous in situations such as the application of tourniquets or hyperbaric treatments, as measurement of $pO_2$ could indicate the onset of tissue ischemia or oxygen poisoning, respectively. Blood oxygen saturation, on the other hand, would lose the ability to measure further changes in these scenarios upon reaching values of 0% or 100% in each case.

Despite its advantages compared to devices that measure oxygen saturation, measurements of $pO_2$ and oxygen tension are not widely utilized mainly because traditional TCOM technology involves the use of bulky equipment, time-consuming and frequent bedside calibration, precise placement, and well-trained operators. An approach described herein to achieve a portable technology for tissue oxygenation monitoring is to create optical tools based on metalloporphyrin molecules which undergo phosphorescence quenching by oxygen. Exploiting this principle can create sensors for transcutaneous oxygen measurements which can be responsive to changes in the lifetime of oxygen-sensing phosphors incorporated within transparent films. However, the ability to detect phosphorescence lifetime often comes at a price as it typically requires cumbersome experimental techniques and large benchtop instrumentation. Early attempts to improve the portability, ease-of-use, and data gathering capabilities of TCOM technologies involved the use of oxygen sensing molecules in studies in which 2D maps of the local oxygenation and oxygen consumption rate of tissue were generated by collecting luminescence intensity images with a modified digital camera. Intensity-based approaches can show excellent performance in specific scenarios with controlled experimental conditions or settings. For example, some work with a paint-on oxygen sensing bandage found that the transdermal monitoring of oxygenation was able to detect limb ischemia when arterial ligation was performed on a rat model, proving that transdermal oxygenation can be a non-invasive alternative to measuring tissue health. Techniques sensitive to phosphorescence lifetime as described herein, on the other hand, exhibit significant advantages as they typically do not experience signal variability from changes in sensor geometry, excitation source intensity, photobleaching, etc., that can plague intensity-based methods. Current advances in low-power electronics, communications and materials engineering have contributed to the development of TCOM wearables, however, these are bulky (e.g., rely on large external readout electronics) or involve invasive components or procedures.

In this Example, a wireless and non-invasive wearable prototype has been developed that aims to continuously monitor tissue oxygenation based on in-house developed metalloporphyrins, which can be readily embedded within polymer films, thus providing materials that exhibit bright emission throughout the physiological $pO_2$ range.

Figure 11:
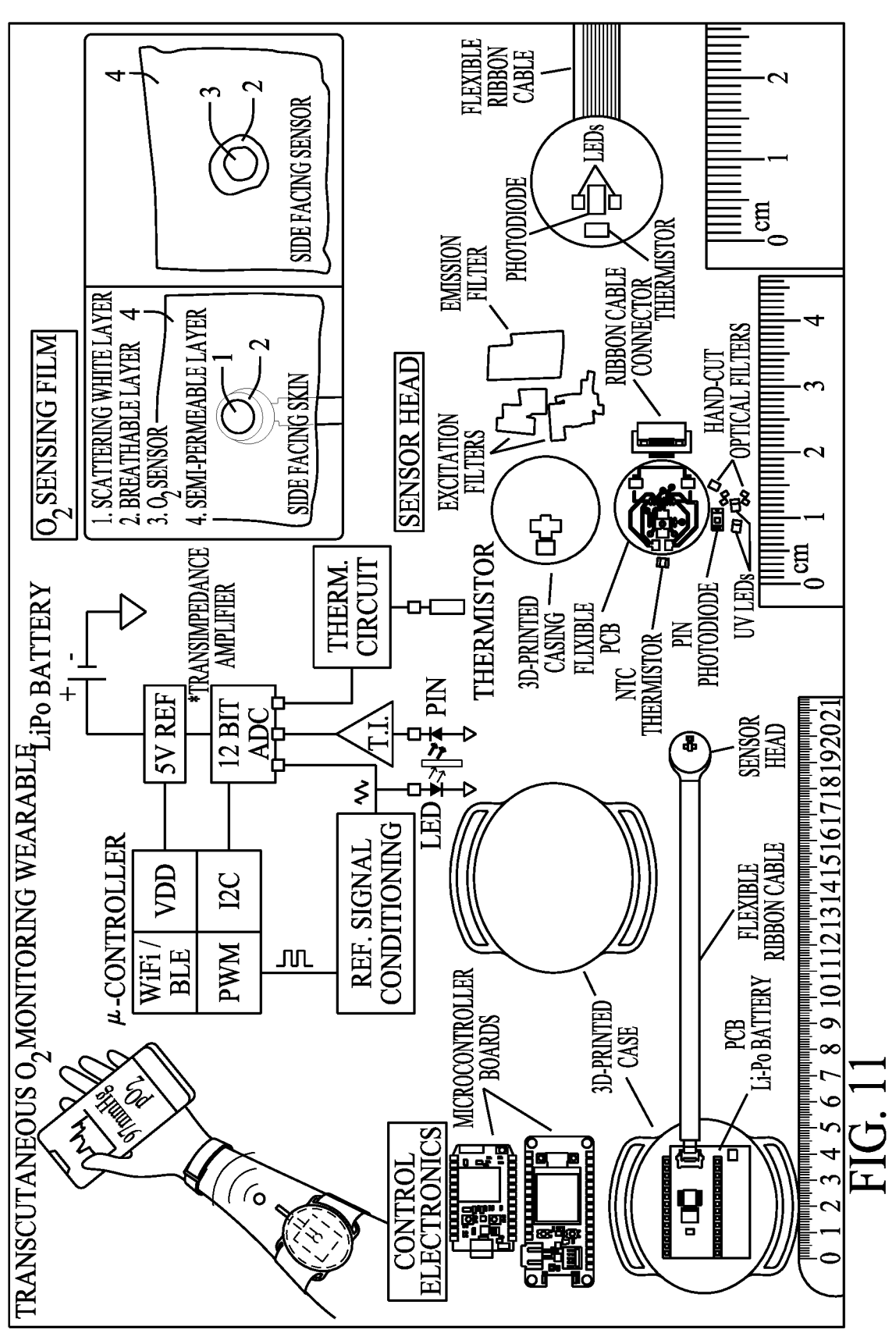
FIG. 11 shows an optical wireless wearable prototype for transcutaneous monitoring based on the phosphorescence emission of a highly breathable sensing film. The prototype is composed of a sensing film, a sensor head, and control electronics. The block diagram represents the control electronics and sensor head circuits.

FIG. 11 shows an optical wireless wearable prototype for transcutaneous oxygen monitoring based on the phosphorescence emission of a highly breathable oxygen sensing film. The prototype is composed of an oxygen-sensing film, a sensor head, and control electronics. The block diagram represents the control electronics and sensor head circuits.

Figure 12:
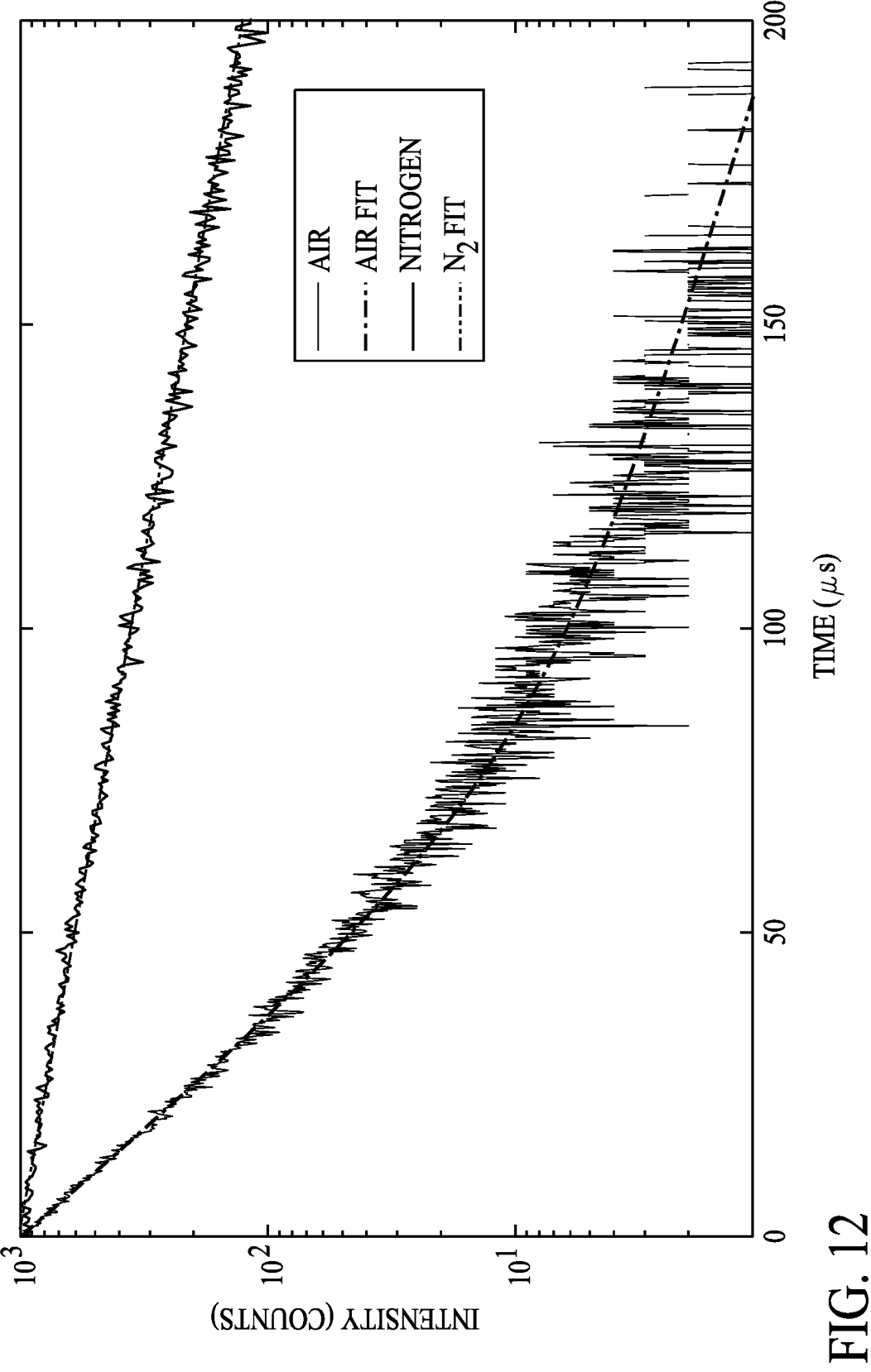
FIG. 12 shows a graph of an exponential decay of the phosphorescence of the sensing film in room air and pure nitrogen atmosphere, and a fit to a double exponential decay.

Response and calibration. The wearable device measures tissue oxygenation at the skin surface by detecting changes in lifetime r and intensity I of the phosphorescence emission of a highly breathable multilayer oxygen sensing film. The film exhibits bright luminescence in the $pO_2$ range 0-160 mmHg with a peak emission at 650 nm. It yields a lifetime of approximately 15 μs in room air ($pO_2$=160 mmHg) and approximately 96 μs at zero oxygen (see FIG. 12). The oxygen-sensing film is composed of several layers (see FIG. 11 for film orientation): a semi-permeable transparent membrane which partially isolates the skin from atmospheric oxygen, a poly(propyl methacrylate) (PPMA) film with embedded metalloporphyrins, a transparent and breathable membrane, and a spin coated, white breathable layer which increases the collected emission through back-scattering while also serving as optical insulation from external light sources. The films are impervious to changes in relative humidity, solving one of the key challenges faced when implementing these oxygen sensing materials into wearable devices monitoring human performance, where sweat can vary widely depending on climatological conditions or body location placement.

As shown in FIG. 11, the device is built around a wireless enabled microcontroller and comprises a small sensor head and the main control electronics. The adhesive oxygen sensing film is affixed onto the sensor head, which is 14 mm in diameter and 3 mm in thickness and is comprised of a flexible printed circuit board (PCB) within a 3D printed casing. The PCB is host to several small surface-mount electronics: two high power UVA LEDs (Lumileds, Amsterdam, Netherlands) with a peak wavelength at 385 nm to excite the phosphor molecules and generate emission from the oxygen-sensing film, a PIN photodiode (Osram, Munich, Germany) to detect the emission, and a thermistor (TDK, Tokyo, Japan) to measure temperature. The LED excitation is filtered by stacking two ultra-thin flexible optical notch-filters (Edmund Optics, Barrington, NJ, USA), which serve as a 400 nm short-pass filter in the range of interest (see FIG. 13). A 500 nm long-pass collection filter, which blocks the LED emission, is fabricated by combining a flexible 405 nm long-pass filter (Edmund Optics, Barrington, NJ, USA) and a polyamide film (DuPont, Wilmington, DE, USA) (see FIG. 13). The sensor head is attached to the control electronics via a thin, flexible ribbon cable. By folding the flexible connector and the sensor head under the control electronics case, the sensor head and oxygen sensing film are shielded from mechanical stress. This design helps to both protect the sensor head and provide adhesion, as well as an airtight and stable seal of the $pO_2$ sensing film over the skin (see FIG. 11). The device is a true wearable in that it is entirely self-contained, performs the signal analysis on-board, and weighs only about 30 g.

As shown in the block diagram in FIG. 11 and the analog to digital converter (ADC) output waveforms shown in FIG. 14 (e.g., panel b), the device detects changes in phosphorescence lifetime of the oxygen sensing phosphor by driving the excitation LEDs with a sinusoidal-like reference signal (fr=796 Hz) and measuring the microsecond delay or phase ($\theta$) between the reference signal and the emission signal, also sinusoidal. In the case of only a single lifetime being present in the emission, the phase can be related to lifetime by the expression $\tan(\theta)=2\pi\tau f_r$. Because the film contains a single phosphorescent dye in which 97% of the molecules exhibit the same lifetime (see FIG. 12), a sinusoidal reference signal is sufficient to fully characterize the phosphorescence lifetime. As described below, this allows for a simple signal analysis approach which can be performed on-board a device with limited computing power such as that of microcontrollers. The change in lifetime $\tau$ is also reflected by the intensity I of the emission, which responds to variations in $pO_2$, and is obtained from the amplitude of the measured signal at the driving frequency. An algorithm based on Multiple Linear Regression in the matrix form was developed to extract lifetime and intensity of the emission.

The dependence of the measured variable X, namely $\tau$ or I with $pO_2$, is governed by this equation, modified from the Stern-Volmer relation:

$$X=X_0/(1+K_{eff}*pO_2)+X_{OFF} \qquad (1)$$

where $X_0$ is the value of X in the absence of oxygen and $X_{OFF}$ is a non-oxygen dependent offset arising from the measurement system. In the case of dynamic quenching and diffusion-controlled processes, the Stern-Volmer quenching constant, $K_{eff}$ is a measure of the oxygen diffusion coefficient of the multilayer film. $K_{eff}$ is temperature dependent mainly because of the collisional quenching rate of the porphyrin and to a lesser degree, due to changes in the oxygen-diffusion parameters of the polymer layers, which may also experience changes through aging as was found below. A quadratic dependence of $K_{eff}$ with temperature ($K_{eff}=K_0+K_1*(T-32)+K_2*(T-32)^2$) was found, which accounts for the trends observed in the data measured with prototypes fabricated with the final design seen in FIG. 11. Earlier iterations of the device in which different 3D printed materials were used yielded a negligible quadratic term, which can be seen in the data shown in Table 1 (below), and is explained by slight differences in sensor geometry, LED leakage into the photodiode signal and thermal properties of the sensor head.

Figure 15:
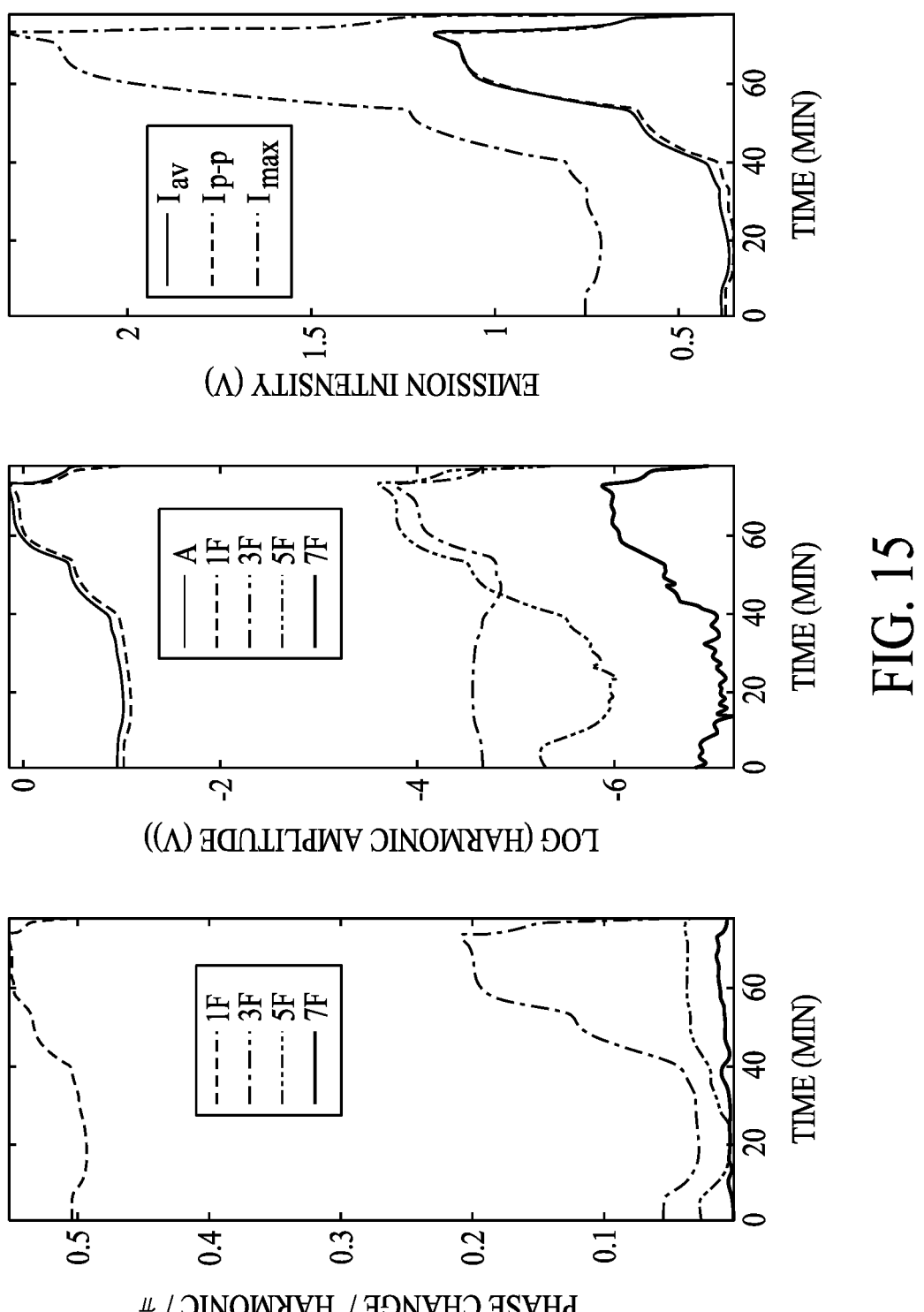
FIG. 15 shows plots vs. time for calibration of phase for each harmonic, divided by its index I and log of offset $\beta_0$, and harmonic amplitudes $I_i$.

FIG. 15 shows a plot of intensity vs. time for the calibration of phase for each harmonic, divided by its index I and log of offset Po, and harmonic amplitudes $I_i$. For example, the left graph shows phase change for each harmonic vs. time, the central graph shows the log of the harmonic amplitude for each harmonic vs. time, and the right graph shows the emission intensity vs. time.

TABLE 1

Lifetime and intensity calibration parameters for three different calibrations of the same oxygen sensing film: an initial calibration, one carried out after removing and repositioning of the film on the sensor head, and a final set after a three-month storage of the device with the attached film. The percentage change of each parameter is in relation to the previously measured value. $K_2$ values are not shown as the result of the fitting yielded values near zero.

| Parameter | Initial | Re-positioned | Aged (3 months) |
|---|---|---|---|
| $\theta_0$ | 0.309 | 0.302(2.1%) | 0.317(+4.8%) |
| $\theta_{OFF}$ | 1.005 | 0.999(−0.6%) | 1.002(+0.3%) |
| $K_0$ | 0.0108 | 0.0114(+5.6%) | 0.0086(−24.6%) |
| $K_1$ | 0.00056 | 0.00058(+3.6%) | 0.00041(−29.3%) |
| $I_0$ | 1.043 | 0.848(−18.7%) | 1.323(+56.0%) |
| $I_{OFF}$ | 0.292 | 0.289(−1.0%) | 0.328(+13.5%) |
| $K_0$ | 0.0822 | 0.0756(−8.0%) | 0.0821(+8.6%) |
| $K_1$ | 0.00236 | 0.00214(−9.3%) | 0.00206(−3.7%) |

Figure 16:
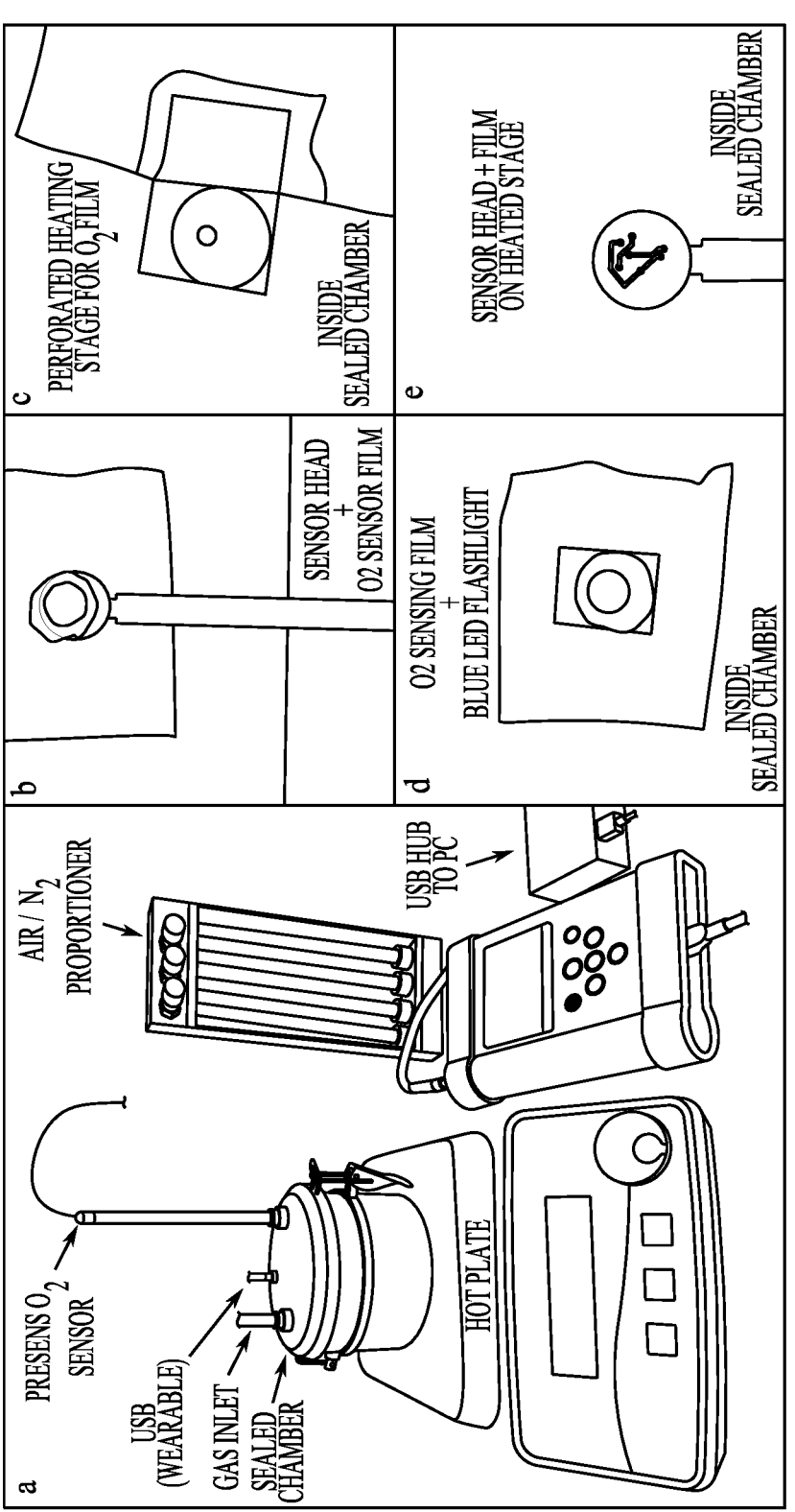
FIG. 16 shows the calibration set-up and mounting of the sensor head on a heating stage inside a sealed chamber.

To evaluate the performance of the prototype, the sensor head was outfitted with an oxygen-sensing film and the device was inserted into a sealed calibration chamber (see FIG. 16). The variation of temperature and oxygen partial pressure during calibration is shown in FIG. 14 (e.g., panel a), during which a first sweep of $pO_2$ is carried out at a high body-like temperature and a second one is performed at room temperature. As can be seen in in FIG. 14 panel b and c, Op monotonically increased as $pO_2$ was gradually swept between atmospheric values (160 mmHg) and a pure nitrogen atmosphere (0 mmHg). Throughout the measurement, temperature was varied between room conditions (24° C.) and the temperature of skin (32° C.). Both $\theta_p$ and $\theta_r$ present similar fluctuations, which stem from slight differences between $pO_2$ measurements in the time elapsed from the PWM output turning "ON" to the ADC sampling start. The fluctuations in Op can be removed by calculating the relative phase change between photodiode and reference signals, e.g., $\theta=\theta_p-\theta_r$, referred to as the phase from here on. The intensity of the emission, as seen in panel d of FIG. 14, shows a very similar response. Both the lifetime and intensity signals present high signal to noise ratio (29 dB and 31 dB respectively) and require no smoothing or filtering in order to achieve a good signal contrast throughout the physiological range. These results were consistent throughout multiple prototypes and $O_2$-sensing films.

Figures 17A, 17B, 17C, 17D, 17E, 17F:
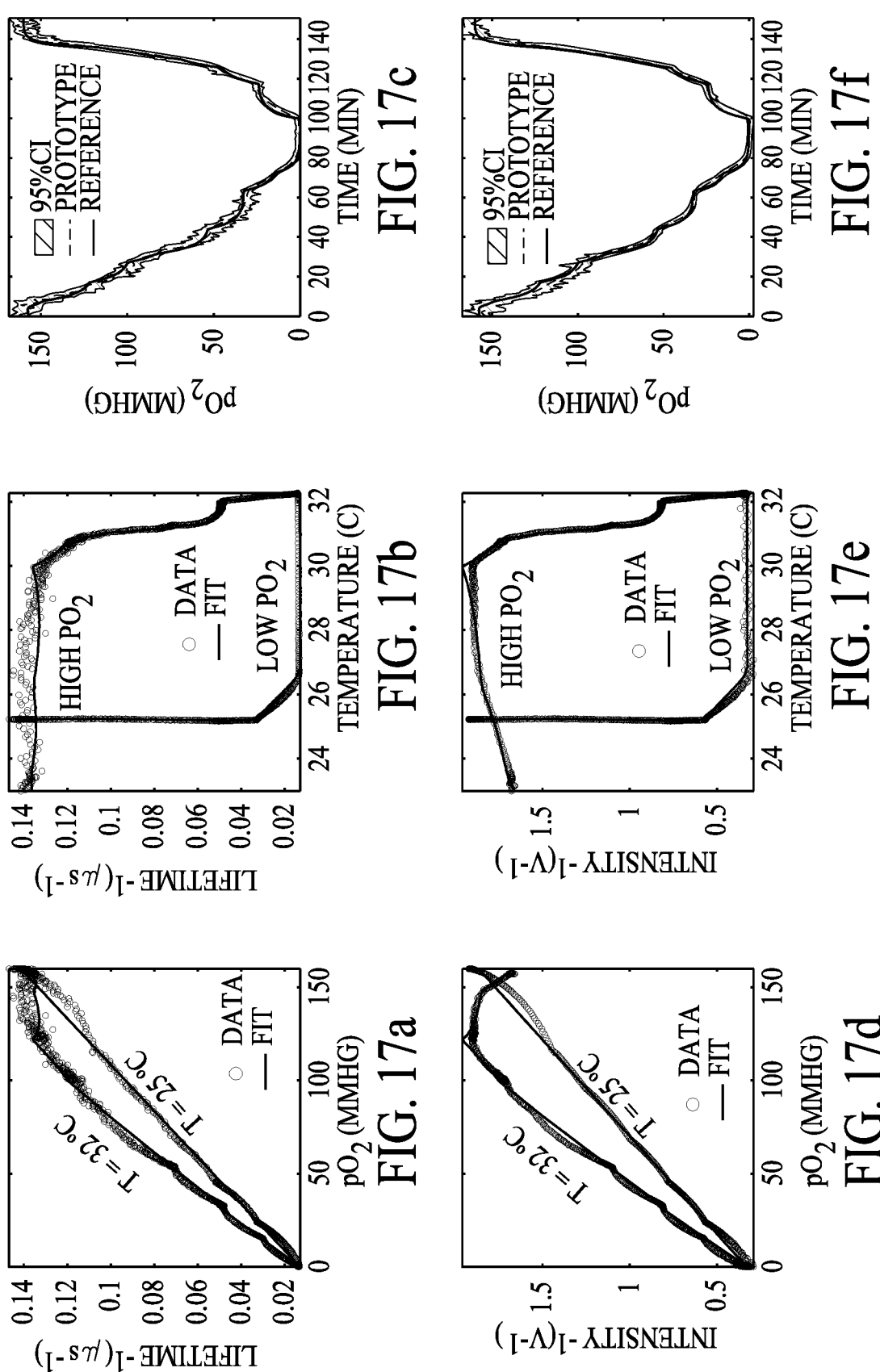
FIG. 17 shows fits of the temperature dependent Stern-Volmer equation. In particular.

Panels a and b (and panels d and e) of FIG. 17, show that features in lifetime and intensity data due to changes in $pO_2$ and temperature, respectively, are well described by the temperature dependent Stern-Volmer equation. The estimate of $pO_2$ obtained from lifetime and intensity data, shown in panels c and d of FIG. 17 respectively, closely match what is measured with a reference commercial $pO_2$ sensor, with discrepancies possibly arising from a difference in response time of both devices and from each sensor experiencing different temperature gradients due to their location within the chamber.

In order to test for reproducibility of the calibration parameters related to the positioning of the sensing film, an already calibrated oxygen sensing film was removed from the device and re-affixed onto the sensor head. The subsequent calibration showed that all the fitting parameters (see Table 1) obtained for lifetime differed very little from the previous values. However, the fitting parameters for intensity were observed to vary with respect to the earlier position of the oxygen sensing film. The invariance of lifetime parameters against sensor placement highlights a key advantage of lifetime-based measurements over intensity-based approaches, which are highly dependent on orientation.

The aging of the film was also tested with time (see Table 1) by storing the device with a film attached for three months, such that it was kept shielded from room lighting but not from changes in ambient conditions. A calibration of the film revealed that $\theta_0$ and $\theta_{OFF}$ parameters remained unchanged with respect to the previous calibration, while $K_0$ and $K_1$ experienced a large decrease, which may point to the film's oxygen diffusion properties being modified with passing time. The intensity parameters did not exhibit a clear trend.

Sensing tissue oxygenation in an in vivo porcine model. To evaluate the response of the device in monitoring tissue oxygenation during physiological changes, an in vivo experiment was conducted on a porcine model (Yorkshire swine). Porcine anatomy and specifically their skin is highly similar to that of humans (structure, thickness, etc.) which makes the porcine model suitable to monitor physiological oxygenation changes transdermally. Changes in tissue oxygenation were induced by occluding blood flow to the front limb of the porcine model by applying a tourniquet above the elbow joint (over the triceps, brachii, and brachialis muscles), as shown in panel a of FIG. 18 for a duration of 30 minutes. The 30-minute waiting period was chosen guided by previous work, to allow for the device to equilibrate to skin $pO_2$. The animal surgery protocol was reviewed and approved by the Institutional Animal Care and Use Committee (IACUC) at Massachusetts General Hospital.

To prepare the region of interest, a 10×10 cm area of the swine's front upper extremity was cleaned with soapy water and shaved until all hair was removed. After shaving, the skin was wiped with isopropanol. The oxygen sensing film was pre-fixed onto the sensor head and atmospheric $pO_2$ was sampled for several minutes as a reference prior to applying the device onto the skin, as seen in panel b of FIG. 18. The reference reading differed from 160 mmHg due to the starting temperature (19° C.) being outside the range of temperatures considered during calibration (23-32° C.). As seen in the data, lifetime $pO_2$ showed room air values close to 160 mmHg when the temperature was within the calibration range (T 23° C.). This issue is easily solved by expanding the calibrated temperature range. Upon application of the device onto the pig's skin, the sensor head quickly achieved thermal equilibrium in approximately 3 minutes due to its small mass. Both estimates of $pO_2$ as obtained from phosphorescence lifetime and intensity, exhibited an exponentially decaying trend due to a number of factors such as initial oxygen trapped between film and tissue, tissue oxygenation, which is a balance between oxygen supplied by the blood and oxygen consumed by the muscle and skin, atmospheric oxygen uptake by the skin, skin oxygen permeability, and atmospheric oxygen permeability through the medical adhesive layer.

Figure 18A:
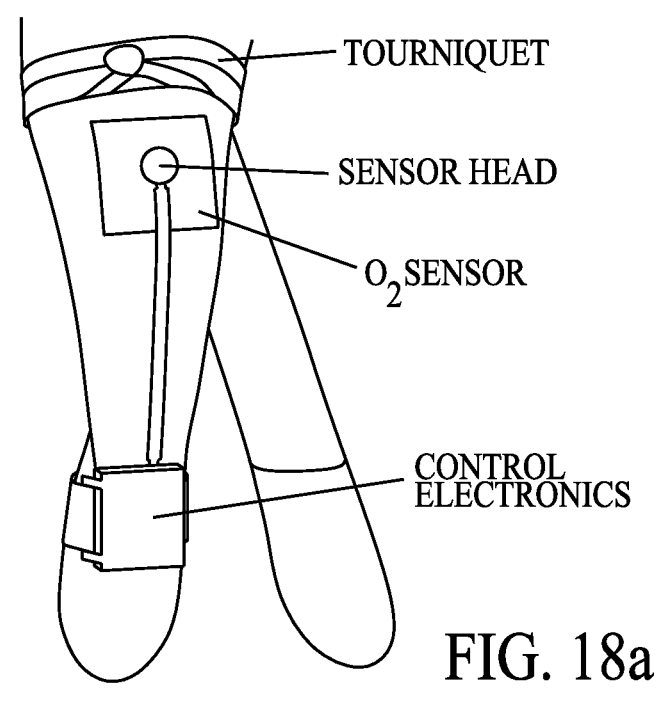
FIG. 18 shows the in vivo testing of the oxygen sensing prototype in a porcine model. In particular.
Figure 18B:
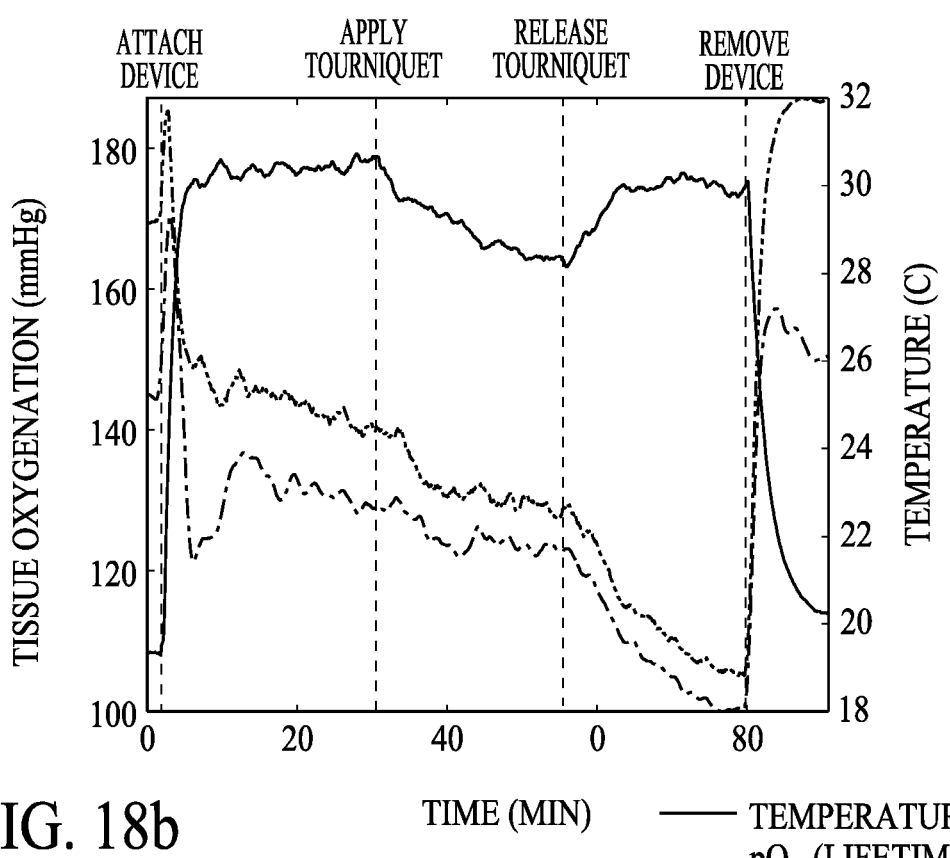
Figure 18C:
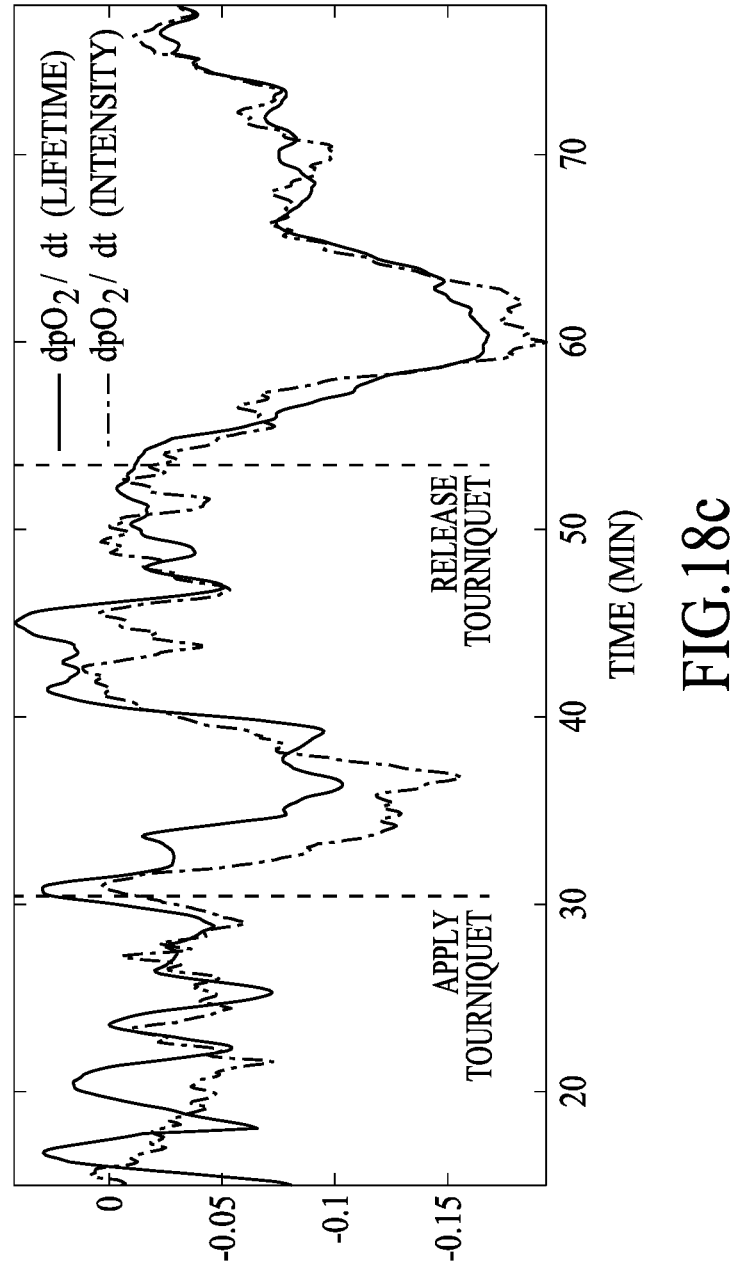

After a 30-minute equilibration period, the tourniquet was applied and both lifetime and intensity $pO_2$ metrics were observed to respond immediately to the compromised blood flow by decreasing at a faster rate (see panel b of FIG. 18). This is clearly seen by plotting the time derivative of $pO_2$, shown in panel c of FIG. 18, which is indicative of oxygen consumption rate in a tourniquet scenario. The data revealed an increasingly negative $pO_2$ slope that reached its maximum value at around 5 minutes into the application of the tourniquet (occlusion). Due to the lack of blood flow, the temperature of the limb decreased by as much as 2.5° C. from the original baseline temperature. The tourniquet was released after 30 minutes, and the temperature of the limb was observed to return to baseline while $pO_2$ once again exhibited an increased rate of decay for around 5 minutes. This further decay, which occurred alongside intense blanching of the limb's skin, could indicate the presence of irreversible tissue damage due to the tourniquet's placement.

These preliminary results demonstrate the device's great potential for applications involving monitoring oxygenation in living tissue. Despite their enhanced capabilities as diagnostic or monitoring tools for predicting wound healing, determining amputation level, hyperbaric oxygen therapy, severity of ischemia, etc., devices which directly measure tissue oxygenation have not found widespread use due to issues such as the need for unwieldy tools, complex calibration procedures, and extensive user training. The developed wearable device overcomes these issues by using readily available, low-power electronic components that can be easily interfaced with multiple devices such as computers or smartphones. The device requires very few components, and its size could be greatly reduced for commercial application. As such, the technology described here could certainly find application in consumer devices, therefore allowing the assessment of tissue oxygen at the point of care, as well as being accessible to those in low resource settings. Furthermore, the processes developed to extract lifetime and intensity from the time series can be suited for implementation in embedded devices with low computing power as it involves simple matrix operations with minimal memory requirements.

Figure 19:
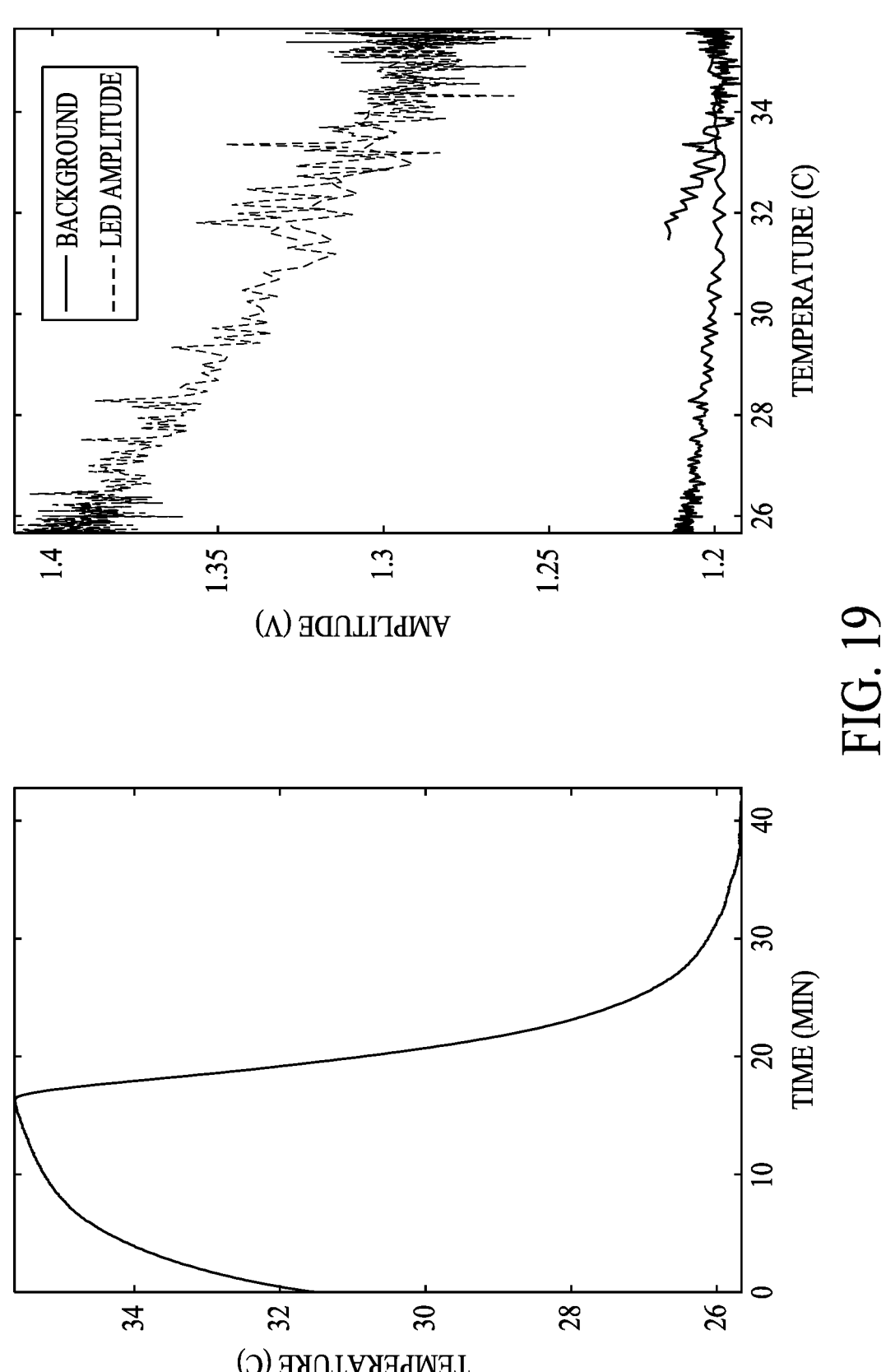
FIG. 19 shows the temperature dependence of the LED leakage. which is measured with the photodiode using a blank control film. The left graph shows the temperature values reached by the sensor head during the measurement over time. The right graph shows the percentage change of the background $((3o$ in the linear regression) and intensity of the fundamental frequency. The value for the background matches the values obtained for $I_{OFF}$, while the LED leakage which is observed in the fundamental mode explains the difference in lifetime measured by this device and the spectrophotometer measurements. Including a linear dependence of the LED amplitude in the Stern-Volmer fit did not improve the quality of the fit and the coefficients obtained were of negligible value.

The measurement is consistently reproducible between devices and calibrations and is robust against changes in temperature and humidity. Because measurements of $pO_2$ are based on lifetime detection, the device presents an important advantage over purely intensity-based measurements that may exhibit instabilities due to factors such as background noise, excitation source fluctuations and photobleaching. These claims are supported by the lifetime calibration parameters remaining constant regardless of film repositioning, which makes the lifetime-based measurement more tolerant to motion. Additionally, as lifetime is not affected by parameters including film placement and LED intensity, the developed device can detect and compensate for effects related to the aging of the polymer film by tracking changes in permeability through the $K_{eff}$ constant. On the other hand, as seen in Table 1, such information could not be obtained from the intensity calibration parameters, as the overall response of intensity with oxygen changed with film aging, which affected film dryness and aggregation, amongst other elements. Furthermore, the lifetime estimate from the developed inexpensive and miniature device agrees well with the lifetime characterization carried out on the oxygen-sensing film with a state-of-the-art spectrometer (FLS1000 Steady State and Phosphorescence Lifetime Spectrometer, Edinburgh Instruments, Livingston, UK); the values for atmospheric and zero oxygen at 24° C. for the device are 10 and 80 µs, while those obtained with the spectrometer are 15 and 96 µs. The difference could be due to excitation light leaking into the detector (see FIG. 19) or the presence of more than one lifetime species (see FIG. 12), which can result in the detection of a lower average lifetime. These contributions could be taken into account with an appropriate model to better estimate the lifetime, however, we are able to obtain a reproducible relation between the phase and $pO_2$ which was the main objective of the project.

This Example also proves the feasibility of the device's application in in vivo measurements on a porcine occlusion model. After inducing physiological changes, this device was capable of monitoring variations in tissue $pO_2$ on the skin surface, responding quickly to changes in local oxygenation. Changes in variables such as temperature, humidity and skin blanching can confound $pO_2$ measurements based on oxygen quenching of phosphorescence and are often overlooked or ignored in literature or are overcome by adding heating elements which prohibits the application of such tools, for example, in neonatal care. The device presented here was able to track changes in tissue oxygenation during an in vivo experiment without the measurement being affected by these variables. For a non-temperature compensated system, an increase in temperature could be misinterpreted as an increase in $pO_2$. During in vivo testing, $pO_2$ was observed to decrease faster upon both the application and removal of the tourniquet, which cannot be explained by the changes in limb temperature alone. Colder temperatures were not considered during the calibration of the film that was used for the in vivo study, but instead focused on warmer body-like temperatures. To address this in future studies, the sensor can be simply re-calibrated by sweeping a wider range of temperatures, which can be done using the calibration chamber, a hot plate and ice/water mixtures, etc.

The device shows an ideal response time to detect physiological changes, which typically occur in the timescale of minutes. The fact that each component of the device was designed to be biocompatible (or skin-friendly) will accelerate the pace of translation as this wearable tool is brought into first-in-human clinical studies. Since the measurement is performed on the skin surface, with both skin and muscle contributing to the signal, and the little homogeneity which exists in how transcutaneous measurements are used to assess limb ischemia, the interpretation of transdermal oxygen measurements is complex and challenging, with many physiological factors which can contribute to the signal which are not yet well understood today.

Oxygen-sensing film. Chemicals and adhesives: The pivaloyl-terminated, platinum porphyrin embedded within the oxygen-sensing film was prepared according to previous protocols. Poly(propyl methacrylate) (PPMA) was purchased from Scientific Polymer Product. The adhesives used for the semi-permeable membrane (3M™ Medical Tape 1513, Double Sided Transparent Polyester, 80 #Liner, Configurable) and the breathable membrane (3M™ Medical Transfer Adhesive 1524, Fiber Filled Polyester, 60 #Liner, Configurable) were purchased from 3M. The $TiO_2$ white pigment concentrate and (45-55% methylhydrosiloxane)-dimethylsiloxane copolymer (HMS) were purchased from Gelest. Platinum(0)-1,3-divinyl-1,1,3,3-tetramethyldisiloxane complex solution (platinum catalyst) was purchased from Sigma-Aldrich.

Oxygen-sensing PPMA layer: 0.5 mg/µl PPMA in dichloromethane was prepared in a small, clean Eppendorf tube. An aliquot from a stock solution of pivaloyl platinum porphyrin, such that the concentration of metalloporphyrin in the final solution was 30 µM, was added to the PPMA solution and mixed thoroughly by vortexing. 20 µl of porphyrin/PPMA solution was deposited into an 8 mm diameter circular mold made with PDMS on a glass slide. The PPMA oxygen-sensing film was removed from the glass slide after drying in the hood for 30 minutes.

White scattering layer: 1 g of white pigment concentrate was mixed thoroughly with 3 µl of platinum catalyst on a weighing boat. The mixture was added to a glass slide and spin coated for 1 minute at 1,500 rpm. 0.1 g of HMS copolymer was added on top of the white pigment film and spin coated for 1 minute at 750 rpm. The white scattering layer was allowed to fully cure overnight.

Sensor head: The flexible PCBs were designed with the KiCad software and fabricated with polyimide flexible substrates (OSH Park, Portland, Oregon, USA). The casing was fabricated with a Formlabs Form 3B 3D printer at resolution of 25 µm utilizing a biocompatible photopolymer resin suited for medical applications. The fabricated parts were then washed in a 90-100% isopropyl alcohol (IPA) bath for 20 minutes agitated by a magnetically coupled impeller and LED/heat cured at a wavelength of 405 nm for 30 minutes at 60° C. Post curing, the fabricated parts could then be sterilized chemically or by autoclave. This component served as an optical mask for mounting the excitation and emission filters. It also served to optically isolate the LEDs from the photodiode, and as a skin-friendly, flat surface over which to place the oxygen-sensing film. The optimal geometry was found to be a planar configuration of the LEDs and photodiode, and to have the components as close as possible. The casing was attached to the PCB with UV-curing epoxy (Thorlabs, Newton, NJ, USA), which provided mechanical stability and optical transparency for the propagation of excitation and emission optical signals. Additionally, the epoxy acted as a thermal link between the $O_2$ sensing film and the electronics (LEDs, photodiode and temperature sensor), which, due to the small size and mass of the sensor head, allows fast thermal equilibration, resulting in precise local temperature readings of the skin surface, film, and LEDs with a short response time.

Figures 13A, 13B:
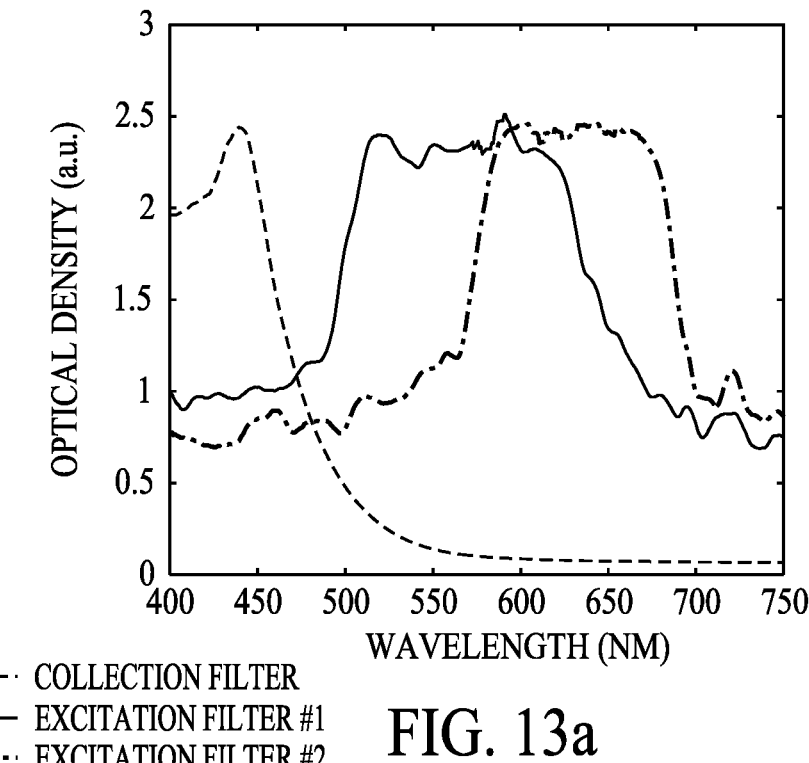
FIG. 13 shows panels a, b, and c. Panel a shows a graph of the optical density of the excitation and collection optical filters. Panel b shows the optical spectrum of the pulsed LED, revealing an unwanted phosphorescence, which overlaps with the emission spectra of the sensing porphyrin. Panel c shows a graph of the optical spectrum showing that the emission filters successfully filter out the unwanted light from the LEDs.
Figure 13C:
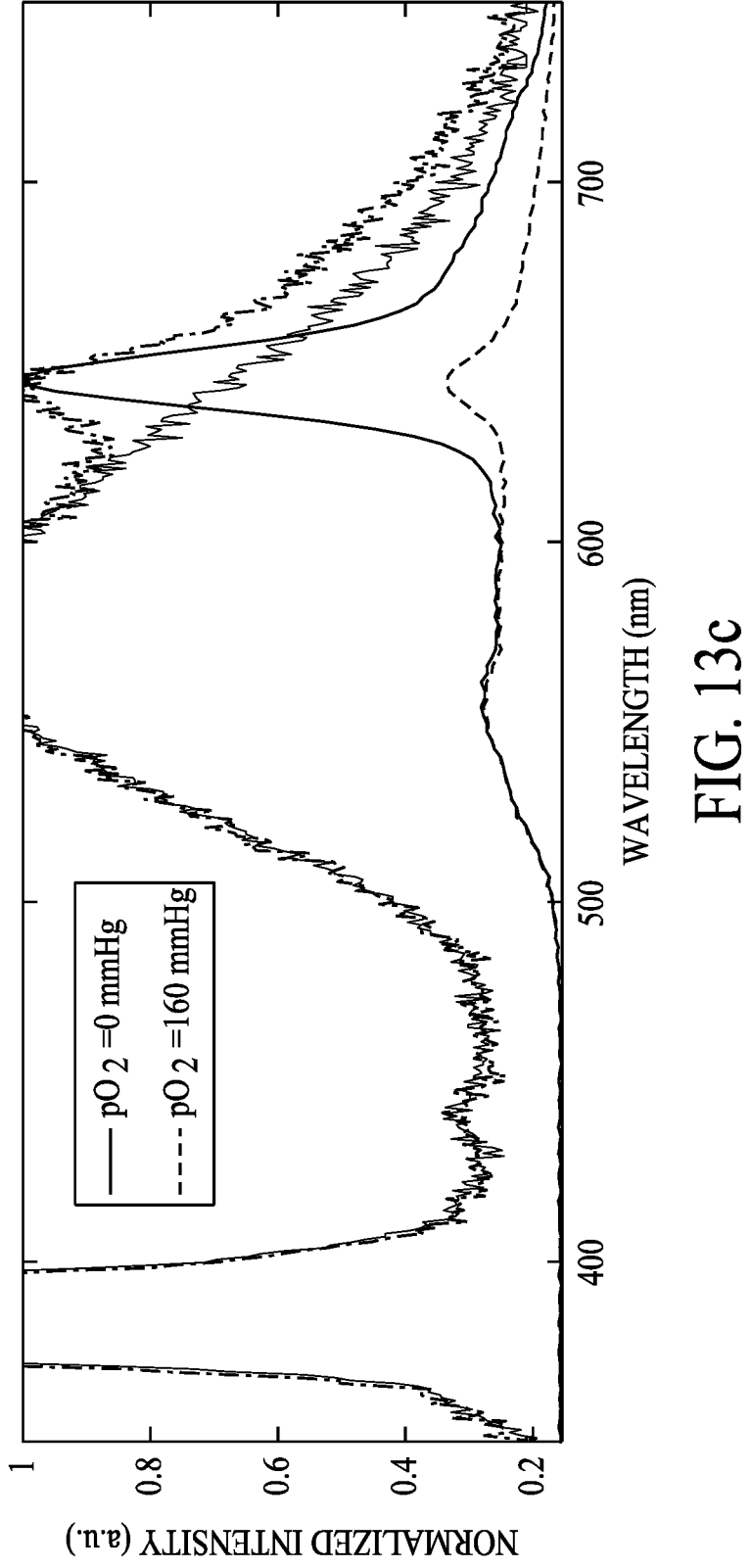
Figure 14A:
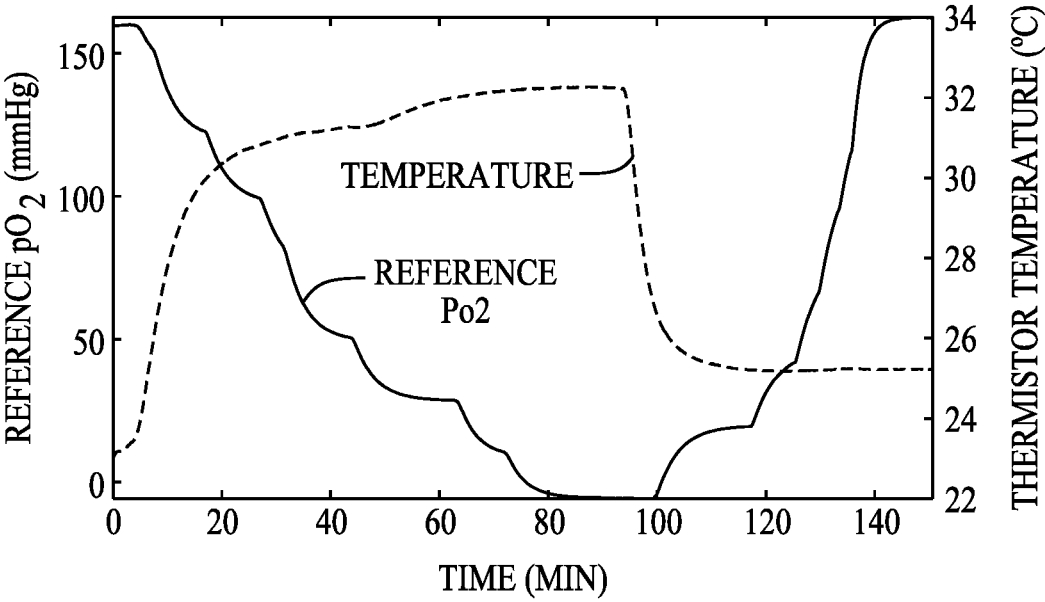
FIG. 14 shows a response of the sensing film to $pO_2$ and temperature during a calibration run. In particular.
Figure 14B:
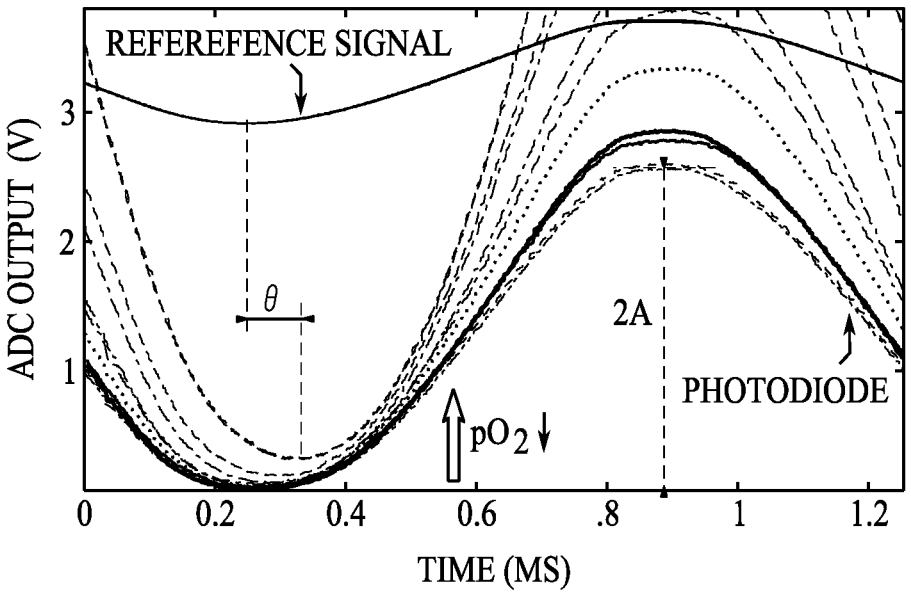
Figure 14C:
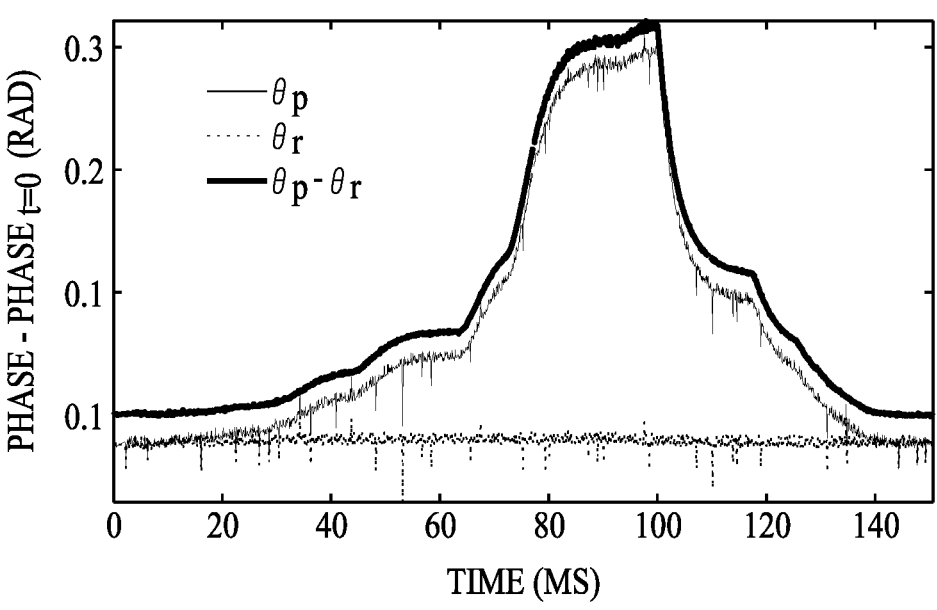
Figure 14D:
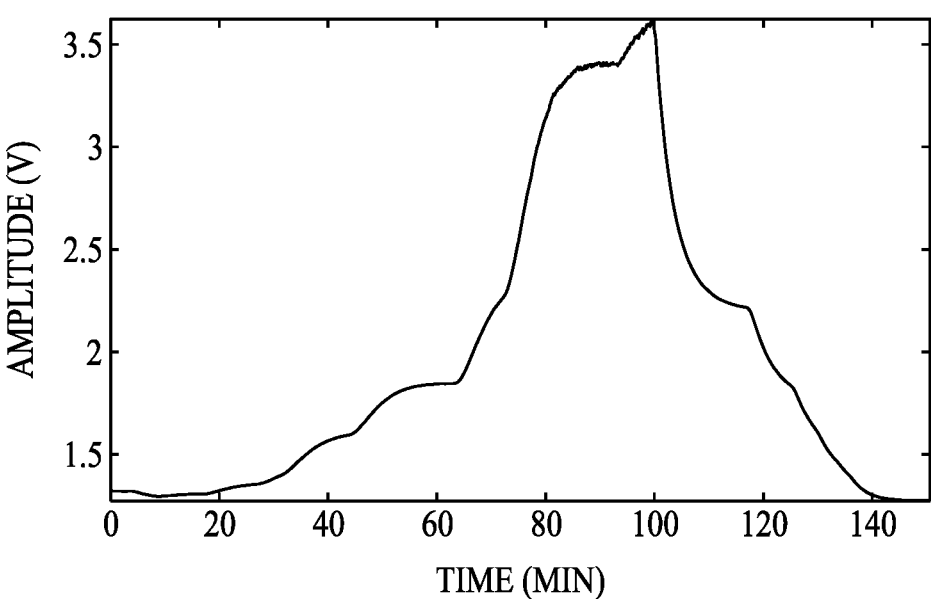

Control electronics: The PCBs were designed with the KiCad software and fabricated with standard fiberglass substrates (OSH Park, Portland, Oregon, USA). A flexible ribbon cable (Molex, Lisle, IL, USA) connects the sensor head to the control electronics, comprising a custom designed PCB with electronics built around a Particle Photon or Argon microcontroller board (Particle, San Francisco, CA, USA) with Bluetooth Low Energy (BLE) and/or WiFi connectivity, powered by a rechargeable lithium polymer battery (see FIG. 11). The microcontroller communicates via I2C with a 12-bit analog-to-digital converter (ADC) (Texas Instruments, Dallas, TX, USA), which samples the reference signal, the photodiode signal and the thermistor voltage through three differential voltage channels. With the 5V reference provided, the ADC achieves a resolution of 1.2 mV/bit. The LEDs are modulated by a sine-like wave voltage signal (the reference signal) of programmable frequency (fr). A reference frequency of fr=796 Hz was used for this study. The reference signal is obtained by low pass (LP) filtering (4-pole with corner or roll-off freq. fc=ft) and amplifying (gain ×2) a square wave (PWM) output supplied by the micro-controller (see FIG. 20 panels a and b). The filter and gain were chosen to achieve an optimal depth-modulation of the LEDs, which produce a high contrast, sine-like emission with a very low minimum output and a high brightness maximum. The LP filter approach was chosen as a simple way to obtain a sine-like reference signal using only passive components. Using a function generator, the LEDs were found to produce brighter emission for frequencies below 1 kHz. Additionally, as shown in FIG. 13 panel c, the LEDs also exhibit a broad phosphorescence in the spectral region in which the oxygen sensing dye emits, and the ratio of blue emission to phosphorescence was highest for slower frequencies. The 796 Hz value is arrived at by using R=5 kΩ, C=0.1 µF so fc=1 $2\pi RC$.

The photodiode signal is amplified by a transimpedance amplifying circuit (e.g., a transimpedance amplifier or TIA). The TIA gain was chosen to maximize the use of the dynamic range of the ADC (e.g., the ADC counts are high but do not saturate at maximum phosphorescence signal) once the sensor head geometry, porphyrin concentration and reference signal frequency were fixed. With this resistor fixed at 2.5MΩ, and a feedback capacitor of C=0.1 pF, a bandwidth of 636 kHz is achieved. More information on the DC and AC characterization of the TIA, as well as ADC inputs and outputs can be found in FIGS. 20-23.

Temperature was measured by a two-resistor circuit composed of a thermistor of $R_1$=10 kΩ and B-value of 3650 (see FIG. 24) and a reference resistor ($R_2$=5 kΩ), and using the Steinhart-Hart thermistor equation. A 3D printed casing (see FIG. 11) was designed to house the electronics and allow the secure fastening of the device onto a limb through an elastic band or strap.

Calibration: The calibrations were carried out in a sealed calibration chamber in which the temperature and $pO_2$ can be controlled by a hot plate and by varying the mix of nitrogen and air gas being fed into a gas mixer, as shown in FIG. 16. The partial oxygen pressure in the chamber was measured with a commercial oxygen sensor (PreSens, Regensburg, Germany).

Data collection: To obtain a single measurement of $pO_2$ the modulated LEDs are flashed for around 0.2 seconds, during which 1000 measurements of time, voltage pairs are recorded for both reference and photodiode signals, where the time is measured in microseconds. The LED flash duration is determined by the ADC sampling rate and the desired number of acquired data points. The number of data points (1000) was chosen as it provides the amount of detail required to extract the phase and intensity values with precision. By using the modulo operator, we use the time variable t'=mod(t, T) with T=1/fr, which allows us to reconstruct a single oscillation of the reference and photodiode signal with an effectively high time-resolution (see FIGS. 22, 23, and 25). Data was collected through a Python script on a PC through USB serial port or through Bluetooth.

Data analysis: Extracting phase and intensity. The reference signal is dominated by a sine at the fundamental frequency, but higher order odd harmonics (3f, 5f, 7f, . . . ) contribute to the signal, which are not fully filtered out from the square-wave PWM source. Plotting the Fast Fourier transform (FFT) of the reference signal (see FIG. 25 panel c) shows that the amplitude of harmonics 3f, 5f, 7f is only 2.3%, 0.8% and 0.3% that of the fundamental frequency. It was found that including terms up to 7f improves the accuracy of the fit and allows determining the phase with high precision and reproducibility. As can be seen (see FIG. 25 panel c), the photodiode signal requires including even harmonics (2f, 4f, . . . ) as well, as they are present in the phosphorescence due to the non-linear nature of LEDs.

The following function is fit to the reference and photodiode signals using Multiple Linear Regression in the matrix form:

$$y(t)=\beta_0+\Sigma_i(\beta_{2i-1}\cos(i2\pi ft)+\beta_{2i}\sin(i2\pi ft)),i\in[1,2,3,4,\\5,7,\ldots] \quad (2)$$

where cos 2πft+θ=cos θ cos 2πft-sin θ sin 2πft. The least squares coefficients βi allow for the calculation of the intensity (I) and phase (θ) of the fundamental frequency:

$$I=\sqrt{\beta_1^2+\beta_2^2} \quad (3)$$

$$\theta=\arccos\left(\frac{\beta_1}{I}\right) \quad (4)$$

The result of the fitting can be seen in FIGS. 26a-26d. The data analysis was carried out using GNU Octave and re-written to C++ for the device to perform the calculations on-board.

Error calculation: The standard error of the least squares coefficients is obtained from the variance-covariance matrix of the fitting parameters. The standard error of θ and I is calculated by error propagation. The 95% confidence interval (95% C.I.) of the $pO_2$ values obtained from both phase and intensity measurements was calculated by estimating the standard error of $pO_2$ using the Stern-Volmer equation and error propagation.

The lifetime of our oxygen sensing film was measured in room air ($pO_2$=160 mmHg) and in deoxygenated conditions at room temperature with an Edinburgh Instruments photospectrometer air measurements, with 97% of the phosphors having τ=14.92 µs and the remaining 3% yielding τ=57 µs. The 3% is shielded from changes in oxygen, as the deoxygenated measurement gives by fitting a double exponential decay, we obtain that there are two different lifetimes in the room 100% of emitters having τ=95.73 µs.

Figures 20A, 20B:
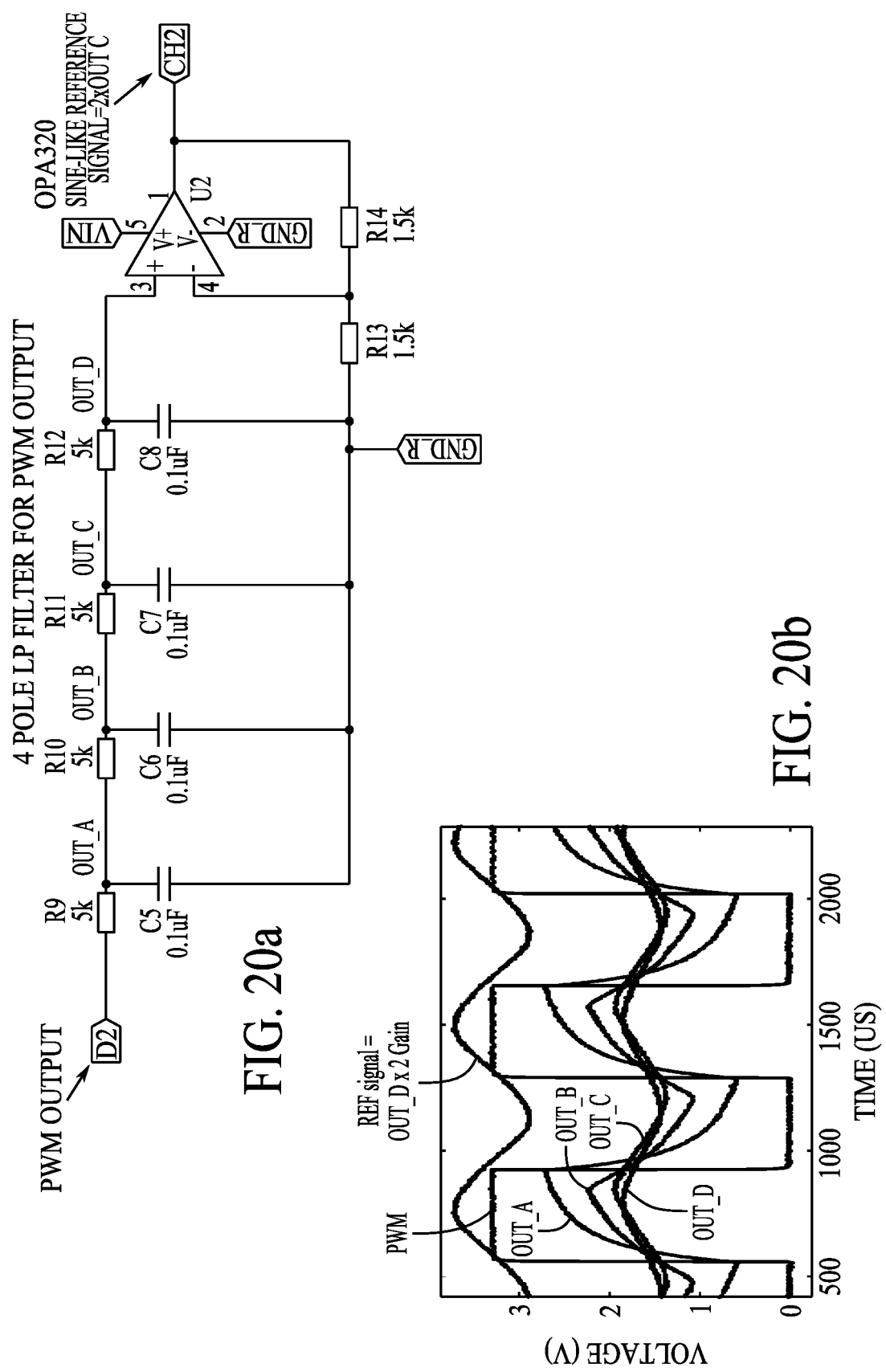
FIG. 20 shows the electronics schematics. For example.

Circuit design and characterization. Schematics. FIG. 20 shows the schematics of the reference signal conditioning circuit in panel a (and node signals measured by an oscilloscope in panel b), the ADC connections in panel b, and the ribbon cable connections between the control electronics PCB in panel d and the sensor head in panel e.

Concerning the signal conditioning circuit, the capacitor for the 4-pole low pass filter was fixed at 0.1 µF, and the resistor was chosen so that the cutoff frequency of the LP filter was centered at the fundamental frequency of the PWM signal. Therefore, fc=1/(2πRC) and R=2πfc*C, which yields a 5 kΩ for a modulation frequency of 796 Hz.

The ground and VIN were provided by the microcontroller, which was either the Particle Photon (USB and Wi-Fi) or the Particle Argon (USB, Wi-Fi, BLE and enough RAM to perform on-board signal analysis). The power to the microcontroller was provided by USB or by a Li—Po battery which was connected to the appropriate power pin on the microcontroller board.

Transimpedance amplifier circuit. The amplification range of the TIA application note was fixed at 1 MHZ. The gain resistor was chosen to maximize the use ADC range in full so that the maximum phosphorescence signal (at 0 mmHg) would result in high bit counts but which would not saturate the ADC channel. With this resistor fixed at 2.5MΩ, and a desired amplification range of 1 MHz, the capacitor required was obtained from C≤2 πl which leads to C≤0.06 pF. We were able to find C=0.1 pF which means that the bandwidth is 636.6 kHz which is three of orders of magnitude higher than the modulation frequency (796 Hz). The DC and AC transfer function of the TIA is shown further below, showing the gain and bandwidth of the circuit.

TIA characterization: The following measurements were carried out on a prototyping board where the circuit was first built before designing the device PCBs. To characterize the DC transfer function, a constant source of illumination was moved at increasingly shorter distance on the photodiode. The current generated by the photodiode was measured by placing an ammeter in series with the photodiode, and the output of the TIA was measured by a voltmeter.

Figure 21B:
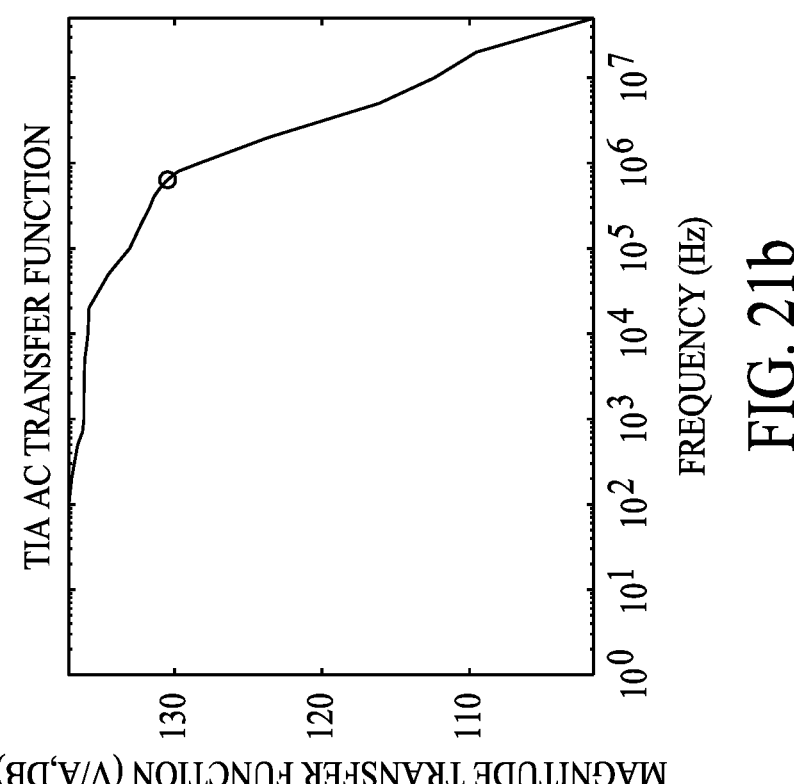
FIG. 21 shows graphs of a DC and AC transfer function of the transimpedance amplifier circuit.
Figure 21A:
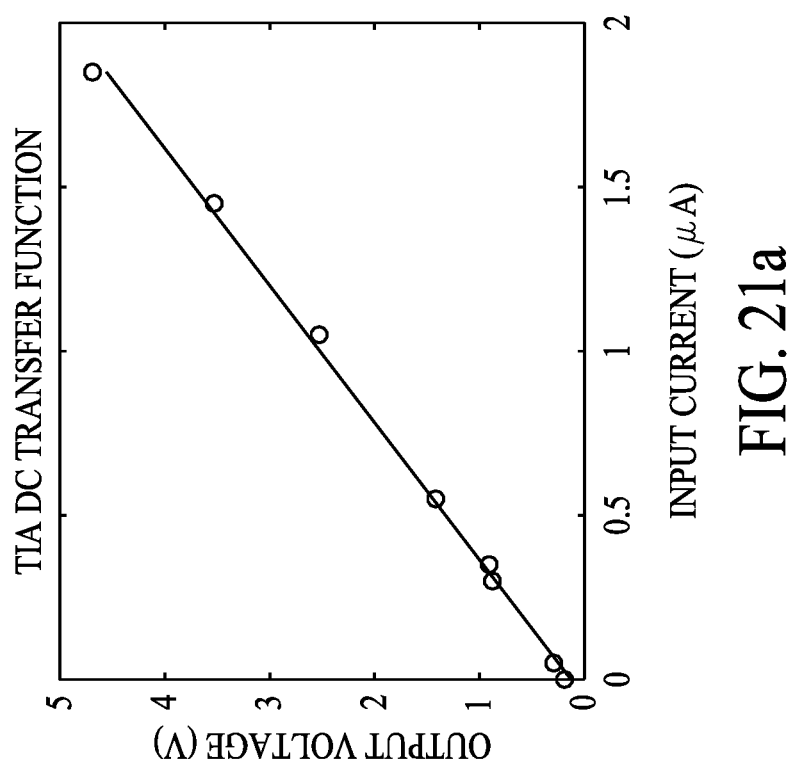
Figure 22:
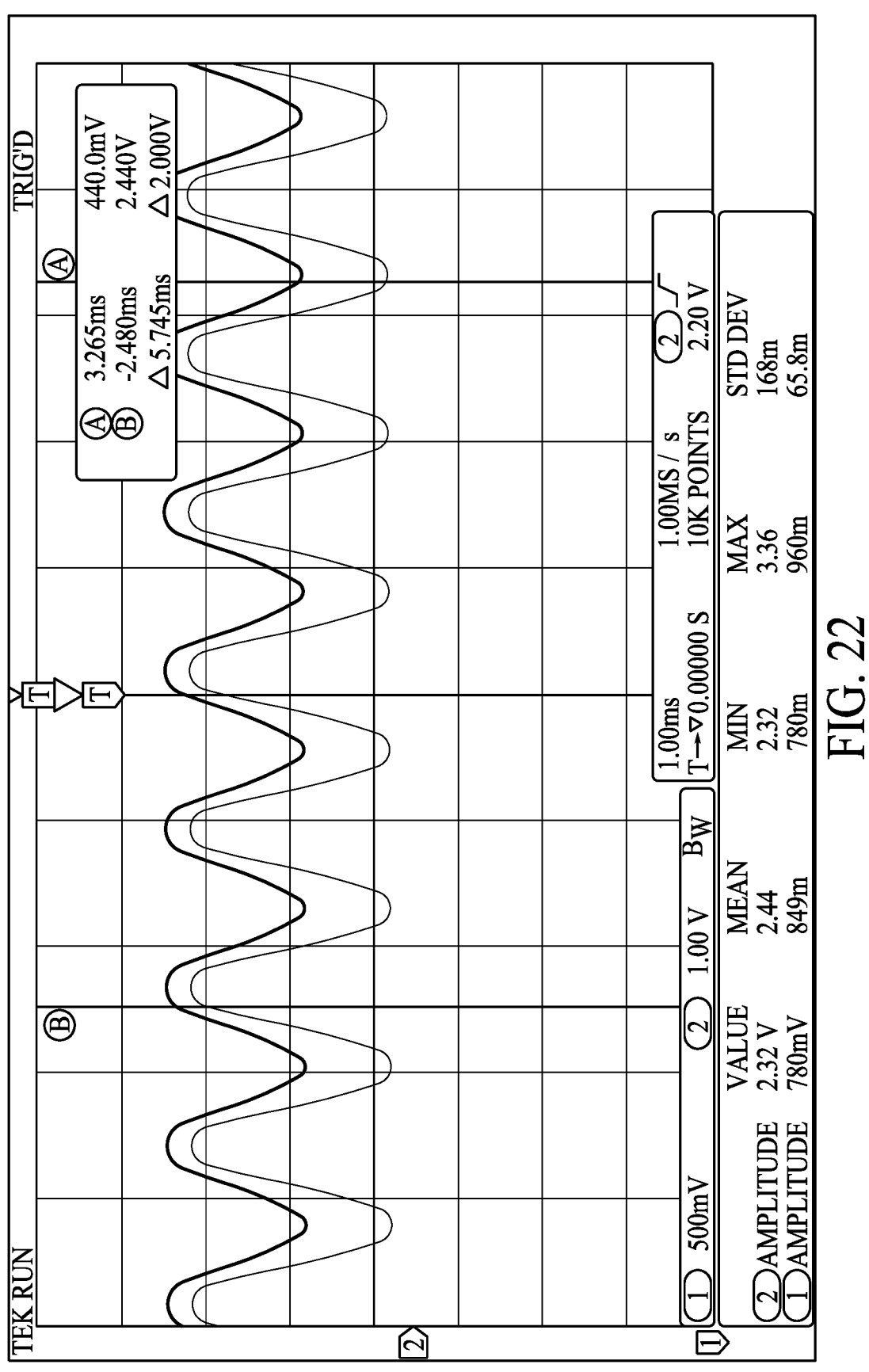
FIG. 22 shows input signals to the ADC, reference (the upper most curve) and photodiode (the lower most curve) measured by an oscilloscope.

FIG. 21 shows plots of the TIA experiment, which shows the expected linear dependence of output voltage with photocurrent. A linear fit reveals the voltage offset of the TIA is 0.130 V (100 mV per design) and the V/A gain is 2.4 MΩ, which is close to the value of the R6 resistor in the circuit schematic.

With regards to bandwidth, a previous design was followed to reproduce the 1 MHz photodiode amplifier characteristics for this device. To do this, once the sensor head was built with the optimal geometry (LEDs as close as possible to the photodiode), the gain resistor was tweaked on the circuit to be able to detect the optical signal from the oxygen-sensing film at an RG=2.5MΩ gain resistor (as opposed to 53.6 kΩ in ref), which amplifies a 1.92 μA current to 4.9V. In order to keep the −3 dB bandwidth at fp=1 MHz, room air (low signal) was needed to not saturate the amplifier at low oxygen (high signal). The capacitor C=1/ (2πRG fp)=0.06 pF. A 0.01 pF was purchased which brings fp=636.6 kHz. To characterize the AC transfer function, the schematic on page 14 of a Texas Instruments application note was followed and a Tektronix oscilloscope was used with built-in function generator and a photodiode simulator with a 2MΩ resistor chosen to produce a 0.25 μA current at the driving frequency which had peak-to-peak amplitude of 1 V. The amplitude of the output signal of the TIA was measured with the oscilloscope and is shown in FIG. 21 panel b in dB, using the equation dB=20 log 10(VOUT/IIN), where IIN=0.25 μA. As can be seen, a steep decline of the transfer function magnitude occurs for frequencies higher than fp=636.6 kHz (marked by a red dot)

ADC Inputs and Outputs. The input signals to the ADC can be seen in FIG. 22, measured by an oscilloscope, where the reference signal is shown in yellow and the photodiode signal in blue.

With regard to the output, if the analysis is not done on-board of the device, the following JSON string can be read through serial port (done in Python in our case):

{"temp":[28.35], "time":[1,282,564,845,1127,1412,1694,1975,2256,2544,2826,3107,

...,281619]

"voltage":[821,61,1061,2284,1607,118,379,2005,2200,634,71,1247,2307,1435,86,

...,979]

"tclk":[142,423,705,986,1267,1553,1834,2116,2397,2685,2966,3247,3529,3810,

...,281759]

"clk":[3072,3192,3756,3843,3321,3034,3492,3873,3579,3040,3245,3815,3803,3258,

...,3]}

Figure 23:
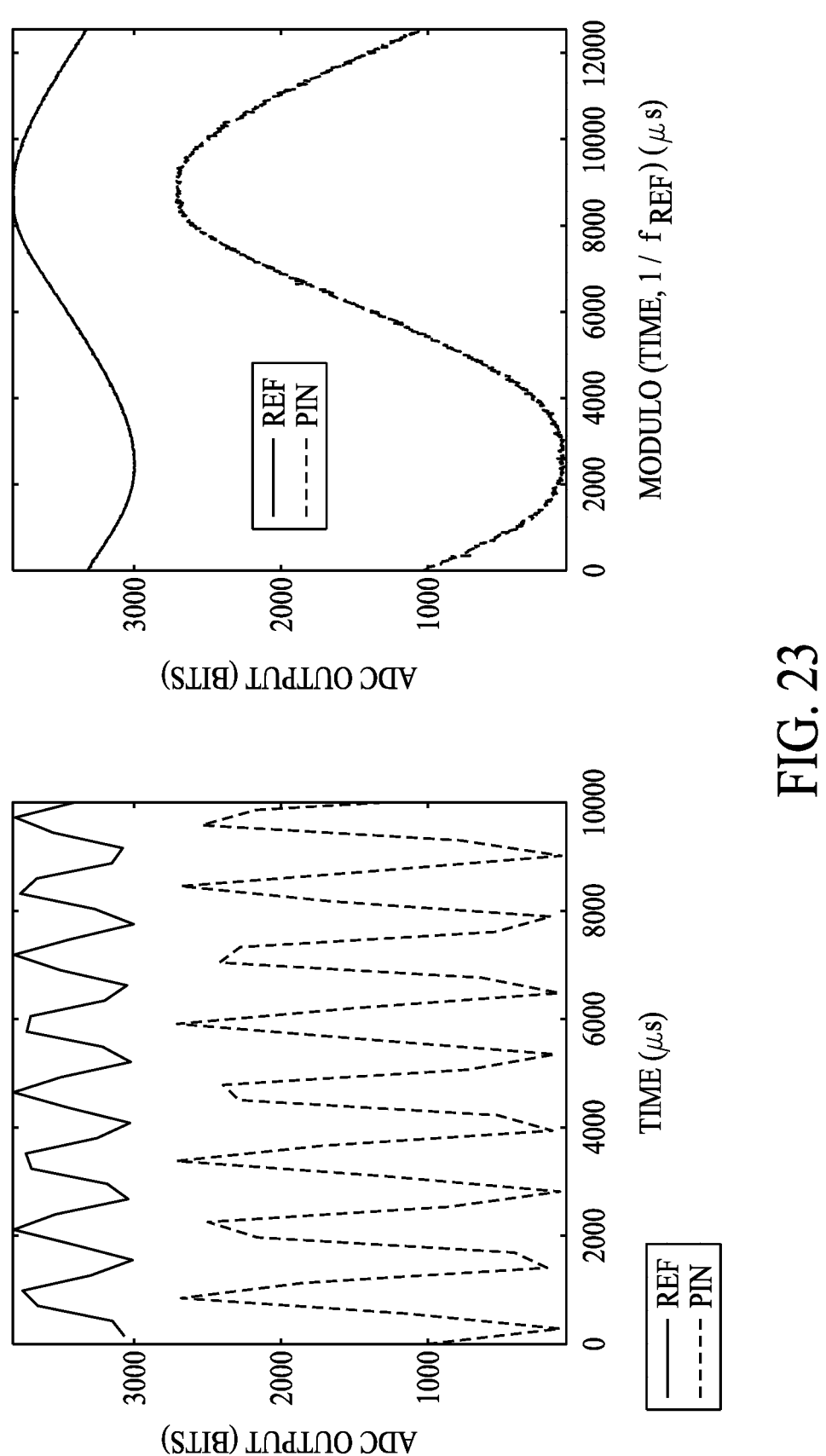
FIG. 23 shows a graph of output bits of ADC for the reference and photodiode channels, before (left) and after modulo operation (right).

The JSON string is parsed to extract the value of temperature, and the arrays of $t_{REF}$, $V^{ADC}$ and $t_{PIN}$, $V^{ADC}$ parsed_json=json.loads(line) temp=
parsed_json['temp'];
t=parsed_json['time'];
tclk=parsed_json['tclk'];
pin=parsed_json['voltage'];
clk=parsed_json['clk'];

The signals shown as bits in the Y scale are plotted in FIG. 23 (left and right).

To measure the power consumption, a USB power cable was modified to interrupt the current path and include an ammeter to measure the current. If the device is powered by USB (constant voltage source of V=5.17V), the following was measured a current of $I_{OFF}$=38 mA with LEDs OFF, and $I_{ON}$=108 mA with LEDs ON, so $P_{OFF}$=V $I_{OFF}$=196 µW and $P_{ON}$=V $I_{ON}$=558 µW. If a measurement is taken every $t_S$=5$_S$ and the LEDs are flashed for $t_{LED}$=0.2$_S$ every measurement, then the average power is P={$(t_S-t_{LED})$*$P_{OFF}$+$t_{LED}$*$P_{ON}$}/$t_S$=211 mW.

This device has not been optimized for power consumption, as the circuit scheme was designed for proof of principle, but its energy usage compares favorably to commercial wearable or portable devices, such as the Garmin Edge 800 GPS bike computer (1200 mAh and 15 h battery life, P=296 mW) or the Polar V800 triathlon watch (350 mAh and 13 h battery life, P=100 mW).

Figure 25A:
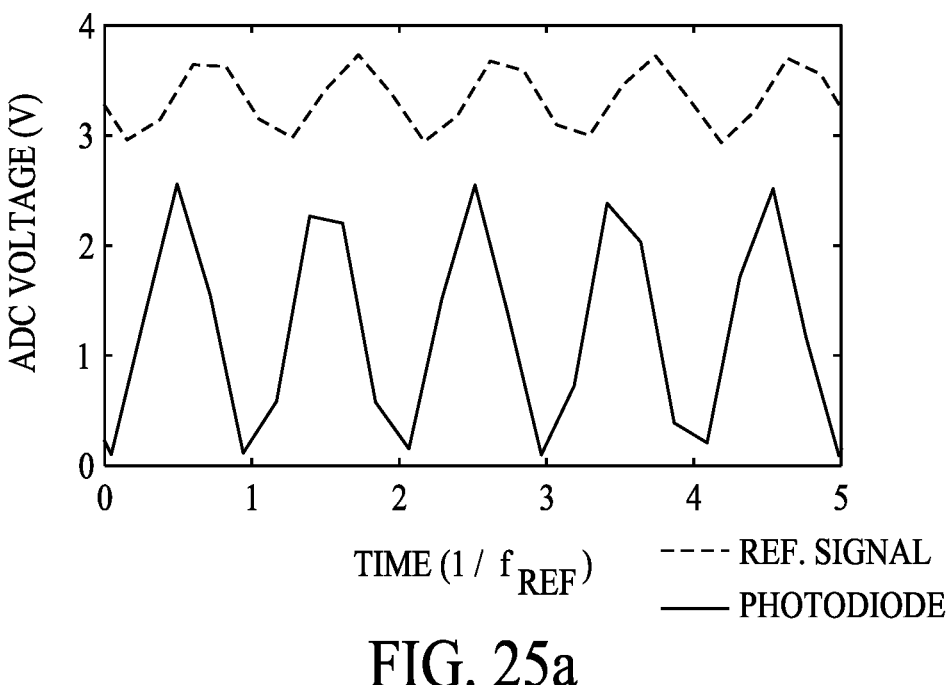
FIG. 25 shows panels a, b, and c. Panel a shows a photodiode and reference signal, with fr=796 Hz, sampled at 5 kHz. Panel b shows the photodiode and reference signal are sampled for 1000 points each, with time being plotted as the modulo with base 1/fr (the period of the reference signal). Because the signal does not change in this timescale (0.2 s), a single oscillation is able to be constructed from these signals with very high detail. Panel c shows a Fast Fourier transform of the reference and photodiode signals. The reference signal reveals the presence of odd harmonics, which leak from the PWM output through the low pass filter. The photodiode signal also contains even harmonics, which could originate from the non-linear nature of the LEDs.
Figure 25B:
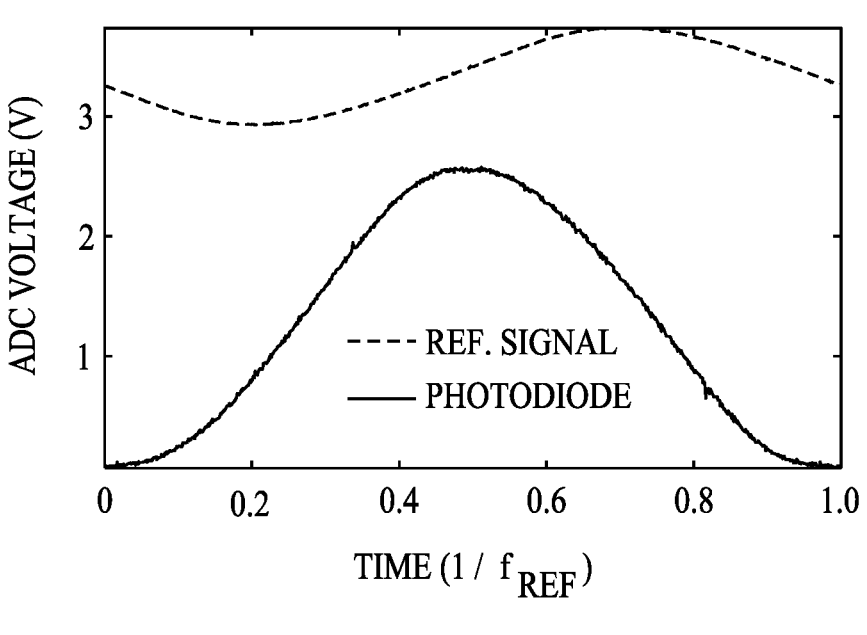
Figure 25C:
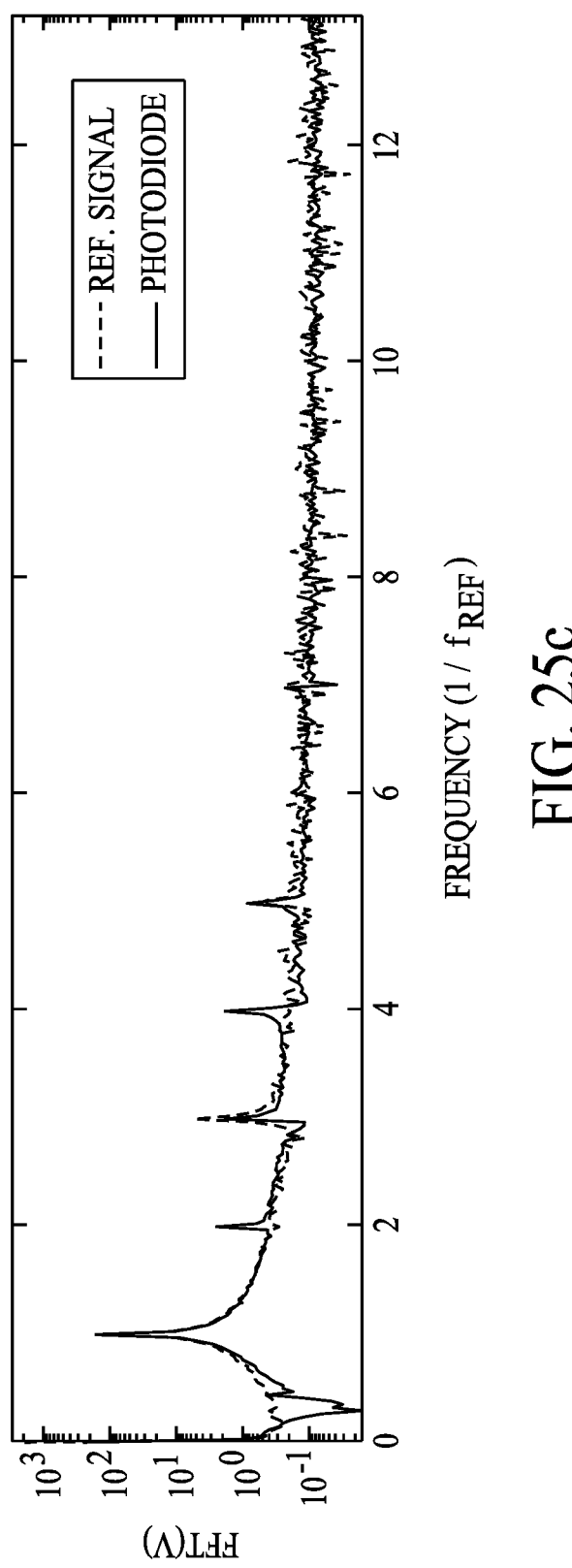
Figure 26A:
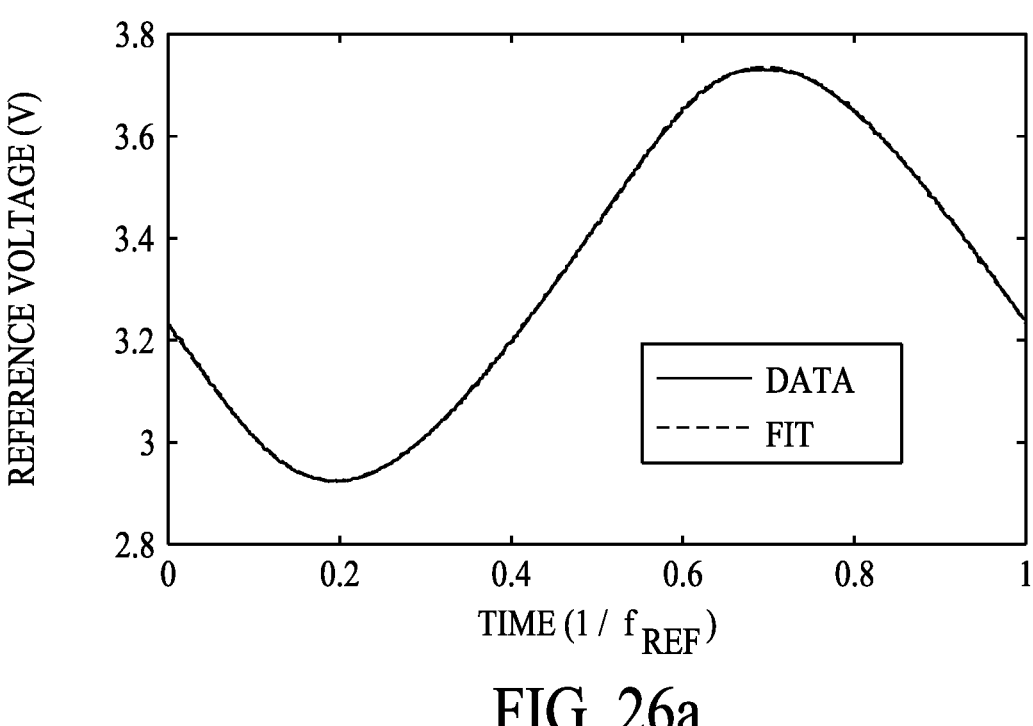
FIGS. 26a-d show the fitting of the photodiode and reference with a linear combination of sines. The reference frequency is fit with the fundamental frequency and harmonics 3f, 5f and 7f, with the photodiode requiring an additional 2f harmonics for a proper fit.
Figure 26B:
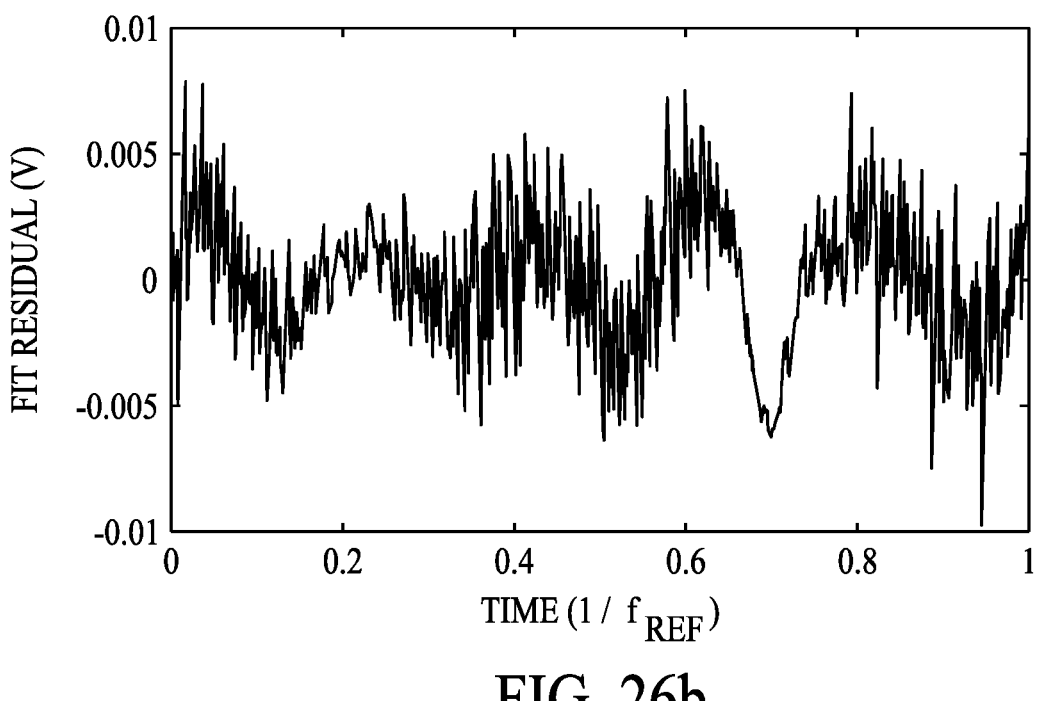
Figure 26C:
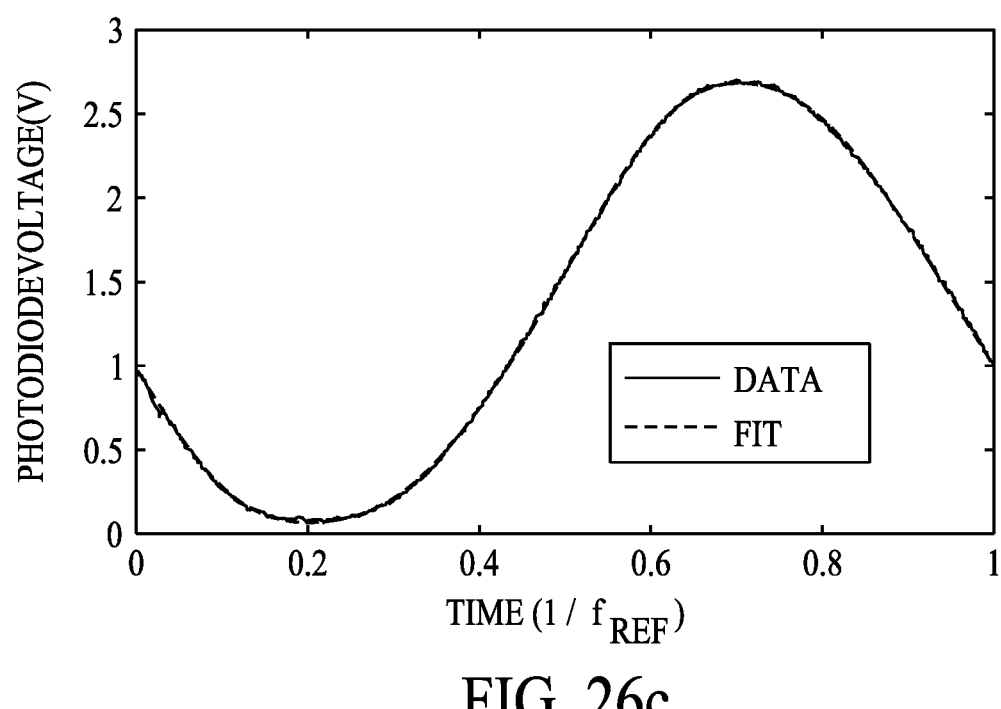
Figure 26D:
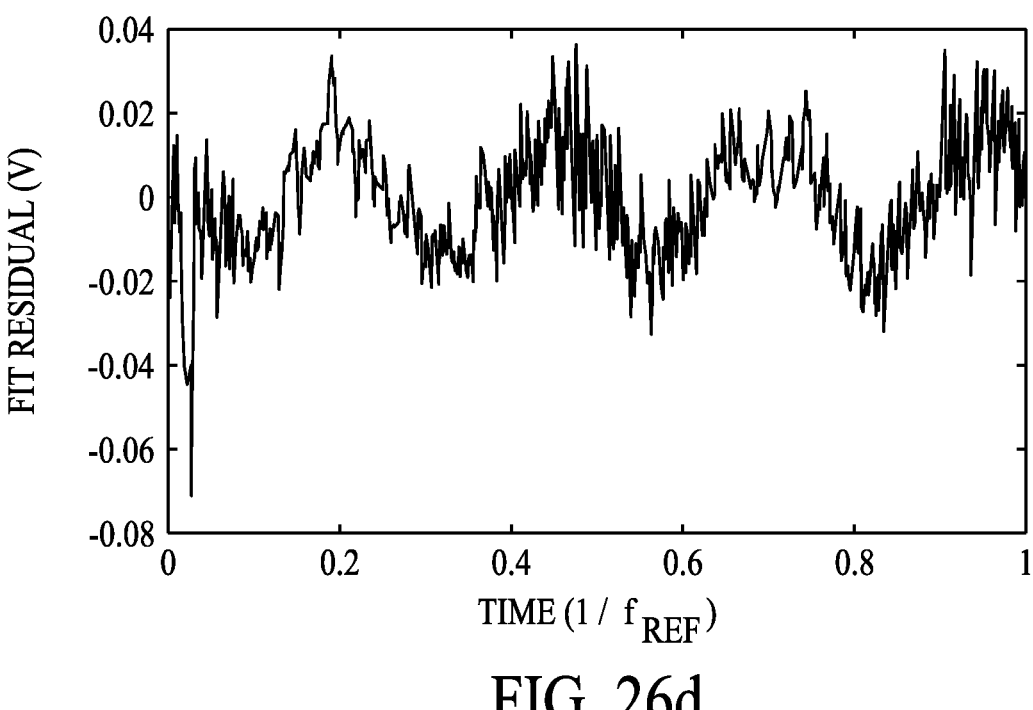

FIG. 25 panel a shows the photodiode and reference signal, with fr=796 Hz, sampled at 5 kHz. Panel b of FIG. 25 shows the photodiode and reference signal being sampled for 1000 points each, with time being plotted as the modulo with base 1/fr (the period of the reference signal). Because the signal does not change in this timescale (0.2 s), a single oscillation was able to be reconstructed for the signals with very high detail. Panel c of FIG. 25 shows a Fast Fourier transform of the reference and photodiode signals. The reference signal reveals the presence of odd harmonics, which leak from the PWM output through the low pass filter. The photodiode signal also contains even harmonics, which could originate from the non-linear nature of the LEDs.

With regard to signal processing, the conditioning of the reference signal is described (e.g., a 4-pole low pass filter and ×2 gain amplifying stage) and the circuit schematics shown above. The photodiode signal is directly fed into the TIA input and is not filtered through hardware. The signals plotted in FIG. 14 correspond to the ADC output channels for the photodiode and reference signal, and this numerical data does not undergo any filtering via software. The processes for extracting lifetime and intensity (linear regression in the matrix form) and for predicting pO$_2$ from lifetime and intensity are described, and this simplicity is where the beauty (or promise) of the approach lies.

The Octave or C++ code used to perform the signal analysis uses no other ingredients. The raw waveforms, the reconstruction of a single period using the modulo operator and the harmonic content of the signals is shown in FIG. 25. A result of the fitting is shown in FIG. 26.

A snippet of the Octave code to extract phase and amplitude from the photodiode signal is shown here:

```
t=mod(t,T); time modulo period T=1/f ref; [t,I]=sort(t);
    sort time ascending
x=x(I); sort photodiode voltage wrt time multiple linear
    regression in matrix form y=x;
ones=zeros(1,length(x))+1;
w=2*pi*ref_freq;
x1=cos(w*t-0.0*pi);
x2=sin(w*t-0.0*pi);
```

```
x3=cos(3*w*t);
x4=sin(3*w*t);
x5=cos(5*w*t);
x6=sin(5*w*t);
x7=cos(2*w*t);
x8=sin(2*w*t); M=[ones;x1;x2;x3;x4;x5;x6;x7;x8]';
p=inv(M'*M)*M'*y'; fitting coefficients
b0=[sqrt(p(2)^2+p(3)^2),sqrt(p(4)^2+p(5)^2),sqrt(p(6)
    ^2±p(7)^2),sqrt(p(8)^2±p(9)^2)];
amplitude of each harmonic phase=[acos(p(2)/b0(1)),acos
    (p(4)/b0(2)),acos(p(6)/b0(3)),acos(p(8)/b0(4))]; phase
    of each harmonic fitting function
fit=p(1)+p(2)*x1+p(3)*x2+p(4)*x3+p(5)*x4+p(6)*x5+p
    (7)*x6+p(8)*x7+p(9)*x8;
```

A thermistor's B value, or beta value, is an indication of the shape of the curve representing the relationship between resistance and temperature of a negative temperature coefficient (NTC) thermistor.

Figure 24:
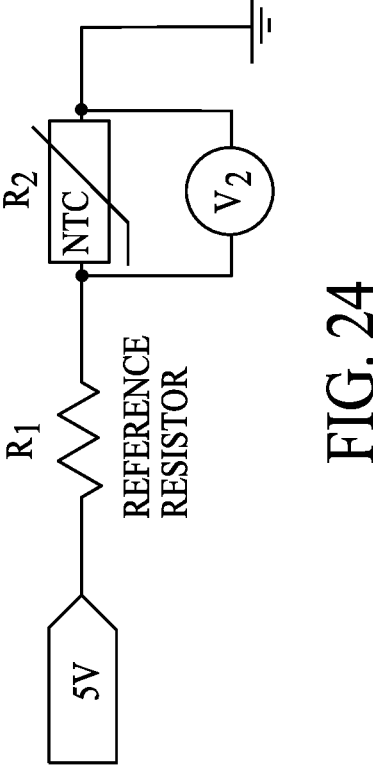
FIG. 24 shows a thermistor circuit.

A thermistor is defined by constant B between two temperatures, specified by the manufacturer, given by the Steinhart-Hart equation. In this case, B=3650, T1=25C+273.15=298.15K, and R(T1)=10 kΩ, so by measuring the resistance we can know the temperature by measuring the resistance at T2:

The resistance of the thermistor is measured by powering a circuit with two resistors, (reference resistor R1 and thermistor R2) in series with a constant voltage and measuring the voltage drop on the thermistor, as shown in FIG. 24. Because the voltage is known and one resistor is fixed, using Ohm's law the resistance of the thermistor can be calculated knowing T1=25.0+273.15, R1=5 kΩ reference resistor, R25° C.=10 kΩ; V=5V, so measuring V2 on the thermistor, we can substitute R2(T2)=VV2 in the Steinhart-Hart equation for T2 to calculate the temperature.

BLE communication. As is mentioned above, the multiple linear regression algorithm is implemented in the microcontroller. This allows to calculate the phase and amplitude of the signal on-board the device. The code uses the Matrix-Math.h Arduino library to perform the same calculations described above for Octave.

Then, every time the pO$_2$ is sampled, a custom BLE GATT protocol is used to transmit to a PC three quantities: {TEMPERATURE, PHASE, AMPLITUDE}. This is done through a Python script which uses the Bleak library and plugging in the device's Bluetooth MAC address and the UUIDs for the custom BLE services. From these three variables, and having previously performed a calibration of the oxygen-sensing film under use, the pO$_2$ in mmHg is calculated using the temperature-dependent Stern-Volmer equation.

The technique can be refined further by implementing the Stern-Volmer equation on the device's firmware and have the device output directly temperature and pO$_2$ values, but it was desired to save the values of phase and amplitude during these experiments. However, on most applications USB was used to measure as the "raw" waveforms could then be saved.

Example 2

Portable Oxygen-Sensing Device for the Improved Assessment of Compartment Syndrome and Other Hypoxia-Related Conditions Measurement of intramuscular oxygen could play a key role in the early diagnosis of acute compartment syndrome, a common condition occurring after severe trauma leading to ischemia and long-term consequences including rhabdomyolysis, limb loss, and death. However, to date, there is no existing oxygen sensor approved for such a purpose. To address the need to improve the assessment of compartment syndrome, a portable fiber-optic device for intramuscular oxygen measurements was developed. The device is based on phosphorescence quenching, where the tip of an optical fiber was coated with a poly(propyl methacrylate) (PPMA) matrix containing a brightly emitting Pt(II)-core porphyrin. The optoelectronic circuit is highly portable and is based on a microspectrometer and a microcontroller readout with a smartphone. Results from an in vivo tourniquet porcine model show that the sensor is sensitive across the physiological oxygen partial pressure range of 0-80 mmHg and exhibits an appropriate and reproducible response to changes in intramuscular oxygen. A commercial laboratory oxygen sensor based on a lifetime measurement did not respond as expected.

Figure 27:
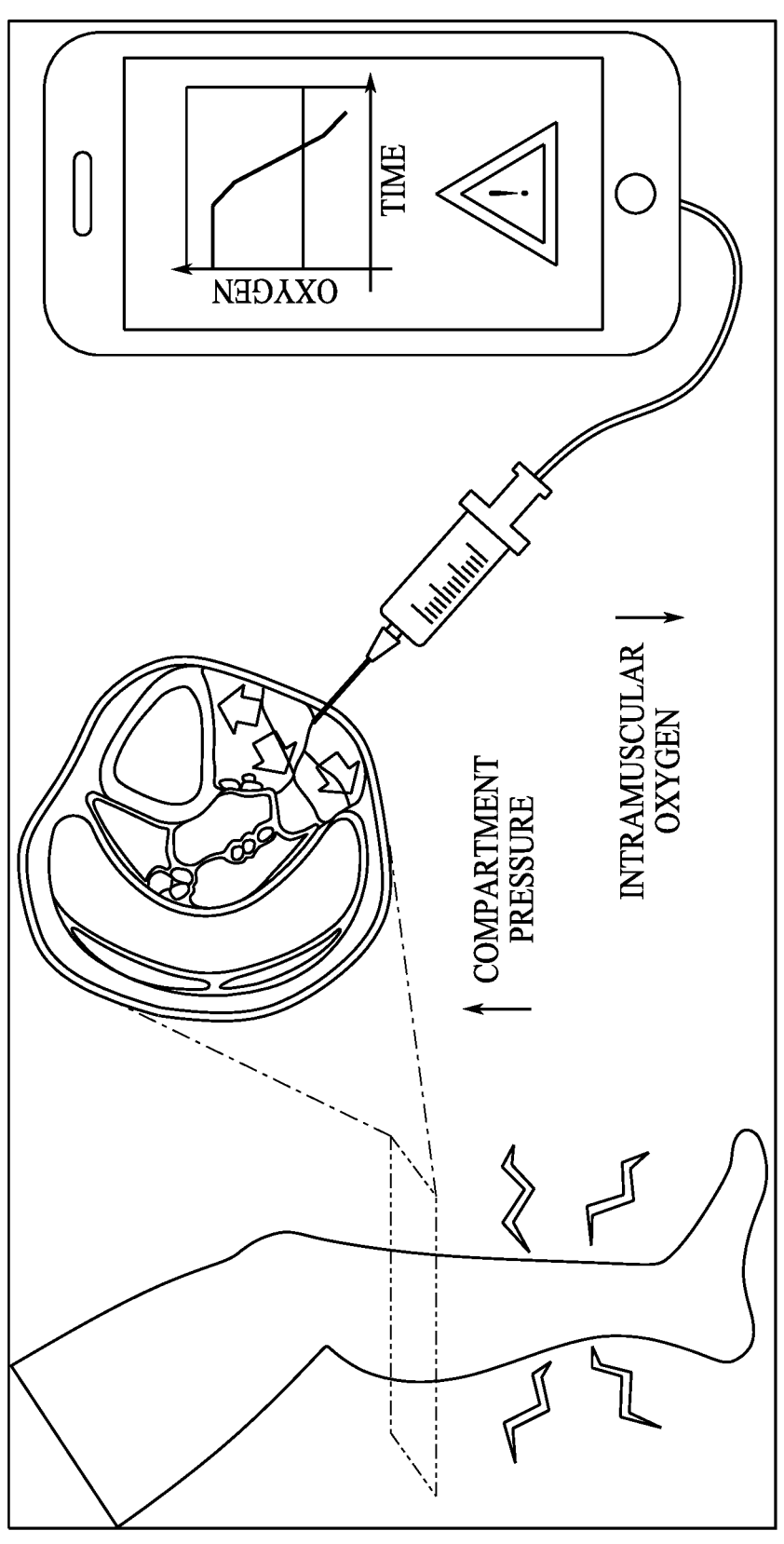
FIG. 27 shows a schematic illustration of an oxygen sensor system.

FIG. 27 shows a schematic illustration of an oxygen sensor system with an probe that responds to different levels of intramolecular oxygen (e.g., as a function of changing compartment pressure).

Acute compartment syndrome (ACS) is a condition where muscle ischemia occurs as a consequence of severe injury, which can arise from numerous forms of trauma. Previous studies found that tibia fracture, soft tissue injury, and radial fractures after traffic or sports accidents are the leading cause of ACS in civilian populations, although it can appear after nonaccidental causes like bleeding disorders or diabetes mellitus. ACS also plays an important role in military medicine when it occurs after polytrauma, blunt or crushing injuries from explosions, and tourniquet application. The condition mainly affects young men below 35 with an incidence of 7.3 in 100,000 male patients versus 0.7 in 100,000 for women.

The pathophysiology of ACS is described as an increase in pressure within the confined space of a compartment. The increased pressure results in a decrease in perfusion pressure that impairs blood supply and drainage, resulting in tissue hypoxia, tissue necrosis, and nerve damage. Since tissue necrosis occurs within 6-12 hours following hypoxemia, ACS should be treated immediately after diagnosis. Patients with ACS treated after the 6-12 hour time frame were shown to have a higher risk of developing worse clinical outcomes such as loss of function, amputation of the limb, or life-threatening conditions, which underscores the importance of early diagnosis of this condition.

Currently, the clinical standard treatment for compartment syndrome is a fasciotomy, where deep incisions are performed to release the pressure, resulting in severe scarring and chronic pain. The current diagnostic standard for ACS is focused on a neurovascular integrity assessment based on five clinical signs: pain, pallor, paresthesia, pulselessness, and paralysis. Pain out of proportion was observed to be the most important clinical sign; however, pain is not specific to ACS and can arise from other injuries. It is also worth noting that the communication of severe pain is not possible in unconscious patients.

In some cases, neurovascular assessment is complemented with a measurement of compartment pressure (CP) or perfusion pressure ($\Delta$p). CP measurements can be done using a simple arterial line transducer or with proprietary devices; for example, the C2Dx STIC pressure monitor (formerly the Stryker monitor) or the Millar Solid State Pressure Sensor. In practice, CP measurements are not widely used due to the high costs involved with the proprietary devices and the pain originating from the insertion of large (18 gauge) needles. In addition, CP was shown to have a low specificity of only 65% for ACS when $\Delta$p<30 mmHg. Thus, fasciotomies are often carried out prophylactically leading to unnecessary trauma, emphasizing the need for new diagnostic tools.

Previous studies summarized the many technologies that aim to improve the diagnosis of ACS and are currently under investigation, including monitoring localized oxygenation, monitoring of localized perfusion, localized metabolic analysis (glucose, pH), and systemic physiology based on serum biomarkers. Among all mentioned methods, monitoring of localized oxygenation attracted considerable attention. In principle, two variables are interesting: oxygen tension, i.e., the partial pressure of oxygen (pO$_2$) within the interstitial space, and oxygen saturation, i.e., the fraction of hemoglobin that carries oxygen relative to the total hemoglobin in the blood. To measure oxygen saturation, noninvasive near-infrared spectroscopy is widely used and was evaluated for ACS but was found to suffer severe limitations due to the small penetration depth and adverse influence from changes in the skin color. On the other hand, monitoring of pO$_2$ was found to have certain advantages over measuring pressure in the diagnosis of compartment syndrome in mice as well as canine models. The canine models studied previously have shown that measuring pO$_2$ had a high specificity and sensitivity for the diagnosis of compartment syndrome. One clinical study evaluated intramuscular oxygen measurements in patients with tibia fractures and found that pO$_2$ could be a good metric to reduce the number of unnecessary fasciotomies. Human data are very limited due to the nonavailability of suitable clinical intramuscular oxygen probes. The only probes currently approved (not for intramuscular measurements) and available for clinical use are Clark-type electrodes, which are severely limited by their long warm-up times (which is not suitable for an emergency setting) as well as frequent re-calibration, while they are also incredibly fragile, underscoring the urgent need for new clinical intramuscular oxygen probes Oxygen tension within tissue can be measured using a method known as phosphorescence quenching, where the collision of oxygen with specific phosphorescent molecules can be used to quantify oxygen concentration. Numerous oxygen-sensing molecules have been synthesized, with porphyrins being particularly useful for the measurement and imaging of tissue oxygen tension. Brightly emitting metalloporphyrin oxygen sensors have recently been synthesized that offer high-sensitivity oxygen tension measurements. When excited with blue ($\lambda$=377 nm) or green ($\lambda$=531 nm) light, these Pt(II)-core porphyrins exhibit red phosphorescence ($\lambda$=645 nm), which is inversely proportional to pO$_2$ according to the Stern-Volmer relation where k is the Stern-Volmer quenching constant and I$_0$ is the intensity of the phosphorescence in the absence of a quencher (oxygen). The bright red light from these new porphyrins can be seen by the naked eye and quantified with the help of portable imaging equipment. These new porphyrins have been clinically validated as part of liquid bandages for the assessment of wound healing and integrated into wearable devices for performance monitoring.

Further development of the above-mentioned portable technology into a toolkit for sensing the loss of deep-tissue oxygenation associated with compartment syndrome is described herein. This was accomplished via the integration of an oxygen-sensing material with optical fibers and hypodermic needles or catheters.

To date, there is no medical device available for the clinical measurement of intramuscular oxygen. This might be due to the fact that most existing sensors were not designed to measure oxygen under physiological conditions in a clinical setting, require expensive and oversized readout devices, and many of these sensors have also not been evaluated beyond limited in vivo models. For example, the OXY-MICRO-AOT from World Precision Instruments was evaluated in surgically exposed epididymal fat pads, whereas the oxygen micro-sensor from PreSens was evaluated in tumors on the chorioallantoic membrane of chick embryos. Also, intra-vascular sensors such as the discontinued Paratrend are not directly applicable to an intramuscular oxygen measurement where insertion force is applied to the sensor. The oxygen-sensing device described here could be especially useful to assess not only ACS but also other pathological conditions, such as vascular diseases, diabetic wounds, burns, cancer, and traumatic injuries that can result in a reduction of tissue $pO_2$ leading to hypoxia.

Materials. To synthesize an optimally performing material for optical fiber-based deep-tissue oxygen sensing, a variety of compounds and formulations were tested. The primary goal was to find a biocompatible host matrix material that would also be chemically compatible with the metalloporphyrin molecules so that aggregation can be avoided. The resulting oxygen-sensing material would need to display high $pO_2$ sensitivity in the physiological range of 0-80 mmHg under humid conditions while being insensitive to changes in pH. Furthermore, the material was required to adhere well to the tip of small-diameter optical fibers. Developing a material and coating process compatible with small fiber diameters was critical, as the goal was to ultimately use needles of the smallest gauge possible to limit patient discomfort. In addition, it was important to keep the fiber preprocessing as simple as possible to facilitate the rapid translation of the device to both military and civilian patients. For this purpose, four different matrix materials were investigated: tetraethyl orthosilicate (TEOS) sol-gel, 3M Cavilon™ film formulation, poly(ethyl methacrylate) (PEMA), and poly(propyl methacrylate) (PPMA).

Figure 28:
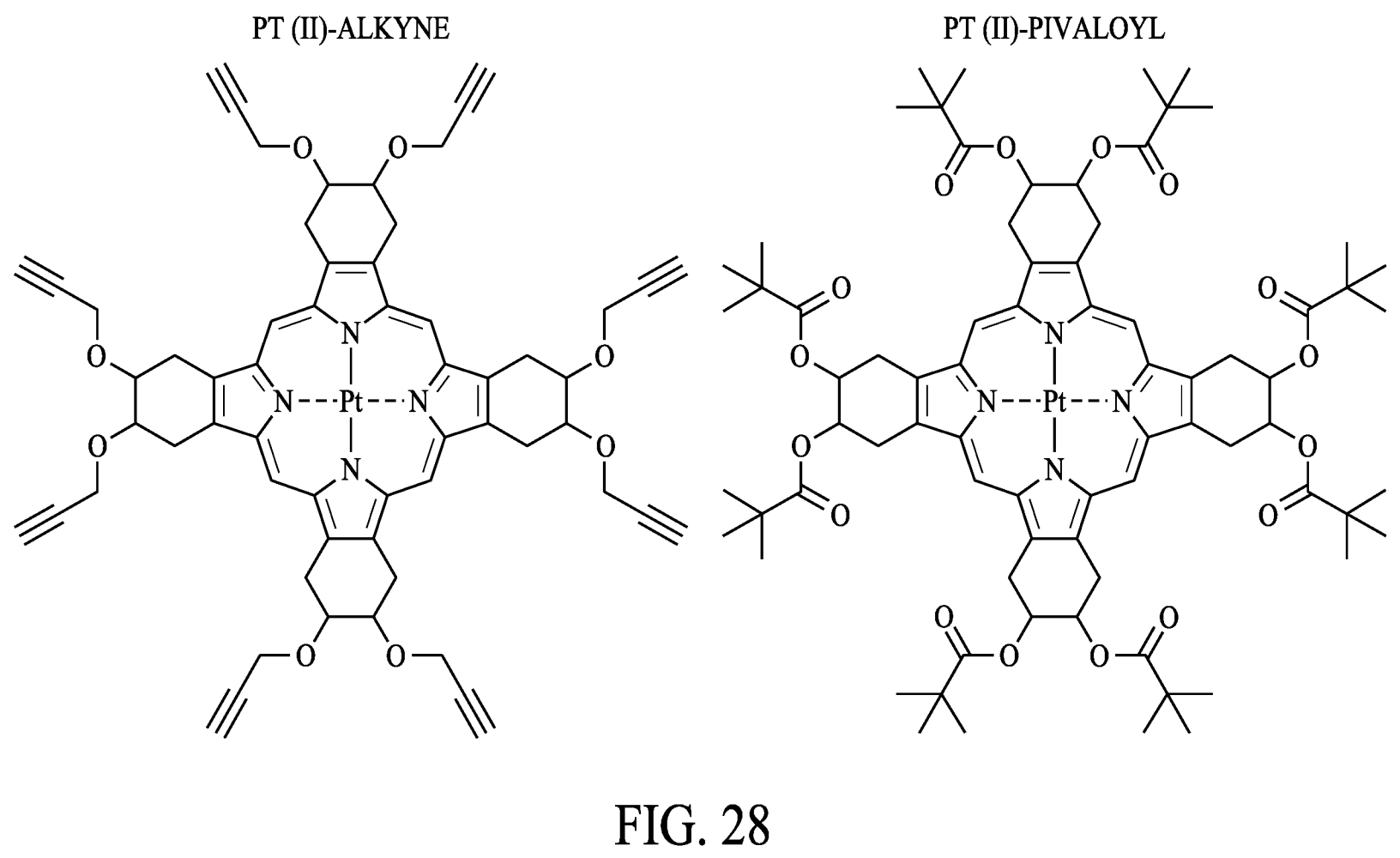

Due to its noted compatibility with porphyrins and humidity insensitivity, tetraethyl orthosilicate (TEOS) sol-gel is a strong candidate material. TEOS-containing matrices have been used before to produce spin-coated as well as fiber-based oxygen sensors using commercially available ruthenium and platinum complexes. However, the fibers used in these references all had large diameters of x greater than or equal to 550 μm, incompatible with small-bore needles, or the fiber tip was further processed, for example, by tapering to increase the signal strength. In addition, ruthenium complexes are not suited for in vivo applications due to their toxicity. For the current work, TEOS formulations containing 50 μM of the alkyne-terminated Pt(II) porphyrin previously developed in-house were prepared in a similar fashion to previous procedures. In-house synthesized porphyrin derivatives were chosen for this work due to the familiarity with their properties and their performance across different materials. Furthermore, it has been established that synthetic protocols for their derivatization can be used in future immobilization within matrix materials, either by chemical attachment or photo-crosslinking. The alkyne-terminated porphyrin, whose molecular structure is shown in FIG. 28, was synthesized.

TEOS, 1-octanoyl-rac-glycerol (referred to as polyol), and dimethyl sulfoxide (DMSO) were purchased from Sigma-Aldrich. Ethyl alcohol and hydrochloric acid were purchased from Fisher Scientific. For a 50 μL TEOS/porphyrin formulation at pH 1, a solution of TEOS, and a solution of the polyol and the porphyrin were prepared in two separate, small Eppendorf tubes. In the first tube, 12.5

μL of TEOS (25 wt. %) was added to 15 μL of DMSO followed by the addition of 1.7 μL of 1 M hydrochloric acid in ethanol solution. Here DMSO was used instead of ethanol to increase the surface tension. In the second tube, 5 mg of the 1-octanoyl-rac-glycerol (10 wt. % polyol) was mixed with an aliquot of the alkynyl metalloporphyrin stock solution in dichloromethane (DCM), and ethanol was added to bring the combined volume of both tubes to 50 μL. After vortexing, the polyol solution was added to the TEOS tube, vortexed again, and was left to sit for 15-20 minutes. To reduce cracking, additional formulations were made where surfactants of different amounts (1.4 and 2.8 wt. % of Triton X-100 and Tween-20) were added.

The second material investigated for the purpose of coating optical fibers was the terpolymer-based 3M Cavilon™ No Sting Barrier Film. 3M Cavilon™ film is an FDA-approved liquid bandage, is water-resistant, adheres well to various surfaces, and is breathable. The Cavilon™ film formulation includes hexamethyldisiloxane, isooctane, acrylate terpolymer, and polyphenylmethylsiloxane copolymer. Since Cavilon™ film is hydrophobic, it was found immiscible with the alkyne-terminated porphyrin. Instead, the much more hydrophobic pivaloyl-terminated derivative was used, which displayed good miscibility. The Pt(II)-pivaloyl-terminated porphyrin was synthesized. For the final solution, 3M Cavilon™ film formulation was vortexed with the pivaloyl-terminated porphyrin in an Eppendorf tube.

In addition to TEOS sol-gel and Cavilon™ film, PEMA and PPMA were investigated for use with the pivaloyl-terminated porphyrin. These acrylate polymers together with poly(methyl methacrylate) (PMMA) were investigated previously for the purpose of coating the tapered tip of 480 μm fiber oxygen sensors. They showed that PPMA had higher sensitivity and faster response time than PEMA and PMMA. Previous configurations combined a PtOEP phosphor with PEMA and coated 600 μm optical fibers.

For coating the 200 μm fibers to produce the sensor described in this publication, a solution was made as follows: in an Eppendorf tube, 0.25 mg/μl PEMA or PPMA (purchased from Sigma-Aldrich and Scientific Polymer Products) was dissolved in DCM. After vortexing, the pivaloyl-terminated porphyrin was added at a concentration of 50 μM and the solution was vortexed again. While higher and lower concentrations of PEMA and PPMA were also tested, the coating materials made from solutions at a concentration of 0.25 mg/μl were found to display the largest oxygen-sensing response.

To prevent the direct contact of the oxygen-sensing material with bodily fluids and to shield the material from external light, all fiber tips were additionally coated with a breathable, reflective white layer. The coating had the advantage of increasing the measured porphyrin emission signal due to back-reflection and protecting the oxygen-sensing layer during a future sterilization process using ethylene oxide (EtO). EtO sterilization is used as the standard method to sterilize biomedical sensors since it has been shown to have no damaging effects on polymer coatings and silica fibers. The protective coating for the oxygen sensor contained a white pigment based on 40% titanium dioxide and silicone. To prepare it, 0.1 g of a dimethylsiloxane copolymer (Gelest, CAS 68037-59-2) and 1 g of white pigment concentrate (Gelest, PGWHT01) were mixed together in an Eppendorf tube. Subsequently, approximately 0.3 g of cure retarder (Gelest, Utensil R1) and a small drop of platinum catalyst (Sigma Aldrich, CAS 68478-92-2) were added, and the solution was stirred vigorously. The combination of the cure retarder and catalyst resulted in a mixture that lasted for approximately 10 minutes before solidifying, providing ample time to coat the fiber tips.

Fabrication of the Fiber Sensors. Multimode silica fibers with a 200 μm core (Thorlabs, FP200URT) were cleaned with isopropyl alcohol, and the ends were stripped and cleaved. For the TEO S-based coating, the fiber tip was functionalized either by plasma treatment (BD-20AC plasma treater) or by silanization (1 wt. % aminopropyl triethoxysilane in water solution) immediately before coating to improve the adherence of the TEOS sol-gel layer. The fibers were dipped in the silane solution for 10 min and were then dried at 120° C. for a period of 2 hours. Subsequently, the fiber tips were dipped (1-5 times) by hand in the TEOS solution. Dipping the fiber several times increased the thickness of the layer and thus improved the signal strength. After dipping, the fibers were left to dry overnight and were then placed under high vacuum for 2-3 hours the next morning.

For the Cavilon™ film formulation as well as the PEMA and PPMA matrices, the fibers were not functionalized before coating. A drop of porphyrin-matrix solution was transferred from the Eppendorf tube to the surface of a poly(dimethylsiloxane) (PDMS) film, and the fibers were dipped by hand in the porphyrin-matrix solution. The fibers were left to dry overnight and were subsequently placed under a high vacuum for 2-3 hours. After coating with the oxygen-sensing layer, the fibers were dipped in the white silicone coating, then dried with 100° C. hot air for 10-15 seconds, and were finally left to dry for 48 hours at room air. To strengthen the adherence of the silicone layer and prevent it from detaching from the fiber, an additional protective layer of 3M Cavilon™ film was coated on the fiber.

Figure 29:
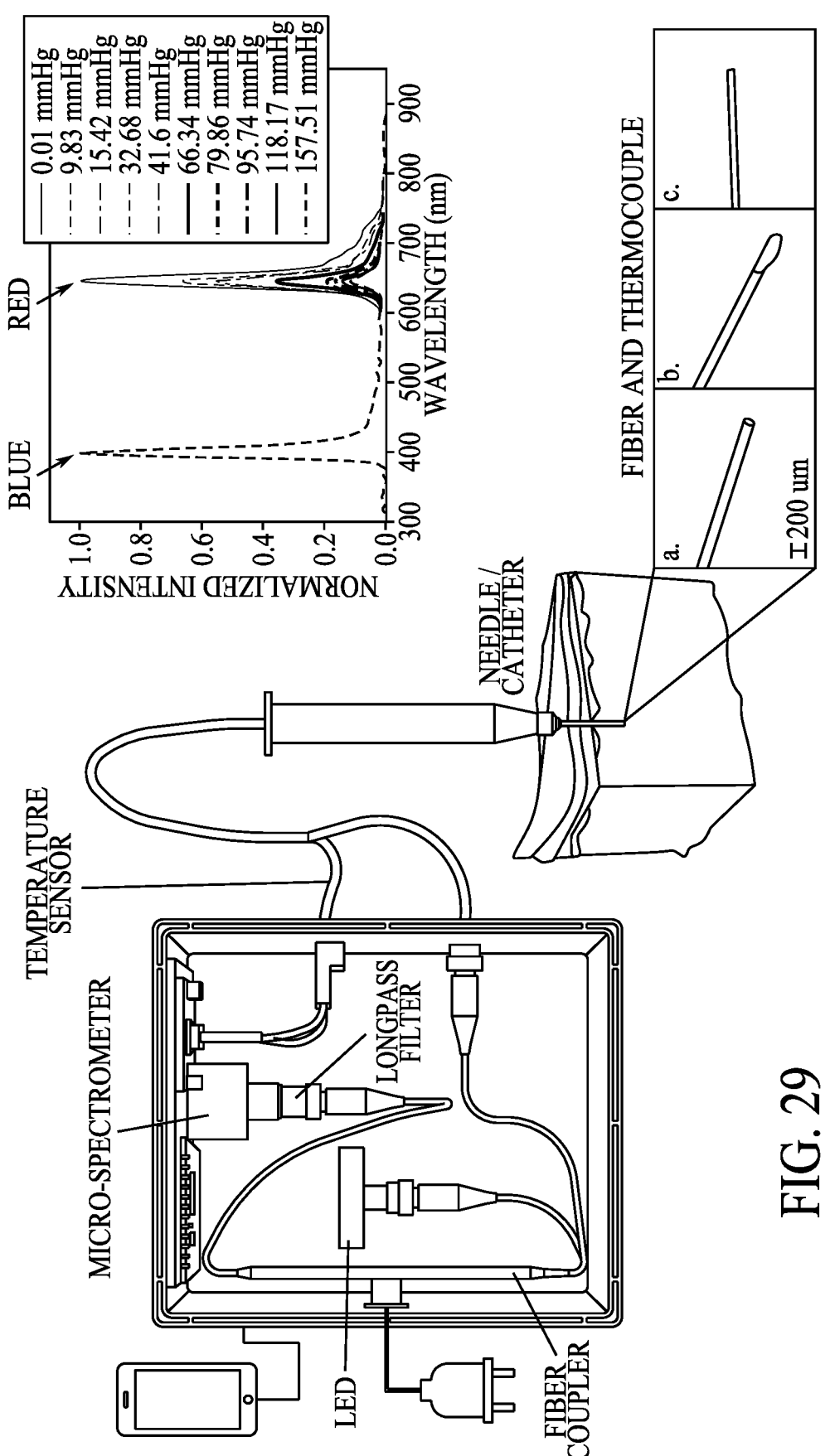
FIG. 29 shows a schematic illustration of the prototype device (10×11 cm, weighing 200 g).

Apparatus and Data acquisition. Optical and electronic hardware was fitted inside a 10×11×4.5 cm3 3D printed box, as shown in FIG. 29. For the measurement of oxygen concentration via changes in phosphorescence intensity, a Hamamatsu C12880MA-10 microspectrometer was connected to a custom printed circuit board (PCB) for readout and for driving the LED source (Thorlabs, LED375L). The PCB was connected to a Particle Photon microcontroller and an external 12 V power supply to provide stable voltage. A solely USB-based power supply was found not to be stable for both pulsing the LED and reading out the microspectrometer simultaneously. The firmware for the photon microcontroller was custom-built on the base of an Arduino sample code.

For measurement of oxygen concentration via changes in phosphorescence lifetime, an avalanche photodiode can be used and has been shown to detect the emitted phosphorescence transported by the fiber. An avalanche photodiode (e.g. Thorlabs APD130A or APD440A) is outfitted with a fiber coupler and the fiber end is directly coupled to the avalanche photodiode for the detection of the red phosphorescence. A variable gain avalanche photodiode can be used as well. In addition, flexible optical filters such as the ones described in the prior example can be added to the system to filter out light outside the phosphorescence bandwidth, or optical fiber filters (e.g. a Bragg grating) can be implemented for the same effect. The excitation light from a UVA LED is coupled into the fiber via a ³/₃₂ inch diameter glass bead.

The 375 nm excitation light as well as the 650 nm phosphorescence light was guided through a 1×2 fiber-optic coupler (Thorlabs TH200R5S1B). On the detector side of the coupler, a piece of a flexible UV filter from Edmund optics (#39-426, 400 nm longpass) was glued to the SMA connector to reduce the contribution from the blue light, which was otherwise saturating the spectrometer. An SMA-to-FC/PC mating sleeve (Thorlabs ADAFCSMA1) was mounted in the wall of the box where the fiber-optic sensor was connected.

The base for the fiber-optic sensor was an FC/PC connectorized custom fiber-optic patch cable from Thorlabs with a 200 μm core and 0.5 NA (FP200URT). The patch cable was cut, and the tubing was removed from one side, and prepared and coated as described earlier. Together with a 24-gauge thermocouple (IT-24P, physitemp), the coated fiber was integrated into two different versions of the device. In the first version, the fiber was glued into an 18-gauge needle (BD PrecisionGlide), shown in FIG. 30. To allow for adequate equilibration with the surrounding tissue, two 1 mm side ports were drilled into the fiber 5 mm above the tip. The holes were at the same height and separated by 180°. To prevent the fiber tip from breaking when inserted into tissue, the needle tip was closed using light cure medical device adhesive (Loctite 3321). A 1 ml syringe body (HSW NormJect Tuberkulin) was used to provide stability and easier handling to the fiber sensor. It should be noted that the 200 μm fiber could fit in a smaller gauge needle in the future, and the 18-gauge needle was only selected for accuracy in creating the side-port holes. In the second version of the device, the fiber was integrated into a flexible polyethylene tubing with an outer diameter of 0.6 mm, and a luer connector was added to ensure tight mounting in a standard catheter. The length of the tubing was chosen in a way that the oxygen-sensing part would peek out of the tip of a standard 20-gauge catheter (Exel Safelet catheter, 20G× 1¼") when the luer was locked in place.

The LED pulsing time as well as the time between measurements were adjusted to the signal intensity of the different coatings using software settings. For the final device, a pulsing time of 5 ms and a measurement interval of 15 seconds were used. The microcontroller was read out via a USB cable using a smartphone. A USB connection was chosen over a wireless connection to add an additional layer on data safety when dealing with clinical data. An android smartphone application was developed with the help of Google's Flutter software development kit (SDK) and Android Studio. The application provided the option to change the settings such as pulsing time, measuring interval, output file name, and $pO_2$ calibration. Besides the current spectra, the application displayed the $pO_2$ timeline and provided the option to store the data file in a text format on the SD card of the smartphone.

For calibration and testing purposes, the oxygen sensor was placed in a small gas chamber alongside a commercial laboratory oxygen sensor (Profiling Oxygen Microsensor PM-PSt7, PreSens), which provided an independent readout of the chamber $pO_2$. The temperature of the gas chamber was adjusted with the help of a hot plate. The oxygen partial pressure in the chamber was adjusted between 0 mmHg and 160 mmHg by changing the relative flows of nitrogen and air with the help of a gas mixer. The humidifier allowed for the system to be switched between dry and humid conditions.

To extract $pO_2$ from the data, a nonlinear least-squares fit was used, which was based on a two-dimensional Stern-Volmer relation containing a linear dependence on temperature where f accounts for the phosphorescence from the porphyrin molecules nonaccessible by quenchers, kT is the temperature-dependent quenching constant, and TC is the room temperature at which the calibration was performed. The intensity I was extracted from the spectrum by integrating the red spectral range and normalizing it to the blue excitation light. The linear temperature dependence was verified by sweeping through temperatures at fixed values of pO$_2$. pO$_2$ and temperature were changed in both directions, and no significant hysteresis effects were observed.

$$I = \frac{I_0}{1(k_0 + k_T(T - T_C))[pO_2]} + f \qquad (5)$$

Figure 31:
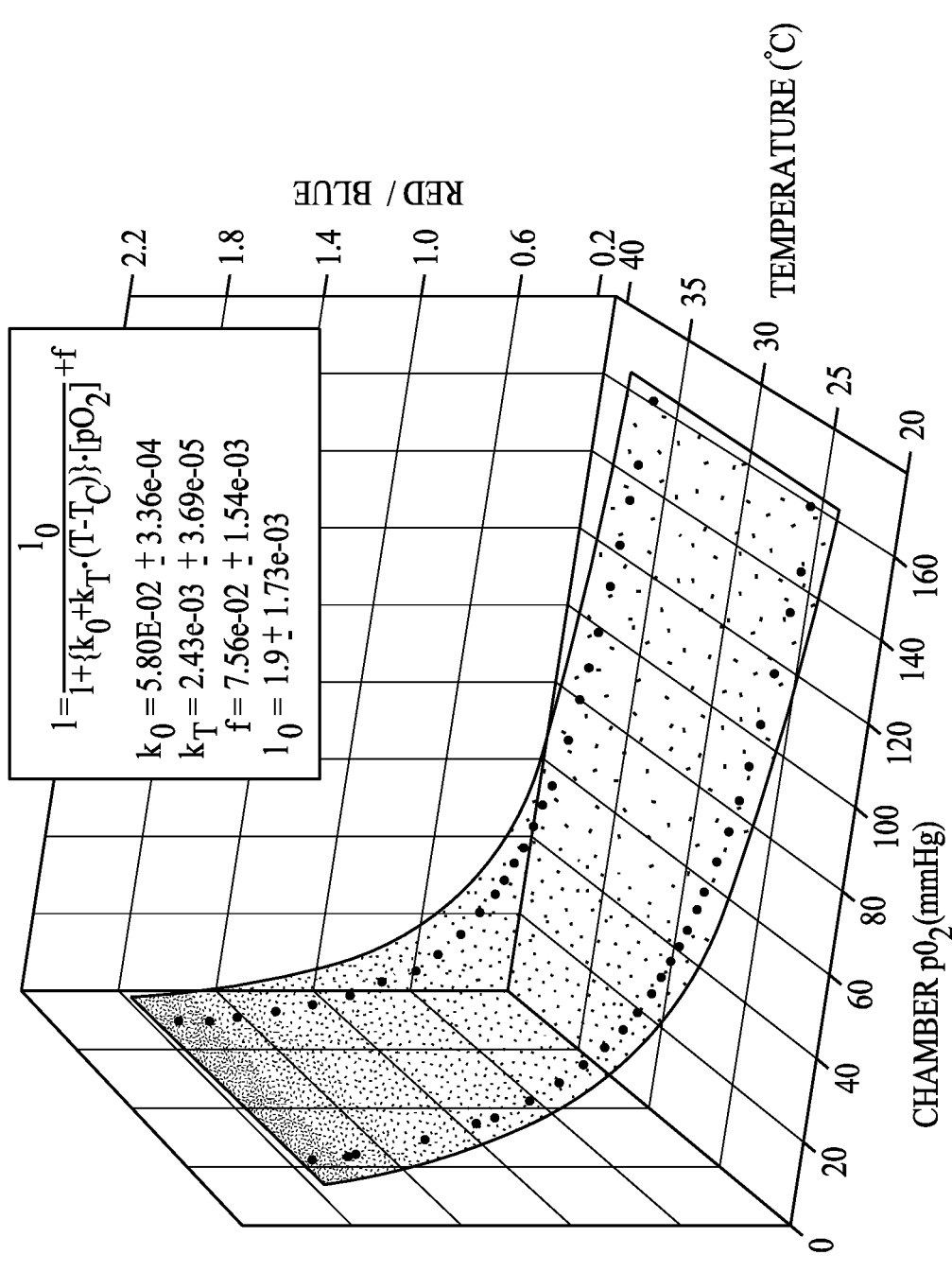
FIG. 31 shows a 2D calibration obtained from a Pt(II)-pivaloyl in PPMA-coated fiber. I is the intensity of the phosphorescence (red/blue), $I_0$ is the phosphorescence at zero oxygen, T is the temperature, TC is the calibration temperature from the 1D calibration, $k_0$ and $k_T$ are the temperature-independent and temperature-dependent Stern-Volmer quenching constants, respectively, and f accounts for the phosphorescence from the porphyrin molecules non-accessible by quenchers.

The resulting two-dimensional calibration plot for a fiber coated with the PPMA matrix is shown in FIG. 31. By extracting the fit parameters I0, k0, and kT, and knowing the calibration temperature TC, pO$_2$ was deduced from equation 5. The corresponding pO$_2$ errors were calculated from the same equation using Gaussian error propagation and the parameter fitting errors. The error for the laboratory oxygen sensor was 3% and the error of the temperature sensor was 1° C.

The resulting pO$_2$ response matched the design requirements in the physiological range between 0 and 80 mmHg where errors were smaller than 5%. At higher pO$_2$ values, the errors increased to approximately 6%. This was expected, as the porphyrin emission intensity decreases with increasing pO$_2$. In the future, this could be improved by adding a second porphyrin or porphyrin-containing material that is tuned to be more sensitive at higher values of pO$_2$.

Porcine Model. To assess the performance of the sensor under realistic conditions, two sets of in vivo experiments were performed in two Yorkshire swines and one Hampshire swine, with all swine being female. The similar anatomic scales between swine and humans make the porcine model an especially suitable model to study physiological changes in intramuscular oxygenation. The animal protocol was reviewed and approved by the Institutional Animal Care and Use Committee at Massachusetts General Hospital, and all procedures were performed within the Knight Surgical Facility. The conducted study was a pilot study and was meant to gather meaningful but not statistically significant data. For all pigs, anesthesia was induced with intramuscular telazol (4.4 mg/kg) and atropine (0.4 mg/kg), followed by an isoflurane (1-3%) inhalation. During the entire procedure, the pigs were ventilated with a Fraction of Inspired Oxygen (FiO$_2$) of 1, which is the standard procedure for pigs at Massachusetts General Hospital. In previous experiments, ventilation at lower FiO$_2$ was seen to lead to a decrease in blood oxygen saturation due to shallow breathing under anesthesia of these animals. To prevent hypoxia-related conditions, the standard protocol at FiO$_2$=1 was used. The pigs for the current study were an on-table transfer from another protocol and had undergone previous procedures related to different laser skin treatments.

In the first experiment, limb oxygenation following the loss of cardiac function was measured in a pig. The oxygen sensing needle prototype was sequentially inserted into several regions of the pig's hind limb at the biceps femoris muscle 1 minute following euthanasia via administering pentobarbital euthanasia solution (Fatal Plus), as shown in FIG. 30.

In the second in vivo experiment, limb oxygenation following the placement of a tourniquet was measured in two pigs. A tourniquet was applied for 30 minutes to the front limb of two pigs above the elbow joint over the Tricheps Brachii and Brachialis muscles, as shown in FIG. 30. Due to the conical shape and the shortness of the pig leg, a standard pressurized tourniquet could not be used; instead, a RATS GEN 2 tourniquet was applied over a rubber tourniquet (SWAT-T) and tightened by hand.

50

Figure 30:
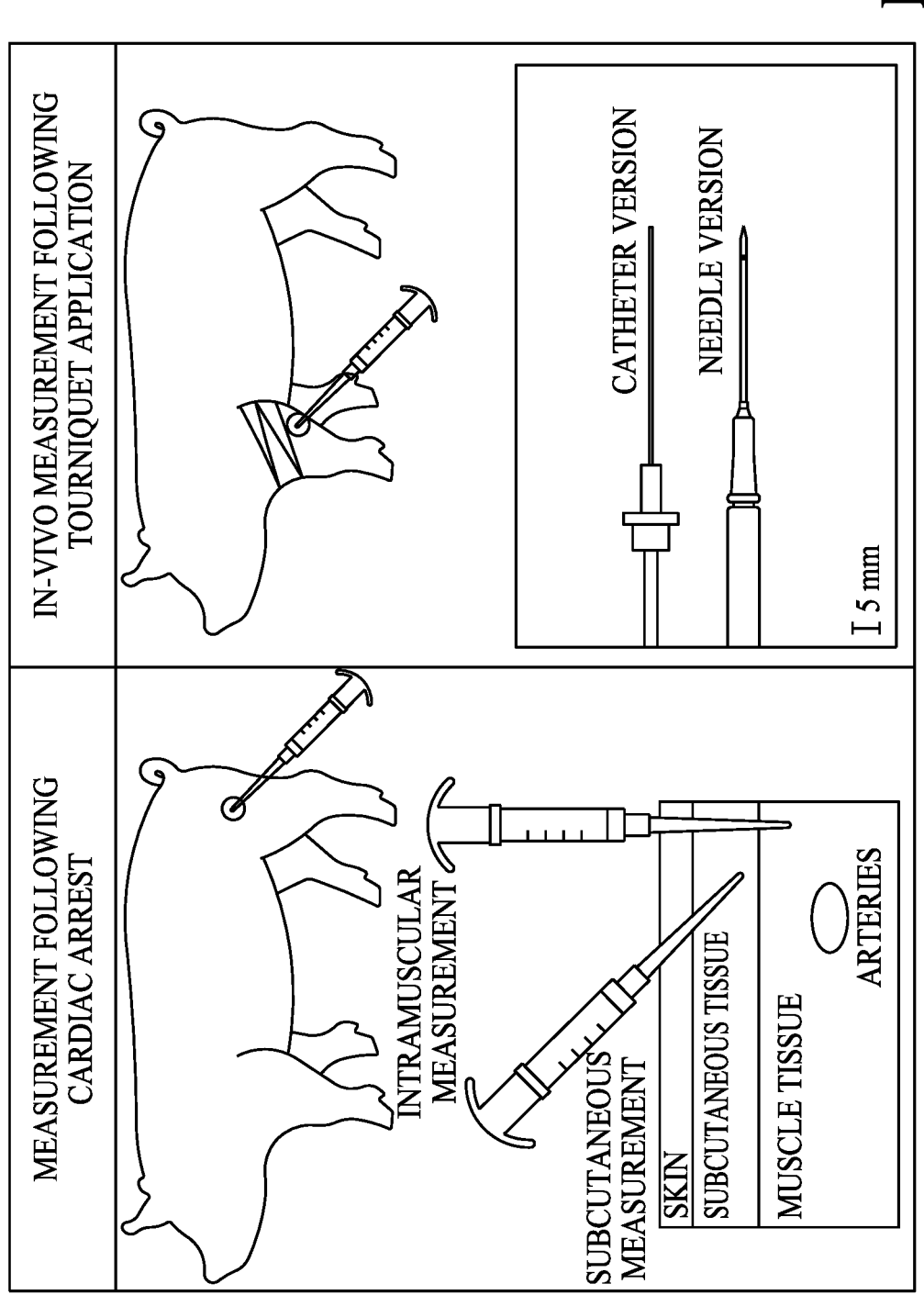
FIG. 30 shows experiments in a porcine model. In the first experiment, limb oxygenation was measured following the loss of cardiac function in a Yorkshire swine. The oxygen measurement was carried out at the hind limb (biceps femoris muscle). The needle was subsequently inserted into the muscle tissue, the subcutaneous tissue, and again into the muscle tissue. In the second experiment, limb oxygenation following the placement of a tourniquet was measured in the two pigs. The oxygen sensor was inserted into the flexor carpi ulnaris muscle in the front limb. The tourniquet was applied above the elbow joint over the triceps brachii and brachialis muscles. The illustration on the lower right shows the two different versions of the device used for the pig experiments.

Before applying the tourniquet, the oxygen sensor was inserted into the flexor carpi ulnaris muscle (indicated by a red dot in FIG. 30). In one pig, the oxygen sensor was needle-based, whereas in the second pig the catheter version (shown in FIG. 30 on the lower right) of the oxygen sensor was used. In addition to the prototype oxygen sensor, a laboratory-grade oxygen sensor (Profiling Oxygen Microsensor PM-PSt7, PreSens) was inserted with a catheter nearby in both experiments. All oxygenation measurements were temperature-compensated using the included thermocouple.

Figure 32:
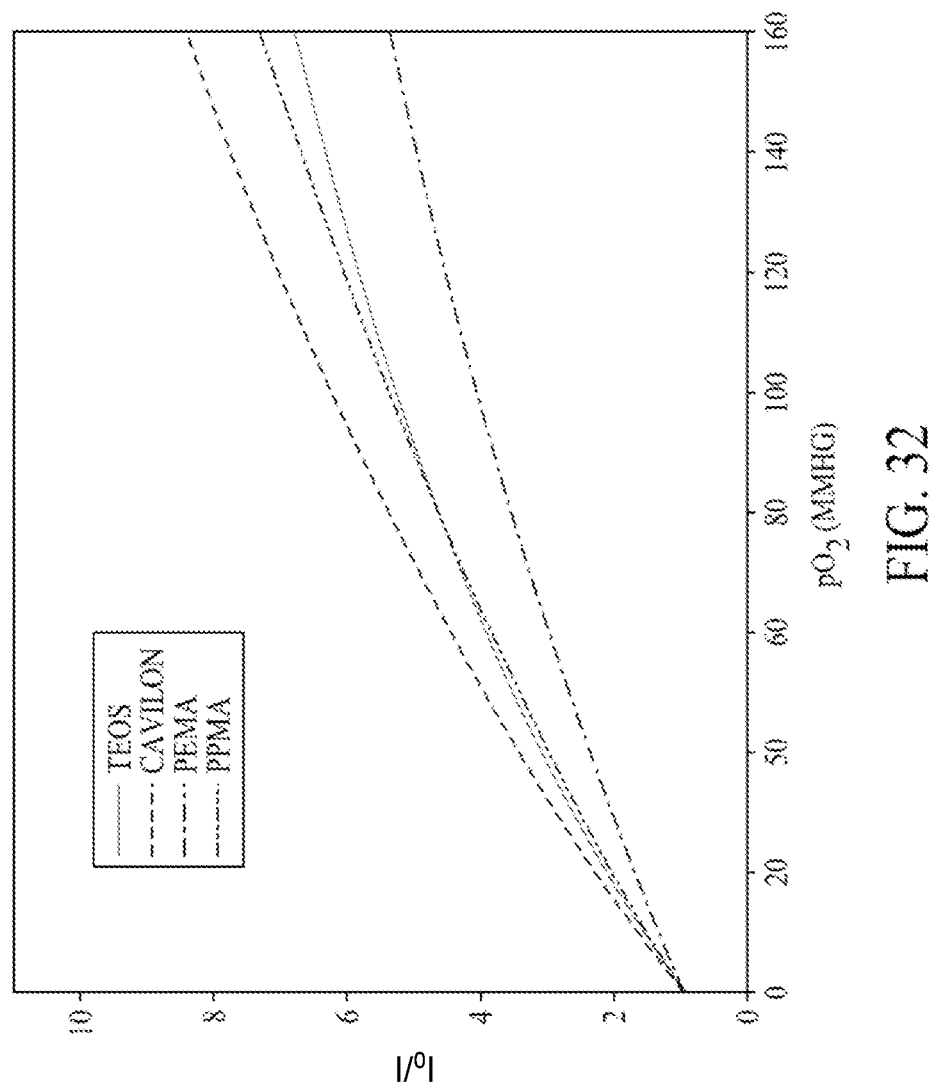
FIG. 32 shows a comparison of the Stern-Volmer distributions extracted for different matrices: 50 µM Pt(II)-pivaloyl in TEOS sol-gel+1.4 wt. % Triton X-100; 50 µM Pt(II)—pivaloyl in Cavilon™ film formulation, in 0.025 mg/µL PEMA, and in 0.025 mg/µL PPMA.

Oxygen Response. For the material selection process, the intensity of the phosphorescence signal was measured for different levels of pO$_2$ at room temperature and fitted with a one-dimensional Stern-Volmer relation modified with a factor f for non-accessible molecules. The resulting Stern-Volmer distributions are shown in FIG. 32. As can be clearly seen, the pivaloyl porphyrin in the Cavilon™ film matrix was the most sensitive over the whole measured pO$_2$ range with k=0.0742, f=0.0893, and I0=2.2. The PEMA coating was the least sensitive with k=0.0442, f=0.0771, and I0=1.2. The sensitivities of the TEOS sol-gel and PPMA were comparable; the TEOS sol-gel was slightly better at very low pO$_2$ and PPMA was better at high pO$_2$. The fitting parameters for PPMA were k=0.0593, f=0.0784, and I$_0$=1.9, while for TEOS sol-gel they were k=0.0731, f=0.16, and I0=2.2. Hence, the TEOS sol-gel matrix had the highest fraction of inaccessible porphyrins. The coating quality of the TEOS sol-gel material varied considerably between different fibers and, in general, the TEOS sol-gel did not adhere well, which can be attributed to significant cracking and had been already observed in previous studies. Applying only minimal force to the fiber tip resulted in a loss of the oxygen-sensing layer. The addition of surfactants yielded higher emission signals (best results with TEOS sol-gel+1.4 wt. % Triton X-100); however, the TEOS sol-gel still did not adhere well to the fiber tip.

Humidity Sensitivity. During its application the oxygen sensor will be exposed to blood and other bodily fluids, thus humidity insensitivity is crucial. The humidity sensitivity was measured by calculating the ratio of the signal in the emission peak under dry and humid (>90%) conditions at 0 mmHg. The pure TEOS sol-gel matrix was seen to be humidity sensitive with a dry-to-humid ratio of 2.1. While TEOS-based sol-gels have been reported earlier that did not display humidity sensitivity, the materials used in this work were made from formulations that contained DMSO and surfactants. Additional measurements on fibers coated with TEOS sol-gels of different compositions have shown that the humidity sensitivity on the fibers is mainly a result of the addition of DMSO to the TEOS formulation. The uniformity of the coating on a support substrate also plays a role, as the addition of surfactants has been found to improve the performance by minimizing the formation of cracks in the sol-gels coated on fibers.

The humidity sensitivity of TEOS decreased when surfactants were added, reaching a dry-to-humid ratio of 1.3-2. This likely arose as pure TEOS coatings showed significantly more cracks and thus provided more possibilities for water to enter the coating. No acrylate polymer-based coating showed significant humidity sensitivity, which can be attributed to their hydrophobicity.

Photobleaching. The intensity of phosphorescence emission from the oxygen-sensing materials was measured over time to determine the photobleaching rate. For this set of experiments, the LED was set to pulse every 15 seconds for a total duration of 1.5 hours. The irradiance from the LED on the oxygen-sensing material was estimated to be 160 nW/cm2.

TEOS sol-gel was found to have the highest bleaching rate with 5.0% h−1, followed by PEMA with 2.9%, and Cavilon™ film with 1.8%. PPMA was observed to have the lowest bleaching rate with only 0.2%. As the sensing tool required for compartment syndrome would be used only once for a duration of up to 10 hours, this minimal level of photobleaching would lead to a minor change in the overall brightness, ensuring high accuracy during use. Moreover, by carefully counting the number of the total delivered LED pulses, the low photobleaching rate was calibrated and accounted for.

Given its low photobleaching rate and humidity insensitivity, PPMA was selected as the optimal matrix material for the deep-tissue oxygen sensor. The pivaloyl porphyrin within the PPMA matrix was further assessed by acquiring phosphorescence intensity spectra and lifetime decays, using the FLS1000 steady state and phosphorescence lifetime spectrometer by Edinburgh Instruments (Livingston, U.K.). The resulting lifetime within the PPMA matrix was determined to be 98 μs, which is almost identical to the lifetime in DCM ($\tau_0$=101 μs), indicating good compatibility of the oxygen-sensing molecule and the matrix material.

pH Sensitivity. PPMA, the material with the lowest photobleaching rate and humidity insensitivity, was investigated for pH sensitivity. This was especially important for the application of the sensor: during muscle injuries, the intramuscular pH is expected to decrease from above pH 7 to below pH 5.2. Therefore, stability over this pH range is crucial. To measure pH sensitivity, the oxygen sensor was immersed into a buffer solution at pH 7.5 at mmHg $pO_2$, with the pH slowly lowered via the addition of 2 M hydrochloric acid drop-wise. An oxygen tension of 40 mmHg was chosen since it is in the middle of the $pO_2$ range of interest. No pH dependence could be detected.

Figure 33:
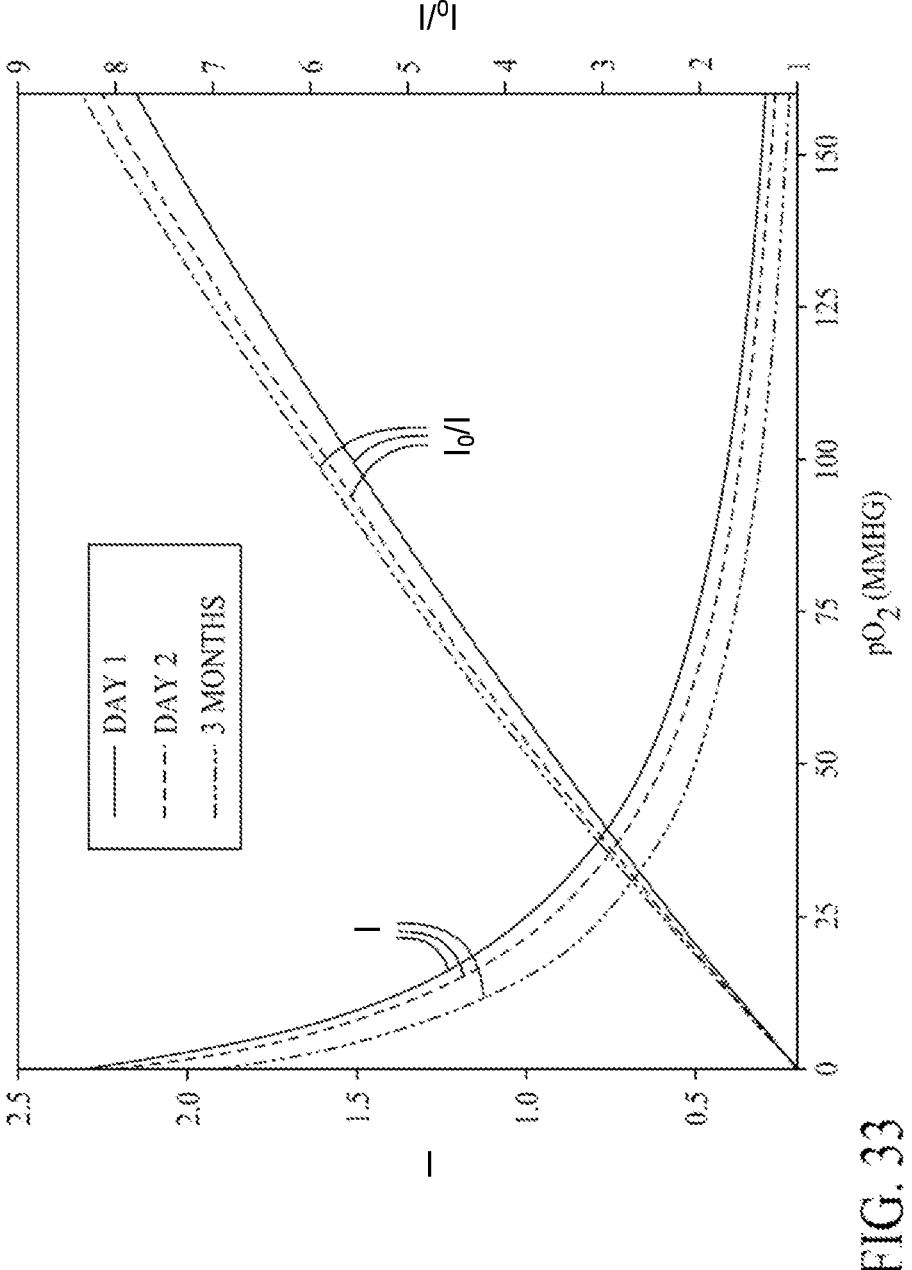
FIG. 33 shows Stern-Volmer distributions extracted from the calibration of the same sensor with Pt(II)-pivaloyl-PPMA coating at different time points and after usage in vivo including cleaning with isopropyl alcohol. The overall signal intensity I decreased with time, whereas the relative sensitivity $I_0/I$ increased.

Assessing Reusability. All sensors were generally used within 48 hours after they were made; hence, aging of the sensor was not critical for the measurements acquired in this study. To understand the impact of sensor insertion, removal, and cleaning, the sensors were re-evaluated after a period of more than 3 months from initial use in vivo and after rinsing with isopropyl alcohol. The overall signal intensity of the sensors was found to decrease by approximately 30%, whereas the relative sensitivity increased over time as can be seen in FIG. 33. Further investigations have shown that the drift is only prominent in the measurement of phosphorescence intensity and not in the lifetime measurement, where it was seen to be below 5% over a period of 3 months. This indicates that the drift in intensity is originating from changes in the optical properties of the matrix, for example scattering, and not from the oxygen-sensing molecule itself. Transferring to a lifetime-based readout in the future will significantly improve potential reusability.

Response Time. The final PPMA-based sensor with the silicone coating had a response time of 35 seconds to reach 1/e when transitioning from 160 to 0 mmHg. The response time is thought to be mainly limited by the diffusion of oxygen through the silicone layer as well as the physical absorption of oxygen in the silicone layer. It is important to note that this response is more than sufficient for the intended application, as compartment syndrome evolves over 30 min to several hours and oxygen levels will change over much smaller intervals.

Leaching Studies. To assess the biocompatibility of the material and fiber coating, the leaching of the porphyrin molecules from the material was analyzed by measuring the total platinum content found in samples after exposure to coated fibers. For this purpose, fibers were coated with different combinations of porphyrin, PPMA, and silicone recoating using the process described above. After drying, the fibers were placed inside a K2EDTA blood collection tube containing 1 mL of fresh whole pig blood and kept immersed for a duration of 7 hours. Additionally, fibers in needles were inserted into porcine tissue samples (skin and muscle) and left in the tissue for 7 hours. The blood and tissue were harvested immediately before the leaching study. The blood and the tissue samples with the fibers were kept at 36° C. during the entire time of the leaching study and were frozen immediately after the fibers were removed. Inductively coupled plasma mass spectrometry (ICP-MS) was used (Brooks Applied Labs, Bothell, WA) to analyze the platinum content of the samples. The results of all samples were within the error margin, identical to the reference sample of pure pig blood/tissue, demonstrating a lack of significant leaching.

Figure 34:
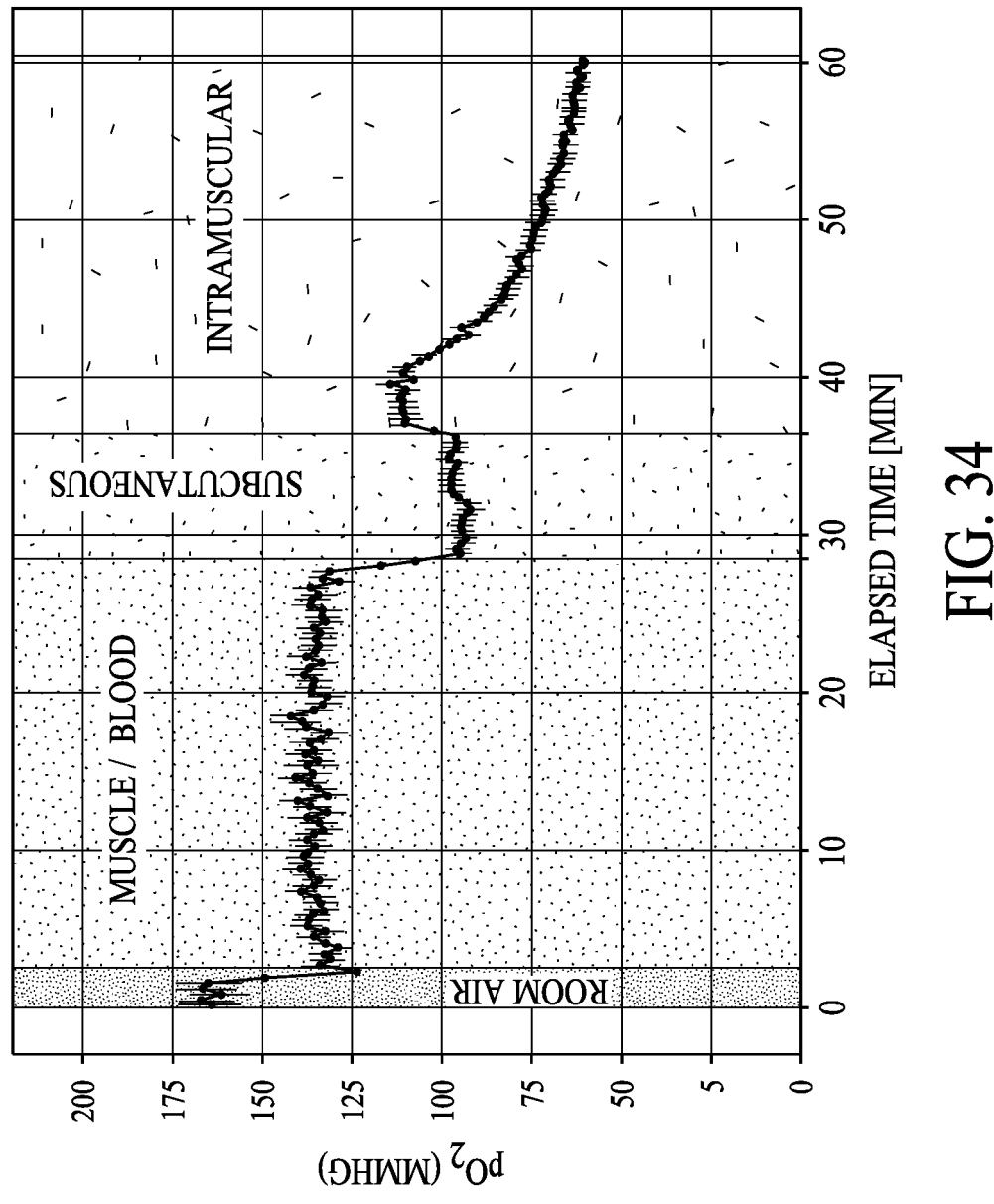
FIG. 34 shows limb oxygenation following the loss of cardiac function in a Yorkshire swine. The oxygen measurement was carried out in the hind limb (biceps femoris muscle) starting 1 minute after death. The needle was subsequently inserted into muscle tissue, the subcutaneous tissue, and again into the muscle tissue, as shown in FIG. 30.

In vivo Results. The results from the limb oxygenation measurement after the loss of cardiac function are shown in FIG. 34.

The oxygen tension in a given tissue is a balance between both supply, via the vasculature, and demand, via the consumption of oxygen during cellular respiration. The muscle tissue is known to consume oxygen rapidly, as opposed to tissues such as the skin, which very slowly utilize molecular oxygen. An overdose of Fatal Plus induces cardiac arrest, causing the cessation of pulsatile flow and therefore perfusion into the tissue. It was expected that, when inserted into the muscle, the probe would measure an exponential decay of oxygen tension, similar to that observed in previous studies.

The $pO_2$ measured at the first insertion location at the biceps femoris muscle was found to be stable at 130 mmHg. This value seems to be high at first, and however, can be explained by the high $FiO_2$ of 1. In addition, as the needle gauge of 18 was large and the needle was not smooth due to the drilled holes, the insertion of the needle may have induced bleeding at the site of insertion resulting in the observed high $pO_2$ levels.

Following approximately 30 minutes of measurement, the needle was then moved and inserted into the skin above the biceps femoris muscle. Within the slowly oxygen-consuming skin, the prototype oxygen sensor measured a steady oxygen tension of 90 mmHg, a value in agreement with previous studies measuring subcutaneous oxygenation in pigs.

Following 8 minutes of measurement, the needle was reinserted into the femoris muscle at a different location. At this second location, the oxygen partial pressure was observed to slowly decrease over the course of 20 min to a final value of approximately 60 mmHg. As this decrease in $pO_2$ was much slower than the equilibration time of the sensor, this decay was attributed to the slow metabolic rate of the muscle tissue and residual heart activity after pentobarbital injection.

It is well known that intramuscular $pO_2$ is heterogeneous within a single muscle, varies between individuals, and is shown to strongly depend on $FiO_2$. In normally perfused tissue, previous studies measured values between 60 mmHg and 80 mmHg in canine models at a $FiO_2$ of 0.5. Some previous studies measured an intramuscular $pO_2$ between 4.0 mmHg and 50.6 mmHg with an average difference of 19.9 mmHg at unknown $FiO_2$. Some other previous studies have measured a significant difference in the intramuscular $pO_2$ in a rat model between $FiO_2$=0.21 (room air) and $FiO_2$=1, with $pO_{2=30}$-45 and 120-220 mmHg, respectively. Results were also found by others in rats and mice, respectively. These values fall within agreement with the measurements in the porcine muscle at $FiO_2$=1 immediately post-mortem. It should be noted that conversations with large animal surgical staff confirmed these findings.

Figure 35:
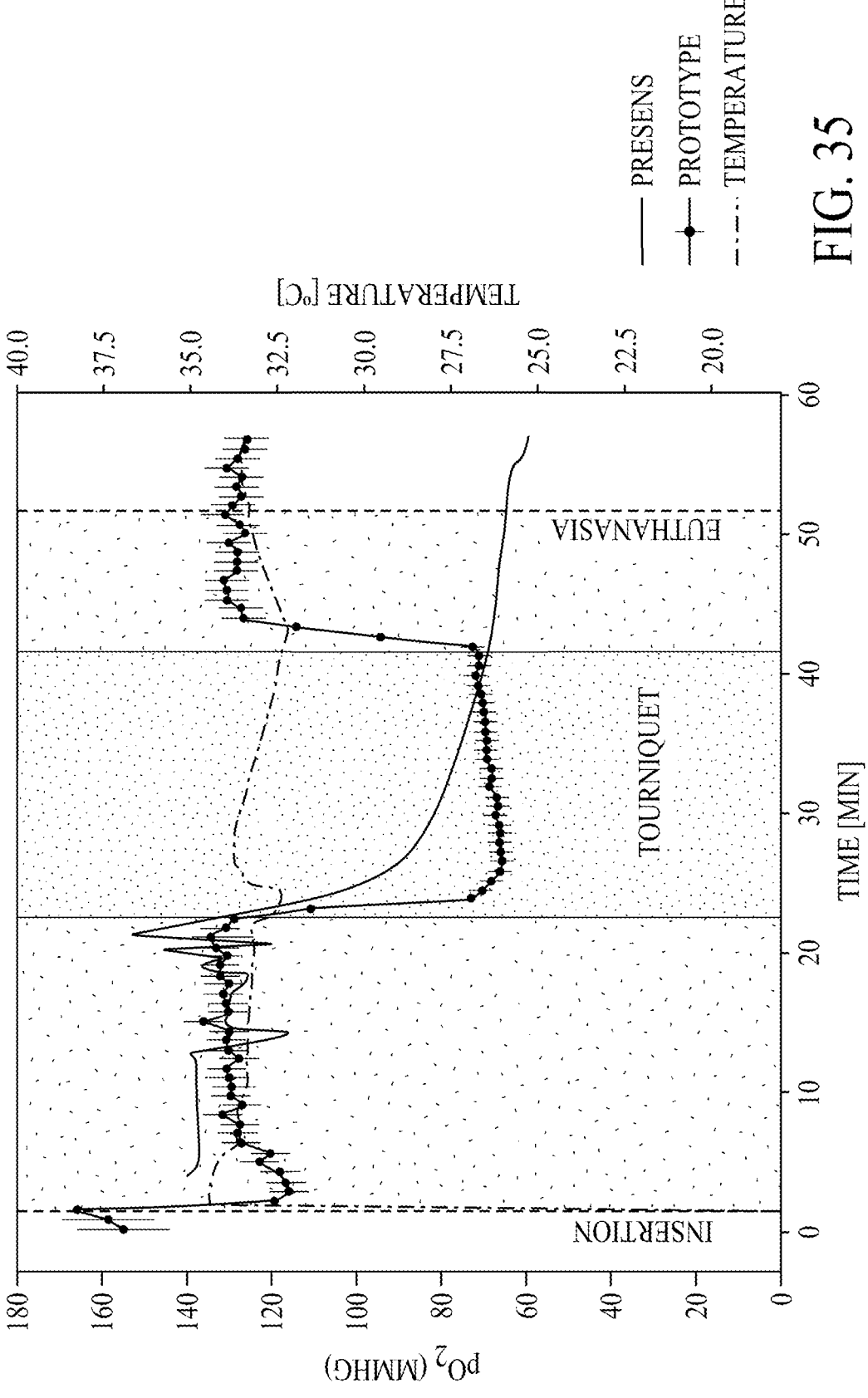
FIG. 35 shows limb oxygenation following the placement of a tourniquet with the pig 1 (Hampshire breed) and a needle-based measurement.
Figure 36:
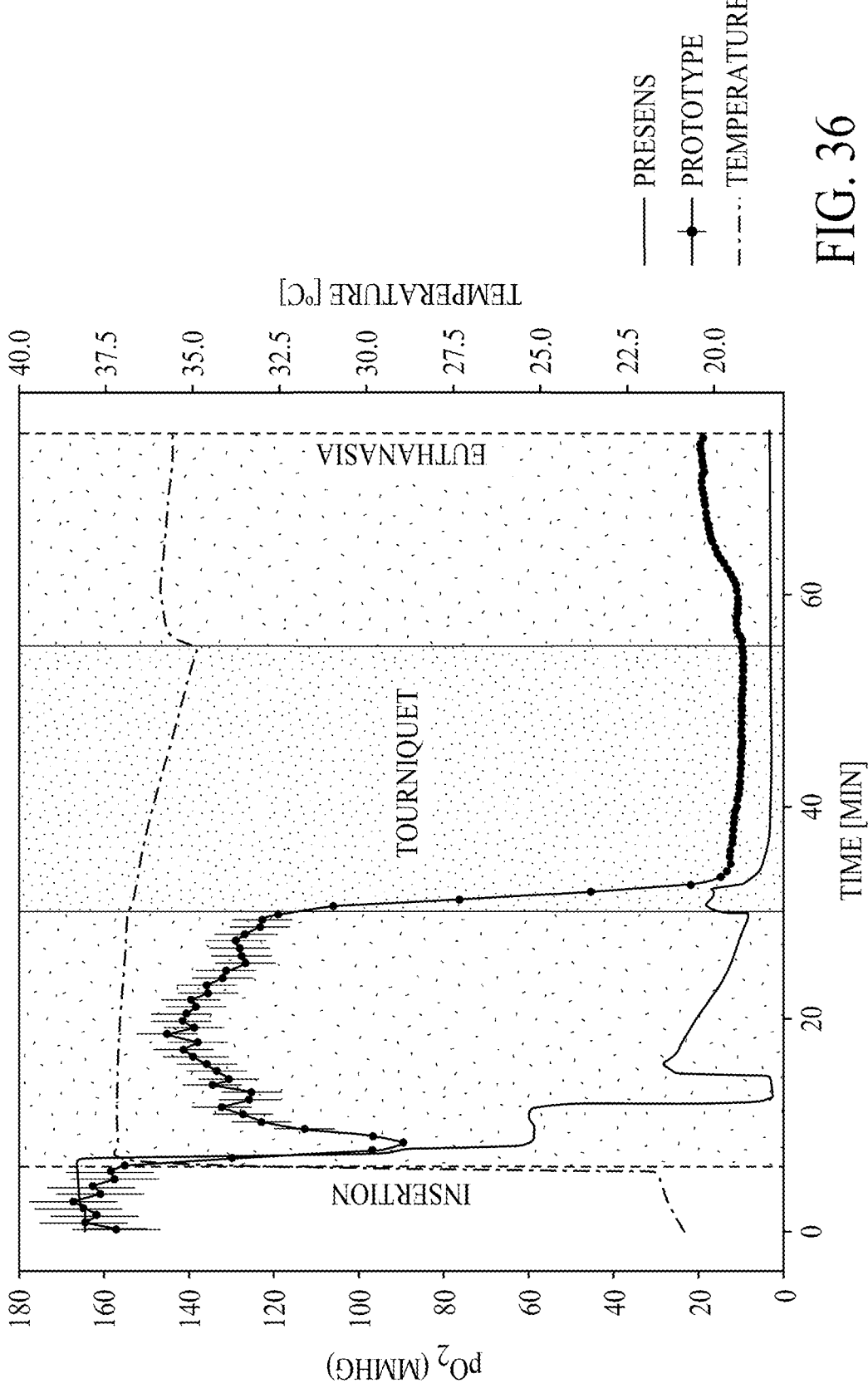
FIG. 36 shows limb oxygenation following the placement of a tourniquet with the pig 2 (Yorkshire breed), and a catheter-based measurement.

The results from the in vivo tourniquet model are shown in FIGS. 35 and 36. In both pigs, $pO_2$ values of 130 mmHg were measured before tourniquet application, which is in agreement with the measurement in the first experiment and with measurements in rat models at $FiO_2$=1. In both pigs, when the tourniquet was applied, the $pO_2$ dropped within less than a min to 65 mmHg and 15 mmHg, respectively. In the first pig, the $pO_2$ immediately increased back to its initial value after tourniquet release, whereas in the second pig the $pO_2$ only increased by approximately 10 to 20 mmHg over the course of 15 min.

The different $pO_2$ levels measured in the two pigs during and after tourniquet application can be explained by the different forces with which the tourniquets were applied. The low $pO_2$ of only 20 mmHg in the second pig indicated severe tissue damage due to the applied force. This is also in agreement with the observed change in skin color, which was much more drastic in the second pig.

In both pigs, the commercial oxygen sensor did not adequately reproduce the results measured with the prototype sensor. It is not clear why the commercial sensor shows this behavior; however, it has to be noted that it was not designed for intramuscular nor any in vivo applications and may have interacted with blood, was damaged, or rendered inert due to fouling.

To measure deep-tissue oxygenation, this study was focused on the development, construction, and validation of a fiber-based portable intramuscular oxygen-sensing device. TEOS sol-gel, 3M Cavilon™ film, PEMA, and PPMA were evaluated as matrix materials to host a brightly emitting porphyrin oxygen sensor. The Pt(II)-pivaloyl porphyrin in PPMA was shown to have no humidity or pH dependence and exhibited a low photo-bleaching rate, which was essential for an intramuscular intensity-based $pO_2$ measurement.

The PPMA prototype sensors were tested in two different porcine models and showed an appropriate and reproducible response to changes in oxygenation. Subcutaneous measurements were in agreement with earlier measurements in rat models. Muscle oxygenation right after insertion of the sensor was measured to be around 130 mmHg, which can be explained by the high $FiO_2$ of 1 and additional bleeding due to needle insertion. In the future, bleeding could be reduced by using smaller gauge needles or by proper placing of the needle/catheter using ultrasound guidance. Both prototype sensors showed fast changes in the $pO_2$ following tourniquet application. After the release of the tourniquet, intramuscular $pO_2$ in the first pig increased rapidly to pre-tourniquet levels, whereas in the second pig the $pO_2$ only slowly increased by approximately 10 mmHg. This was most probably caused by tissue injury induced by an overtightened tourniquet in the second pig. In the future, this could be controlled by applying a pneumatic tourniquet with 40-100 mmHg above the limb occlusion pressure; however, it is not straightforward to fit a tourniquet to the leg shape of a pig while still having access to muscles. The commercial oxygen sensor used in parallel, which notably determines $pO_2$ based on the much more stable lifetime measurement, did not respond as expected in vivo.

Even though in retrospect it would have been interesting to explore lower (or even several) values of $FiO_2$, it should be noted that the performance of the sensor is not largely affected by $FiO_2$. In addition, when using lower $FiO_2$, tissue $pO_2$ is expected to decrease to values where the sensor shows higher sensitivity and accuracy as shown in FIG. 31.

While the needle-based version of the current prototype seems to be appropriate for single-point measurements, due to its flexibility, the catheter-based version can be left in the tissue for a longer time. Thus, $pO_2$ values could be acquired over a long time frame so that an oxygen trend could be measured rather than an overall value. This could be advantageous since intramuscular oxygenation is expected to be heterogeneous inside a compartment. Furthermore, a single measurement could be enhanced by additional sensors arranged spatially in a grid, longitudinally along with the probe, or both to acquire regional tissue $pO_2$ maps to understand the distribution of $pO_2$ for the improved diagnosis of ACS.

Whereas tissue oxygenation seems to be a much more physiologically relevant measurement for tissue health than total pressure, further investigations in a large animal compartment syndrome model are necessary to understand the possible benefit of the device for the assessment of compartment syndrome. In addition, a compartment syndrome model would give further insight into the effect of a change in the total pressure on the oxygen partial pressure measurement. Measurements in a chamber where the total pressure was changed while keeping the ratio of nitrogen and air constant showed that changes in the total pressure are directly related to changes in the oxygen partial pressure. However, it has to be noted that this model does not reflect the full complexity of the physiology during compartment syndrome, and additional in vivo studies will be needed to assess the interplay between total pressure and $pO_2$.

For first-in human use, the device needs further miniaturization in the needle gauge to decrease discomfort during insertion. The small 200 μm optical fiber used in the prototype is ideally suited for that and small gauge needles with side ports can be custom-made by commercial producers. To reduce the possibility of breaking, the empty space around the fiber in the needle could be filled up with epoxy resin so that the fiber tip is mounted flush within the surface of the epoxy resin. In addition, the side ports could be substituted by a porous housing material.

Even though the fiber-part of the sensor will be a disposable device, for safe usage in humans, a fabrication of the probe under sterile conditions or sterilization of the oxygen sensor after fabrication may be necessary. As mentioned earlier, a sterilization process using EtO is favorable since it has been shown to be safe for fiber-based sensors and polymer coatings. The effects on the fiber and oxygen-sensing coatings in our prototype still need to be investigated. Cell toxicity assays can be used to further assess biocompatibility of this oxygen sensor. The device introduced in this Example was specifically developed to address the unmet need for early and adequate diagnosis of ACS. In the future, a total pressure sensor can be added to the same device to measure pressure. Also, this would allow physicians to get a direct comparison to the current diagnosis standard. To get a holistic understanding of this disease, it might be even beneficial to measure additional parameters such as pH and lactate levels, in parallel in the same device. The measurement of these parameters in parallel could have additional utility in the monitoring and diagnosis of other hypoxia-related diseases.

Example 3

Fusion of Lifetime and Intensity Derived $pO_2$ Estimates

Figure 37:
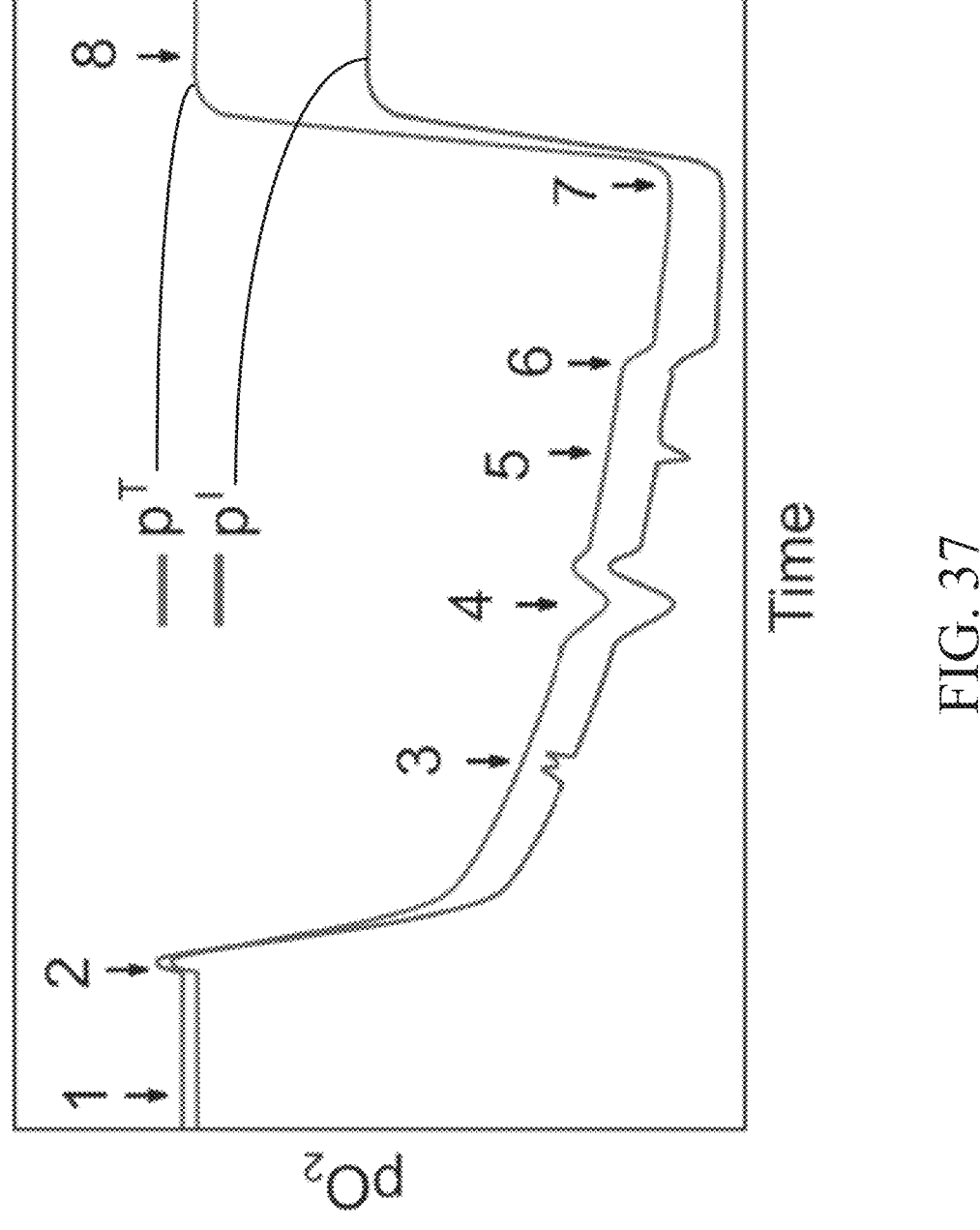
FIG. 37 shows a typical measurement during a clinical trial, where $p^T$ is the $pO_2$ derived from lifetime and $p^I$ from intensity.

FIG. 37 shows schematically a typical measurement during a clinical trial, where $p^T$ is the $pO_2$ derived from lifetime and $p^I$ from intensity. In FIG. 37, the arrows indicate: 1. Start measurement at atmospheric pressure. 2. Apply device to skin. 3. Observation of motion artifact in intensity but not lifetime. 4. Observation of change in $pO_2$ due to change in blood flow in both metrics. 5. Motion artifact in intensity. 6. Change in $pO_2$ due to change in blood flow. 7. Remove device from skin. 8. Equilibration back to atmospheric $pO_2$.

What is typically seen is that $p^T$ is slightly noisier than $p^I$, but reliably goes back to atmospheric $pO_2$ after removal. $p^I$ shows enhanced detail during $pO_2$ changes, but is subject to motion artifacts and does not always cycle back to atmospheric $pO_2$, likely due to photobleaching of the phosphorescent molecules.

Ideally, one wants to keep the quantitative (slow trend) value of $p^T$ and the sensitivity of $p^I$. We can combine both $pO_2$ metrics using some of the following approaches. These approaches serve as illustrative examples of ways these signals can be either averaged, combined, or correlated and are not an exhaustive list of all possible algorithmic methods.

1. After calibration, obtain the linear regression coefficients $p^I=m*p^T+b$ and calculate the combined $pO_2$ metric:

$$pO_2=(p^I-b)/m$$

2. Combine the long-term moving average of $p^T$ with the instantaneous changes in $p^I$, which can be obtained by subtracting the long-term moving average of $p^I$ to $p^I$. This can be done by low-pass filtering $p^T$ (namely $LP(p^T)$) and high-pass filtering $p^I$ ($HP(p^I)$), or $p^I-LP(p^I)$. The combined output would be:

$$pO_2=LP(p^T)+HP(p^I).$$

3. Define a coefficient between [0,1] which reflects the correlation between $p^T$ and $p^I$, their derivatives with respect to time, etc., e.g., through a correlation, cross-correlation function, and produce a $pO_2$ metric which combines $p^I$ and $p^T$ with different weights. The weights determine how much of each signal makes up the combined $pO_2$ metric at each instant, taking into account if features appearing in both curves are common or not (if there is correlation between signals or not). For example, $$C=abs(corr(p^T,p^I)),C=abs(corr(dp^T/dt,dp^I/dt)),$$

and with possible combined $pO_2$ definitions being $$pO_2=C*p^I+(1-C)*p^T, \text{ or}$$

$$pO_2=sqrt(C^2*p^{I^2}+(1-C)^2*p^{T^2}).$$

The present disclosure has described one or more preferred embodiments, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular embodiments or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or embodiments. Further, references to particular rotational or other movements (e.g., counterclockwise rotation) is generally intended as a description only of movement relative a reference frame of a particular example of illustration.

In some embodiments, aspects of the disclosure, including computerized implementations of methods according to the disclosure, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, embodiments of the disclosure can be implemented as a set of instructions, tangibly embodied on a non-transitory computer-readable media, such that a processor device can implement the instructions based upon reading the instructions from the computer-readable media. Some embodiments of the disclosure can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular embodiments of the disclosure. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use embodiments of the disclosure. Various modifications to the illustrated examples will be readily apparent to those skilled in the art, and the generic principles herein can be applied to other examples and applications without departing from the principles disclosed herein. Thus, embodiments of the disclosure are not intended to be limited to embodiments shown, but are to be accorded the widest scope consistent with the principles and features disclosed herein and the claims below. The following detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

What is claimed is:

1. A sensor system for monitoring a patient, the sensor system comprising:
   a first probe sensitive to an analyte and comprising a plurality of operational ranges for monitoring a patient, the plurality of operational ranges having at least a first operational range and a second operational range;
   a photon source configured to direct photons to the first probe, wherein the first probe is configured to receive the directed photons and to emit light in response to the received photons;
   a photodetector configured to detect the emitted light; and
   a controller in communication with the photon source and the photodetector, and configured to:
      control the photon source to such that, in operation, the photon source directs the directed photons to the first probe according to a first time-varying profile and the first probe is excited relative to the first operational range and relative to the second operational range and emits the emitted light in response to the received photons;
      receive optical data from the photodetector based on an interaction between the emitted light and the photodetector with the first probe operating in the first operational range and in the second operational range, wherein the optical data includes a second time-varying profile;
      determine a difference between the first time-varying profile and the second time-varying profile; and
      based on the determined difference between the first time-varying profile and the second time-varying profile, determine a parameter associated with the analyte.

2. The sensor system of claim 1, wherein the first probe includes respective phosphors or phosphorescent regions that each provide one of the first operational range and the second operational range.

3. The sensor system of claim 1, wherein the controller is further configured to select a first characteristic of the first time-varying profile to excite the first probe relative to the first operational range and select a second characteristic of the first time-varying profile to excite the first probe relative to the second operational range.

4. The sensor system of claim 1, wherein the controller is further configured to control the photon source such that in operation the photon source directs the directed photons to the first probe according to the first time-varying profile to simultaneously excite the probe relative the first operational range and the second operational range.

5. The sensor system of claim 1, wherein the first time-varying profile comprises a first signal for exciting the first probe relative to the first operational range and a second signal for exciting the first probe relative to the second operational range.

6. The sensor system of claim 1, wherein the first operational range has a first sensitivity or a first response curve relative the analyte and the second operational range has a second sensitivity and or second response curve relative to the analyte.

7. The sensor system of claim 1, wherein an operational range of the sensor system is defined by a sum of the first operational range and the second operational range.

8. The sensor system of claim 1, wherein the controller is configured to form the first time-varying profile by combining a plurality of sine waves, a plurality of square waves, a plurality of triangle waves, a plurality of sawtooth waves, a plurality of impulse functions, or a plurality of non-periodic waves.

9. The sensor system of claim 1, wherein the second time-varying profile comprises a time-varying amplitude wave comprising a phase and an amplitude and the analyte includes a partial pressure and the controller is further configured to determine the phase and the amplitude and determine the partial pressure based on a difference in the phase and the amplitude.

10. The sensor system of claim 1, wherein the first time-varying profile includes a plurality of frequencies including at least a first frequency for the first operational range and a second frequency for the second operational range.

11. The sensor system of claim 1, further comprising a second probe having a third operational range and wherein the controller is further configured to create the first time-varying profile from a plurality of signals having at least a first signal and a second signal, the first signal having a first characteristic and the second signal having a second characteristic wherein the first characteristic is distinct from the second characteristic and the first characteristic target the first probe and second characteristic target the second probe.

12. The sensor system of claim 1, wherein the difference is a phase difference.

13. The sensor system of claim 1, wherein the analyte includes oxygen or the parameter includes partial pressure or both.

14. The sensor system of claim 1, wherein the first probe is capable of physically contacting a patient tissue or capable of fluidly contacting a zone disposed over a portion of the patient tissue in contact with, gas communication with, or fluid communication with the zone on the patient that is separated from the ambient environment by a membrane which is impermeable or semi-permeable to the analyte.

15. The sensor system of claim 1, wherein the first probe includes:

a semipermeable layer enabling the analyte to selectively diffuse therethrough; and a light absorbing layer configured to absorb light directed therethrough, a light scattering layer configured to scatter light directed thereto or a light reflective layer configured to reflect light directed therethrough, and wherein the first probe is positioned between the semipermeable layer and the light absorbing layer or between the semipermeable layer and the light scattering layer or between the semipermeable layer and the light reflective layer.

16. The sensor system of claim 1, further comprising:

a first optical filter optically coupled to the photon source and configured to filter the photons emitted from the photon source that pass through the first optical filter; and a second optical filter optically coupled to the photodetector and configured to filter light that passes through the second optical filter to the photodetector.

17. The sensor system of claim 1, wherein the parameter includes a partial pressure of the analyte and wherein, together, the first operational range and a second operational range extends over an overall range between substantially 0 mmHg and 160 mmHg.

18. The sensor system of claim 1, wherein the first time-varying profile includes a waveform including a frequency and the second time varying profile includes characteristics and the controller is further configured to adjust the frequency based on the characteristics.

19. The sensor system of claim 1, wherein the first time-varying profile includes a sine wave of programmable frequency, a sum of sine waves of programmable frequency, and a square wave of programmable frequency, and the second time-varying profile includes characteristics and the controller is further configured to select the sine wave of programmable frequency, the sum of sine waves of programmable frequency, or the square wave of programmable frequency for the first time-varying profile based on the characteristics.

20. The sensor system of claim 1, wherein the first probe includes a first phosphor having the first operational range and a second phosphor different from the first phosphor and having the second operational range, wherein the first phosphor is sensitive to a first partial pressure range and defining the first operational range and the second phosphor is sensitive to a second partial pressure range different from the first partial pressure range and defining the first operational range and the second operational range.

* * * * *